US010909730B2

(12) United States Patent
An et al.

(10) Patent No.: US 10,909,730 B2
(45) Date of Patent: Feb. 2, 2021

(54) FREE-BREATHING AND SELF-NAVIGATED MRI METHOD FOR DEFORMABLE MOTION DERIVATION

(71) Applicants: Hongyu An, St. Louis, MO (US); Cihat Eldeniz, St. Louis, MO (US)

(72) Inventors: Hongyu An, St. Louis, MO (US); Cihat Eldeniz, St. Louis, MO (US)

(73) Assignee: Washington University, St. Louis, MO (US)

( * ) Notice: Subject to any disclaimer, the term of this patent is extended or adjusted under 35 U.S.C. 154(b) by 441 days.

(21) Appl. No.: 15/872,380

(22) Filed: Jan. 16, 2018

(65) Prior Publication Data

US 2018/0204358 A1 Jul. 19, 2018

Related U.S. Application Data

(60) Provisional application No. 62/446,193, filed on Jan. 13, 2017.

(51) Int. Cl.
*G06T 11/00* (2006.01)
*G06T 7/00* (2017.01)
(Continued)

(52) U.S. Cl.
CPC .......... *G06T 11/006* (2013.01); *A61B 5/055* (2013.01); *A61B 5/7285* (2013.01);
(Continued)

(58) Field of Classification Search
CPC ..... G06T 11/006; G06T 7/0014; G06T 7/248; G06T 2207/10088; G06T 2211/436;
(Continued)

(56) References Cited

U.S. PATENT DOCUMENTS 8,195,417 B2 * 6/2012 Feiweier ................ A61B 6/037
702/95
9,940,713 B1 * 4/2018 Bhat ................ G01R 33/56509
(Continued)

FOREIGN PATENT DOCUMENTS

WO 2016069602 A1 5/2016

OTHER PUBLICATIONS

Campbell-Washburn, A.E. et al., "Distortion correction of Golden Angle radial images with GIRF-predicted k-space trajectories using the gradient waveform history," in Proceedings International Society for Magnetic Resonance in Medicine Scientific Meeting, ISMRM, Singapore, Abstract 0518, 2 pages (2016).

(Continued)

*Primary Examiner* — Sanjay Cattungal
(74) *Attorney, Agent, or Firm* — Armstrong Teasdale LLP

(57) ABSTRACT

Systems and methods for producing motion-corrected MR images that include an MRI scanner with a plurality of coils in which the plurality of coils is configured to detect a plurality of MR imaging datasets are provided. Each MR imaging dataset includes a plurality of MR signals detected by one coil of the plurality of coils. The system further includes a controller operatively coupled to the MRI scanner that includes at least one processor and a non-volatile memory. The controller further includes an image processing unit configured to receive the plurality of MR imaging datasets associated with the plurality of coils, identify a motion cycle using an automated motion detection method, and to partition the plurality of MR imaging datasets into a plurality of image groups, in which each image group comprises a portion of the plurality of MR imaging datasets associated with one of the phases of the motion cycle.

12 Claims, 38 Drawing Sheets
(28 of 38 Drawing Sheet(s) Filed in Color)

(51) Int. Cl.
| | |
|---|---|
| *G06T 7/246* | (2017.01) |
| *A61B 5/055* | (2006.01) |
| *G01R 33/00* | (2006.01) |
| *G01R 33/28* | (2006.01) |
| *A61B 5/00* | (2006.01) |
| *G01R 33/565* | (2006.01) |
| *G01R 33/567* | (2006.01) |
| *A61B 5/024* | (2006.01) |
| *A61B 5/08* | (2006.01) |
| *G01R 33/48* | (2006.01) |

(52) U.S. Cl.
CPC ..... *G01R 33/0005* (2013.01); *G01R 33/0029* (2013.01); *G01R 33/28* (2013.01); *G01R 33/5676* (2013.01); *G01R 33/56509* (2013.01); *G06T 7/0014* (2013.01); *G06T 7/248* (2017.01); *A61B 5/024* (2013.01); *A61B 5/0816* (2013.01); *G01R 33/4826* (2013.01); *G06T 2207/10088* (2013.01); *G06T 2211/436* (2013.01)

(58) Field of Classification Search
CPC ....... A61B 5/7285; A61B 5/055; A61B 5/024; A61B 5/0816; G01R 33/56509; G01R 33/5676; G01R 33/0029; G01R 33/28; G01R 33/0005; G01R 33/4826
See application file for complete search history.

(56) References Cited

U.S. PATENT DOCUMENTS

| | | | |
|---|---|---|---|
| 10,362,992 B2* | 7/2019 | Rajamani | A61B 5/7289 |
| 2014/0210469 A1* | 7/2014 | Cheng | G01R 33/56509 |
| | | | 324/309 |
| 2015/0015255 A1* | 1/2015 | Krueger | G01R 33/5676 |
| | | | 324/309 |
| 2015/0077112 A1 | 3/2015 | Otazo et al. | |
| 2015/0091563 A1 | 4/2015 | Lu et al. | |
| 2015/0253409 A1* | 9/2015 | Feiweier | A61B 5/7207 |
| | | | 324/307 |
| 2015/0265219 A1* | 9/2015 | Feiweier | G01R 33/56509 |
| | | | 600/476 |
| 2017/0035298 A1* | 2/2017 | Contijoch | A61B 5/0044 |
| 2017/0074959 A1* | 3/2017 | Li | A61B 5/7289 |
| 2017/0112449 A1* | 4/2017 | Huang | A61B 5/113 |
| 2017/0307712 A1* | 10/2017 | Cai | G01R 33/56316 |
| 2017/0328970 A1* | 11/2017 | Bi | G01R 33/5676 |
| 2018/0140216 A1* | 5/2018 | Li | G01R 33/56509 |
| 2018/0204358 A1* | 7/2018 | An | G01R 33/28 |
| 2019/0154785 A1* | 5/2019 | Zhou | A61B 5/7289 |

OTHER PUBLICATIONS

Campbell-Washburn, A.E. et al., "Real-time distortion correction of spiral and echo planar images using the gradient system impulse response function," Magnetic Resonance Medicine 75(6): 2278-2285 (2016).

Candes, E.J. et al., "Enhancing Sparsity by Reweighted I(1) Minimization," Journal of Fourier Analysis and Applications, 14(5-6): 877-905 (2008).

Eldeniz, C. et al., "Consistently-Acquired Projections for Tuned and Robust Estimation—A self-navigated respiratory motion correction approach," Investigative Radiology, 53(5): 293-305 (2018).

Eldeniz, C. et al., "Cosine-Modulated Acquisition Cleans Spectra for Better Respiratory Cine," in Proceedings International Society for Magnetic Resonance in Medicine Scientific Meeting, ISMRM, Singapore, Abstract 6776, 1 page (2016).

Feng, L. et al., "XD-GRASP: Golden-angle radial MRI with reconstruction of extra motion-state dimensions using compressed sensing," Magnetic Resonance in Medicine, 75(2): 775-88 (2016).

Grimm, R. et al., "Self-gated MRI motion modeling for respiratory motion compensation in integrated PET/MRI," Medical Image Analysis, 19(1): 110-120 (2015).

Grimm, R. et al., "Self-gated radial MRI for respiratory motion compensation on hybrid PET/MR systems," International Conference on Medical Image Computing and Computer-Assisted Intervention : MICCAI 2013: Medical Image Computing and Computer-Assisted Intervention—MICCAI 2013, 16(Pt 3): 17-24.

Li, B. et al. "Respiratory Phase Compressed Sensing Reconstruction using Highly Under-sampled Stack-of-stars Radial Acquisition," in Proceedings International Society for Magnetic Resonance in Medicine Scientific Meeting, ISMRM, 23: Abstract 3806, 1 page (2015).

Liu, J. et al., "Respiratory and cardiac self-gated free-breathing cardiac CINE imaging with multiecho 3D hybrid radial SSFP acquisition," Magnetic Resonance in Medicine, 63(5): 1230-1237 (2010).

Lustig, M. et al., "Sparse MRI: The application of compressed sensing for rapid MR imaging," Magnetic Resonance in Medicine, 58(6): 1182-1195 (2007).

Munoz, C. et al., "MR-Based Cardiac and Respiratory Motion-Compensation Techniques for PET-MR Imaging," PET Clinics, 11(2): 179-191 (2016).

Pang, J. et al., "ECG and navigator-free four-dimensional whole-heart coronary MRA for simultaneous visualization of cardiac anatomy and function," Magnetic Resonance of Medicine, 72(5): 1208-1217 (2014).

Spincemaille, P. et al., "Z intensity-weighted position self-respiratory gating method for free-breathing 3D cardiac CINE imaging," Magnetic Resonance Imaging, 29(6): 861-868 (2011).

Wang, Y. et al., "Navigator-echo-based real-time respiratory gating and triggering for reduction of respiration effects in three-dimensional coronary MR angiography," Radiology, 198(1): 55-60 (1996).

Wurslin, C., et al., Respiratory motion correction in oncologic PET using T1-weighted MR imaging on a simultaneous whole-body PET/MR system. Journal of Nuclear Medicine, 54(3): 464-471 (2013).

* cited by examiner

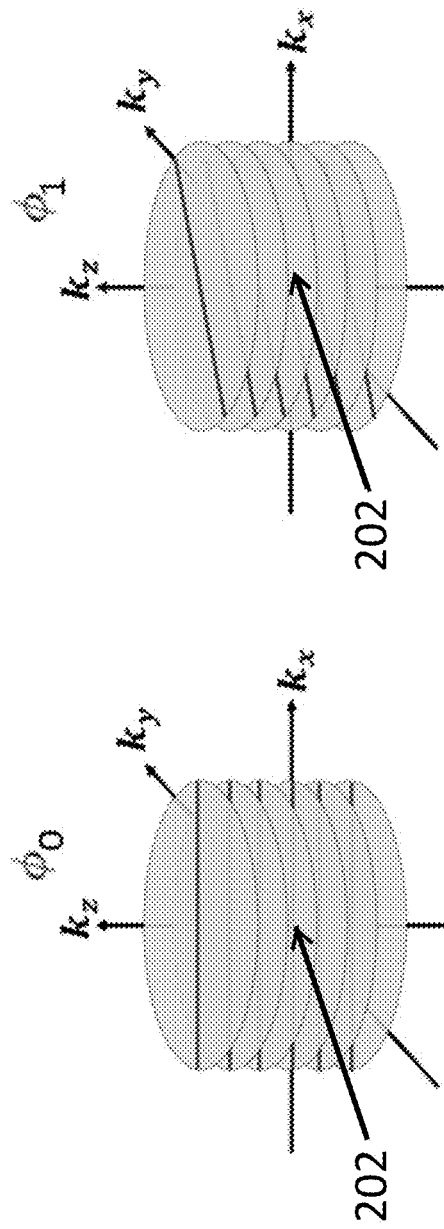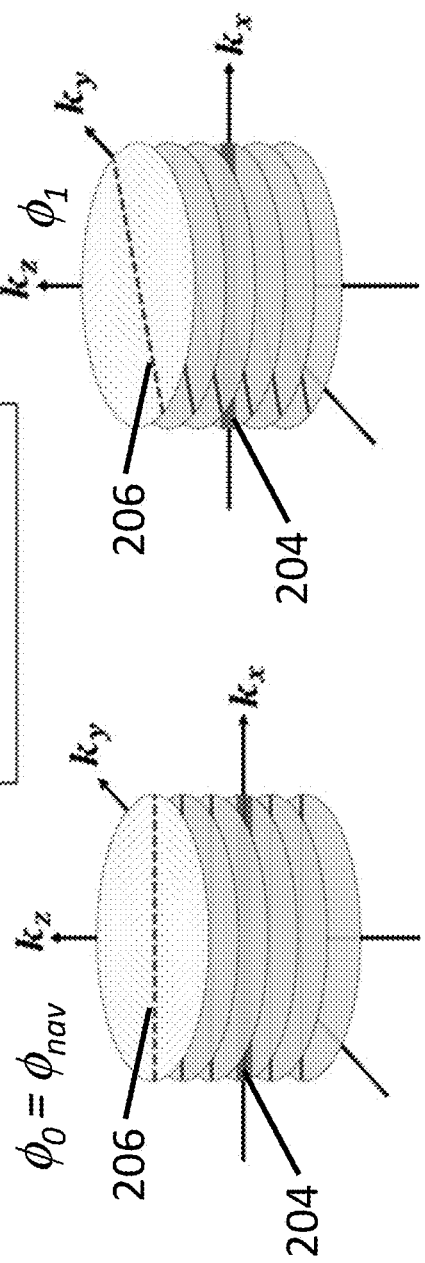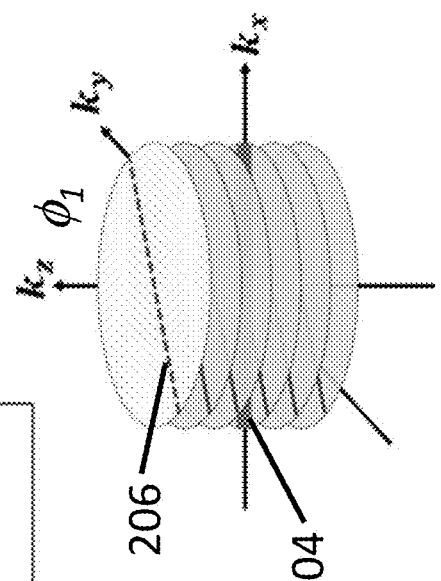
FIG. 2A    FIG. 2B    FIG. 2C    FIG. 2D

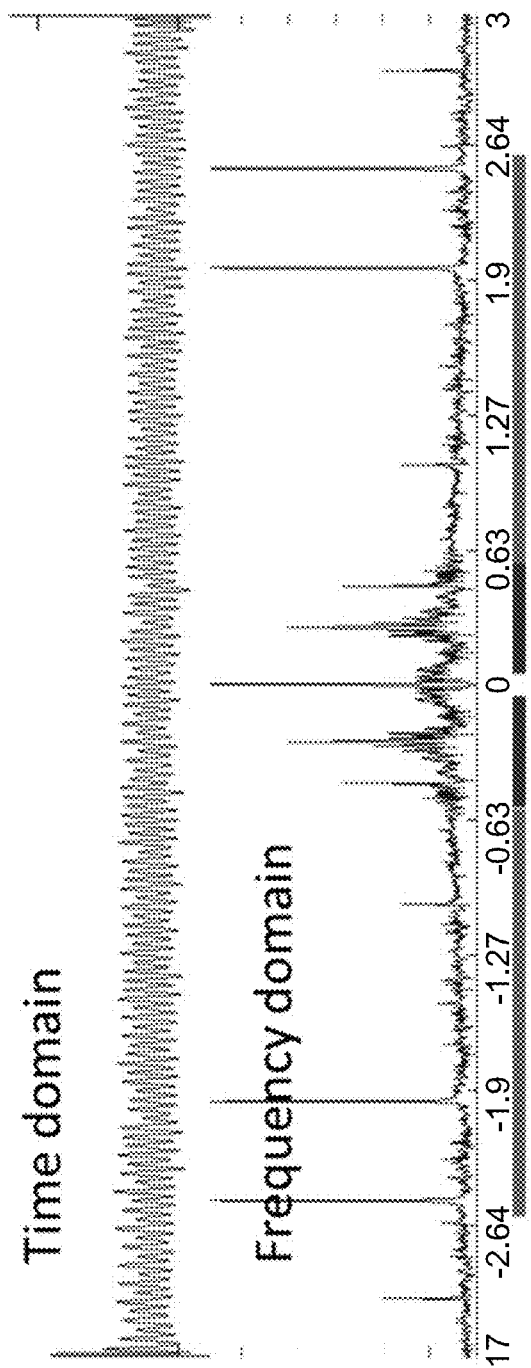
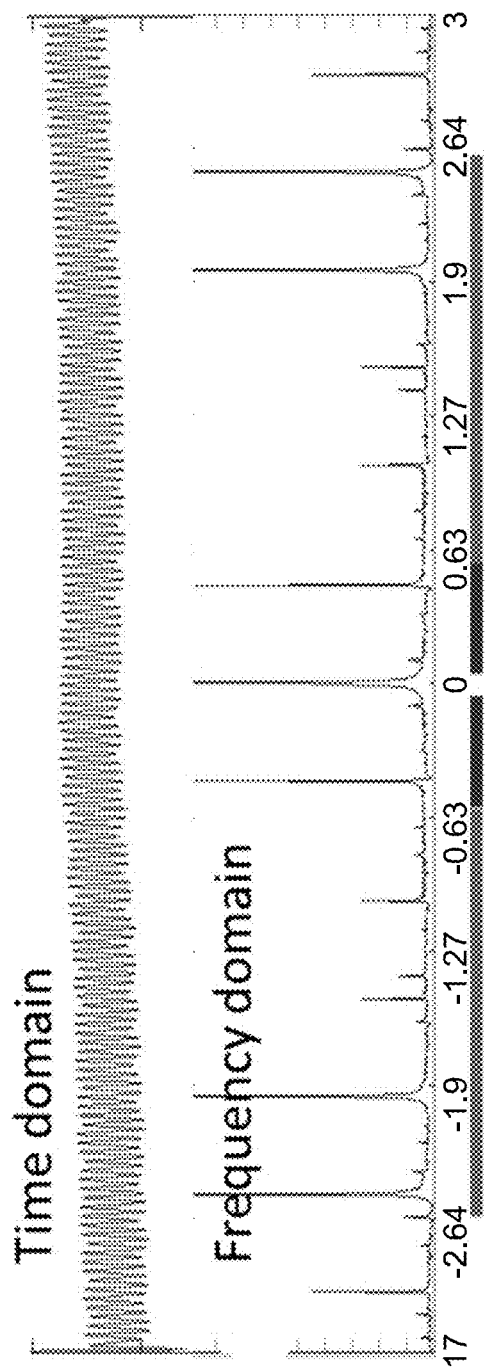
FIG. 3A  FIG. 3B  FIG. 3C  FIG. 3D

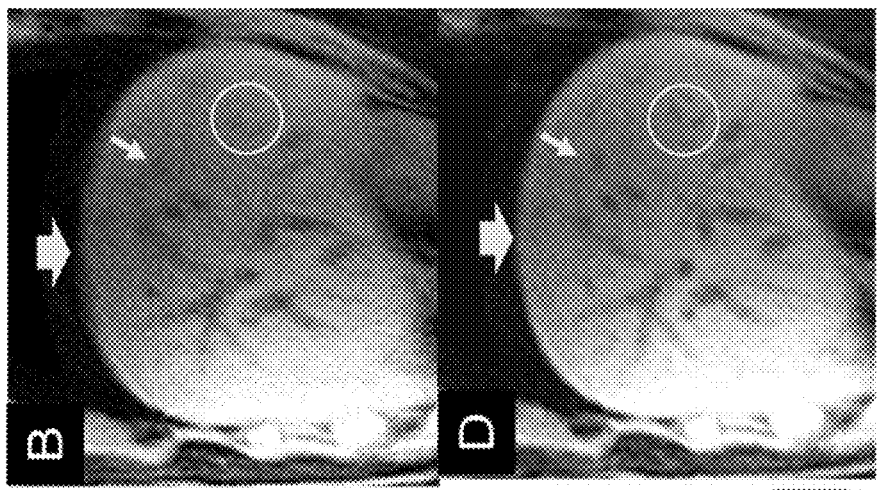
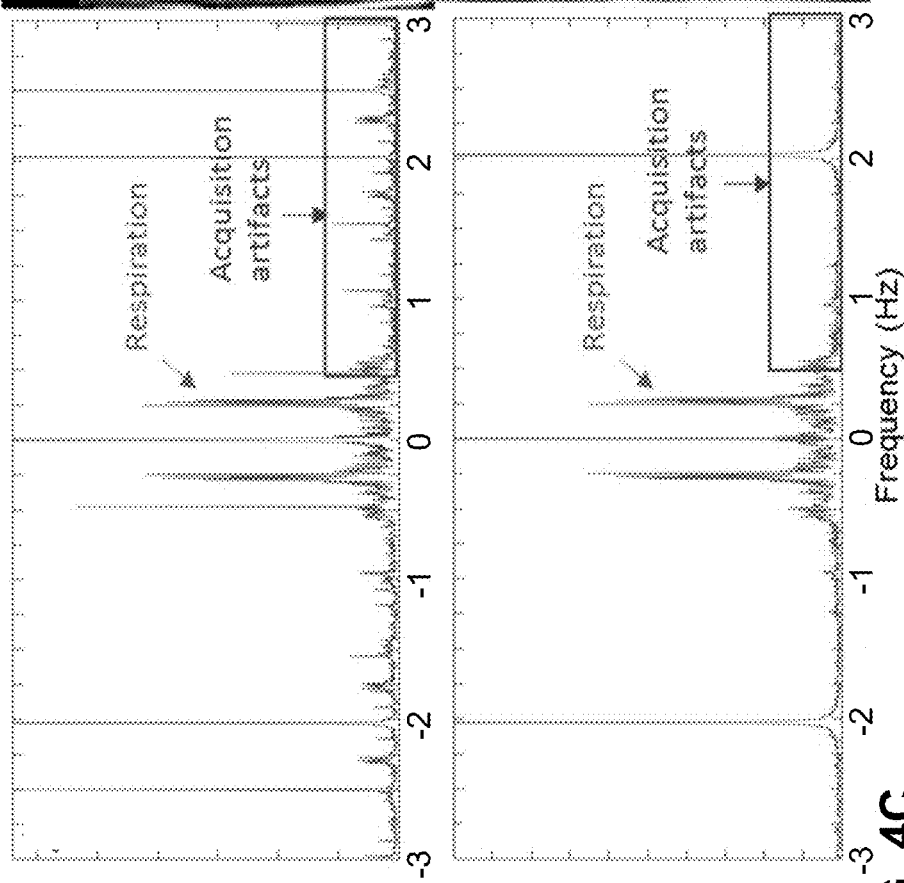
FIG. 4A  FIG. 4B  FIG. 4C  FIG. 4D

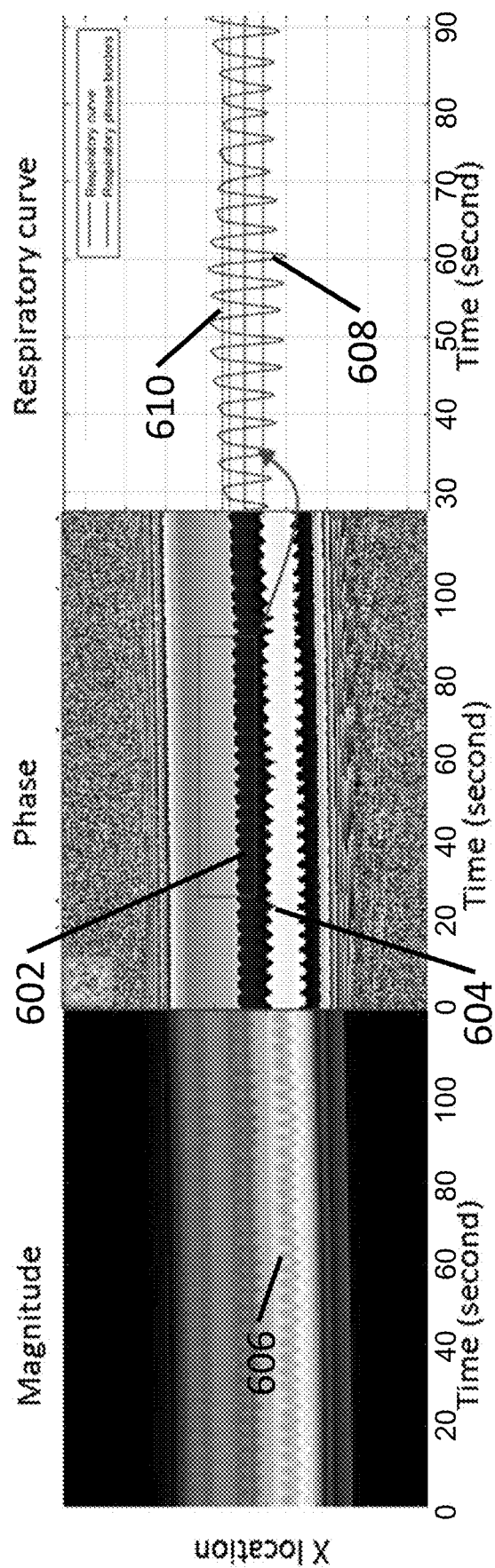

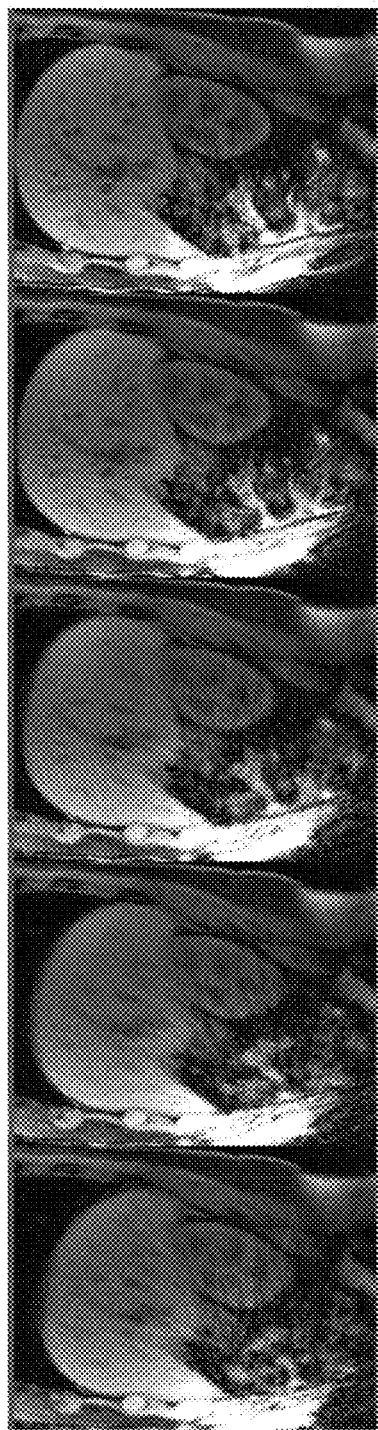
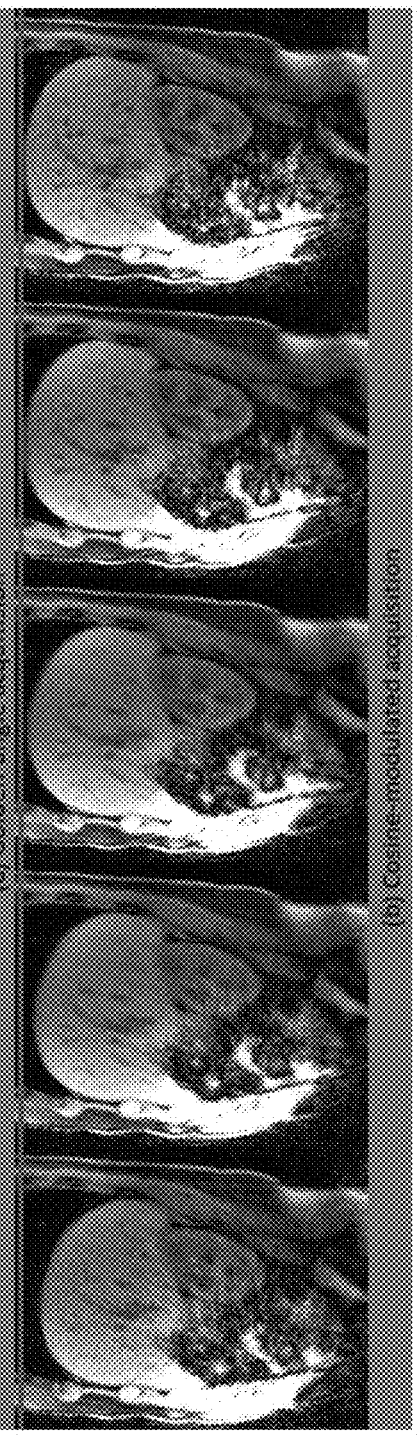
FIG. 10A
FIG. 10B

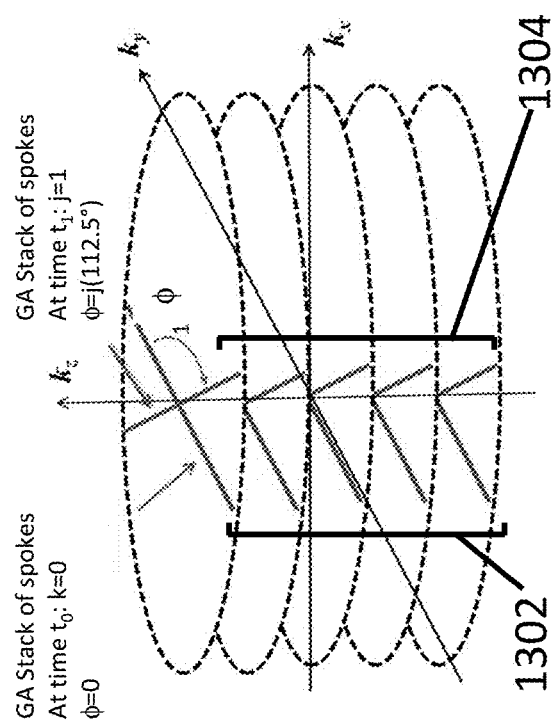
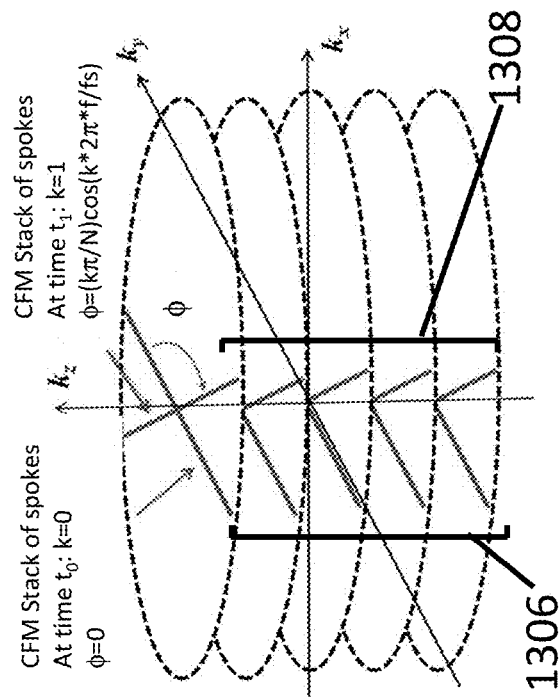
FIG. 13B
FIG. 13A

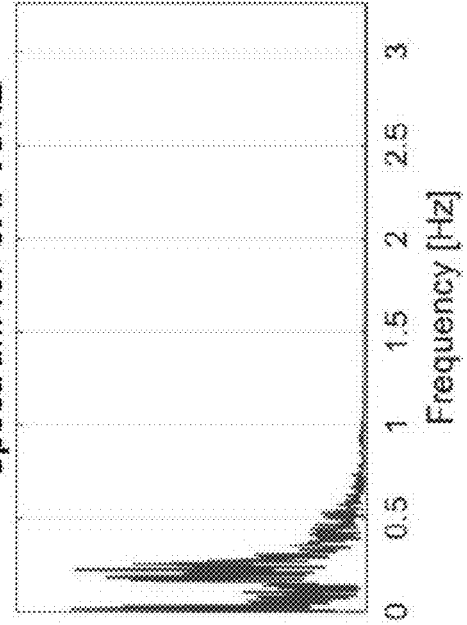
FIG. 35C
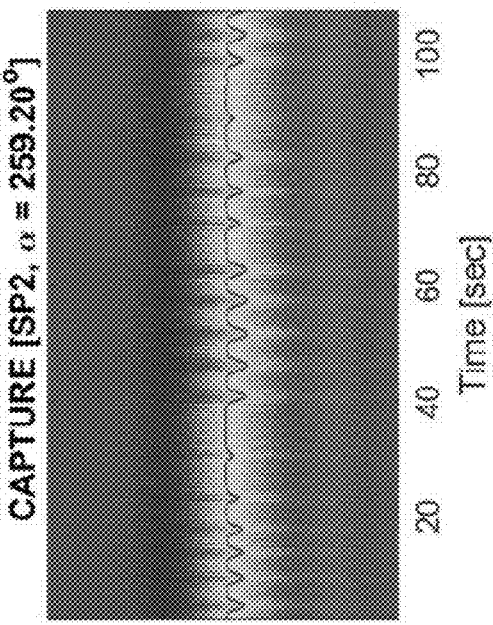
FIG. 35A
FIG. 35D
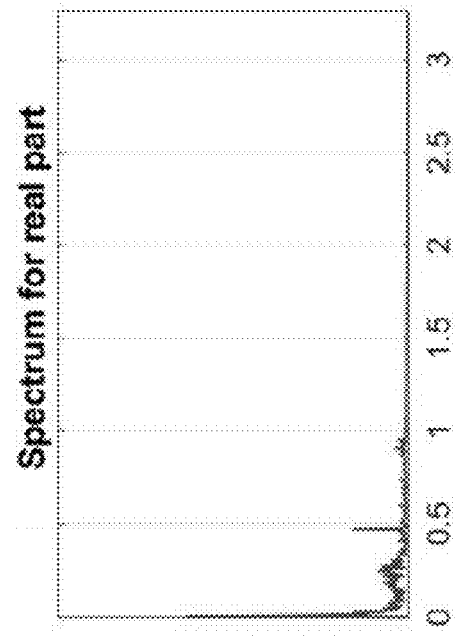
FIG. 35B

FREE-BREATHING AND SELF-NAVIGATED MRI METHOD FOR DEFORMABLE MOTION DERIVATION

CROSS-REFERENCE TO RELATED APPLICATION

This application claims the benefit of U.S. Provisional Application No. 62/446,193 filed Jan. 13, 2017, which is incorporated herein in its entirety.

BACKGROUND

The field of the disclosure relates generally to magnetic resonance (MR) imaging and, more particularly, to free-breathing, self-navigated MR imaging with motion resolution.

Lung cancer is a leading cause of cancer-related mortality, and non-small cell lung carcinoma (NSCLC) accounts for a large proportion of lung cancer cases. The diagnosis and treatment of lung cancer remains an on-going challenge, and imaging plays a key role in determining tumor extent and further enables internal imaging useful in triaging patients to primary surgery, locoregional radiation therapy, and/or chemotherapy. Based on medical image data and derived diagnostic parameters such as tumor volumes, tumor boundaries, and tumor staging information, various treatments such as resection (i.e. surgical removal), radiation therapy and/or chemotherapy may be indicated. Radiation therapy is typically prescribed based on medical image data to provide personalized treatment plans for individual patients.

Although the current imaging standard of care consists of diagnostic chest CT and positron emission tomography/computed tomography (PET/CT) with [$^{18}$F]fluorodeoxyglucose (FDG), recent advances in magnetic resonance imaging (MRI) have shown promise in providing accurate staging and treatment planning information. For example, advanced MR imaging techniques, including diffusion weighted imaging (DWI), may be used for staging lung carcinoma using more than just size criteria, and MR imaging may be beneficial in discriminating tumor tissue from adjacent collapsed lung for radiation therapy planning. MR imaging has also been incorporated into MRI-guided linear accelerators used for the delivery of radiation therapy. The improved visualization of lung carcinoma using MR imaging potentially enables more precise radiation treatment protocols with smaller targets and lower radiation doses to surrounding healthy heart, spinal cord, and lung tissues.

Respiratory and cardiac motion over the course of MR data acquisition sequences causes artifacts and blurring in four dimensional (4D) MR images, thereby reducing the effectiveness of MR imaging. Small tumors and metastases within a lung may shift position up to 2 cm during normal respiration. The degree of uncertainty induced by these motions may impact the scope of individualized radiotherapy treatment planning which relies on tissue volumes derived from imaging data to produce adequate tumor control (i.e. sufficient radiation coverage of the tumor allowing for margins and motion). Accurate knowledge of tumor characteristics, location and motion enable an escalated dose targeting only at the tumor region to augment treatment effect while still minimizing treatment toxicity to the surrounding tissue. Further, the motion effects on MR imaging may reduce the potential benefits of advanced medical imaging methods that combine MR with other imaging modalities, such as simultaneous PET/MR imaging.

Breath-holding, respiratory triggers, and navigator MR data acquisition schemes have been used in previous MR imaging methods to address the issue of motion-induced blurring and other image artifacts. However, breath-holding acquisition schemes limit the acquisition time to only tens of seconds per breath hold. Imaging coverage and spatial resolution are often traded off in exchange for a required short acquisition time by breath-holding acquisition. Moreover, the breath-holding method is challenging for some patients who have difficulty in holding their breath.

Respiratory-triggered methods make use of an externally-measured surrogate respiratory signal detected by an additional external sensor, such as respiratory bellows, placed on the patient' chest or abdomen to selectively capture image data at predetermined phases within a respiratory cycle (for example, near the end of respiratory expiration). However, the surrogate respiratory signal may differ depending on where the bellows or other additional sensor is placed on the surface of the body. Moreover, the bellows signal may also be contaminated by respiratory drift.

Navigator scans, which are typically interleaved with the actual imaging scan, have also been proposed for tracking patient motion during MR data acquisition. A navigator such as a pencil beam navigator, selectively images a small region within the k-space to track respiration-induced diaphragm position changes during free breathing. However, existing navigator schemes have at least several drawbacks, including complex sequence implementation, lengthened MR data acquisition time, and magnetization disturbances during the MR imaging scan. Motion correction of PET imaging data may rely on the modeling of changes in the target anatomy through the scanning period using PET data, and may be complex to implement due to the deformable nature of organs within the target anatomy.

Reliable, flexible, efficient and accurate MR motion resolution techniques would enhance the image of lung and heart tissues, and would consequently enhance the quality of treatment of diseases, such as lung cancer, by improving diagnostic and treatment planning imaging. In addition, these MR motion resolution techniques may have a beneficial impact on other clinical applications.

BRIEF DESCRIPTION OF THE INVENTION

In one aspect, a system for producing motion-corrected MR images of at least a portion of a patient is provided. The system includes an MRI scanner that includes a plurality of coils configured to detect a plurality of MR imaging datasets. Each MR imaging dataset includes a plurality of MR signals detected by one coil of the plurality of coils. The system further includes a controller operatively coupled to the MRI scanner. The controller includes at least one processor and a non-volatile memory. The controller further includes a current control unit and a pulse control unit that are operatively coupled to the MRI scanner. The current control unit and the pulse control unit are configured to operate the MRI scanner to detect the plurality of MR imaging signals according to a 1D navigator imaging sequence. The controller also includes an image processing unit operatively coupled to the MRI scanner that is configured to: receive the plurality of MR imaging datasets associated with the plurality of coils; identify a motion cycle using an automated motion detection method, in which the motion cycle includes a plurality of phases. The image processing unit is further configured to partition the plurality of MR imaging datasets into a plurality of image groups, each image group comprising a portion of the plurality of MR imaging datasets associated with one of the phases of the motion cycle.

A method for producing motion-corrected MR images of at least a portion of a patient, is provided. The method includes operating an MRI scanner having a plurality of coils according to a 1D navigator imaging sequence to detect a plurality of MR imaging datasets. Each MR imaging dataset includes a plurality of MR signals detected by one coil of the plurality of coils. The method also includes receiving the plurality of MR imaging datasets associated with the plurality of coils; identifying a motion cycle with a plurality of phases using an automated motion detection method, and partitioning the plurality of MR imaging datasets into a plurality of image groups, each image group comprising a portion of the plurality of MR imaging datasets associated with one of the phases of the motion cycle.

In another aspect, a method for performing free-breathing, self-navigated magnetic resonance imaging of a subject according to a 1D navigator motion resolution scheme is also provided. The method includes acquiring N sets of radial samples of MR imaging data. Each set of the N sets of radial samples includes a plurality of radial samples and one 1D navigator sample. Each radial sample and each 1D navigator sample is defined within one of a plurality of $k_x$-$k_y$ planes distributed along a $k_z$ axis of a k-space, and each radial sample within one set of radial samples is obtained at a unique azimuthal angle $\phi_j$ defined within the one $k_x$-$k_y$ plane where j is an integer value ranging from 0 to (N−1) and N ranges from about 500 to about 5000. Each 1D navigator sample within one set of radial samples is obtained at a predetermined navigator azimuthal angle $\phi_{nav}$ defined within the one $k_x$-$k_y$ plane. All radial samples and each 1D navigator sample within one set of radial samples are acquired before acquiring a subsequent set of radial samples. The method further includes constructing a motion cycle associated with the subject by analyzing a conflated set of inverse Fourier transforms of each 1D navigator sample from each of the N sets of radial samples, and identifying at least two motion phases, where each motion phase is a subset of the motion cycle. The method further includes grouping the N sets of radial samples into at least two phase groups. Each phase group includes a subset of the N sets of radial samples that contain a 1D navigator sample associated with one phase of the motion cycle. The method further includes generating at least two MR images. Each MR image is reconstructed from one of the phase groups.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings illustrate various aspects of the disclosure.

FIG. 2A is a schematic diagram of a three dimensional (3D) stack-of-stars Golden Angle (GA) MR acquisition sequence in one aspect, illustrating an MR data scan acquired at an azimuth angle $\Phi_0$ corresponding to a time $t_0$.

FIG. 2B is a schematic diagram of the three dimensional (3D) stack-of-stars Golden Angle (GA) MR acquisition sequence illustrating a set of MR data acquired at an azimuth angle $\Phi_1$ corresponding to a time $t_1$ obtained by increasing the azimuth angle $\Phi_0$ shown in FIG. 2A by the "Golden Angle" of 111.25° in one aspect.

FIG. 2C is an schematic diagram of a three dimensional (3D) stack-of-stars 1D navigator MR acquisition sequence including a 1D navigator acquired at an azimuth angle $\Phi_0$ corresponding to a time $t_0$.

FIG. 2D is an schematic diagram of a three dimensional (3D) stack-of-stars 1D navigator MR acquisition sequence including a one dimensional navigator acquired at an azimuth angle $\Phi_1$ corresponding to a time $t_1$, in which a 1D navigator is additionally acquired at azimuth angle $\Phi_0$ at $k_z$=0.

FIG. 3A is a graph showing MR signal amplitude in the time domain acquired from a human subject using the three dimensional (3D) stack-of-stars Golden Angle (GA) MR acquisition sequence shown in FIG. 2A and FIG. 2B.

FIG. 3B is a frequency spectrum obtained using the MR signal data of FIG. 3A, with frequency ranges associated with cardiac and respiratory motion indicated by red and green bars, respectively.

FIG. 3C is a graph showing MR signal amplitude in the time domain acquired from a stationary MR phantom using the three dimensional (3D) stack-of-stars Golden Angle (GA) MR acquisition sequence shown in FIG. 2A and FIG. 2B.

FIG. 3D is a frequency spectrum obtained using the MR signal data of FIG. 3C, with frequency ranges associated with cardiac and respiratory motion indicated by red and green bars, respectively.

FIG. 4A is a frequency spectrum of MR data acquired using the three dimensional (3D) stack-of-stars Golden Angle (GA) MR acquisition sequence shown in FIG. 2A.

FIG. 4B is an MR image reconstructed using the MR signal data of FIG. 4A.

FIG. 4C a frequency spectrum of MR signal data acquired using the three dimensional (3D) stack-of-stars 1D navigator MR acquisition sequence shown in FIG. 2C.

FIG. 4D is an MR image reconstructed using the MR signal data of FIG. 4C.

FIG. 6A is a map of the magnitude of the inverse Fourier transform of the 1D navigator illustrated in FIG. 2B over the entire acquisition of the 3D MR data; the greyscale intensity of the pixels in each column represents the magnitude of the inverse Fourier transform at a single time along the length of the head-to-toe axis in a manner similar to the data graphed in FIG. 5C.

FIG. 6B is a map of the phase of the inverse Fourier transform of the 1D navigator illustrated in FIG. 2B over the entire acquisition of the 3D MR data; the greyscale intensity of the pixels in each column represents the phase of the inverse Fourier transform at a single time along the length of the head-to-toe axis.

FIG. 6C is a graph of a respiratory cycle derived from the phase data shown in FIG. 6B.

FIG. 10A is an example set of 3D MR images generated using the GA sampling scheme.

FIG. 10B is an example set of 3D MR images generated using the CFM sampling scheme shown in FIG. 8.

FIG. 13A is a schematic illustration of a Golden Angle (GA) stack of spokes sampling scheme.

FIG. 13B is a schematic illustration of a CFM sampling scheme.

FIG. 35A is an image of an $A_{i,m}$ map obtained by maximum detection on the real part of the complex projections without phase tuning.

FIG. 35B is a spectrum corresponding to the map of FIG. 35A.

FIG. 35C is an image of an $A_{i,m}$, map obtained by maximum detection on the real part of the phase-tuned complex projections.

FIG. 35D is a spectrum corresponding to the map of FIG. 35C.

DETAILED DESCRIPTION

Figure 1:
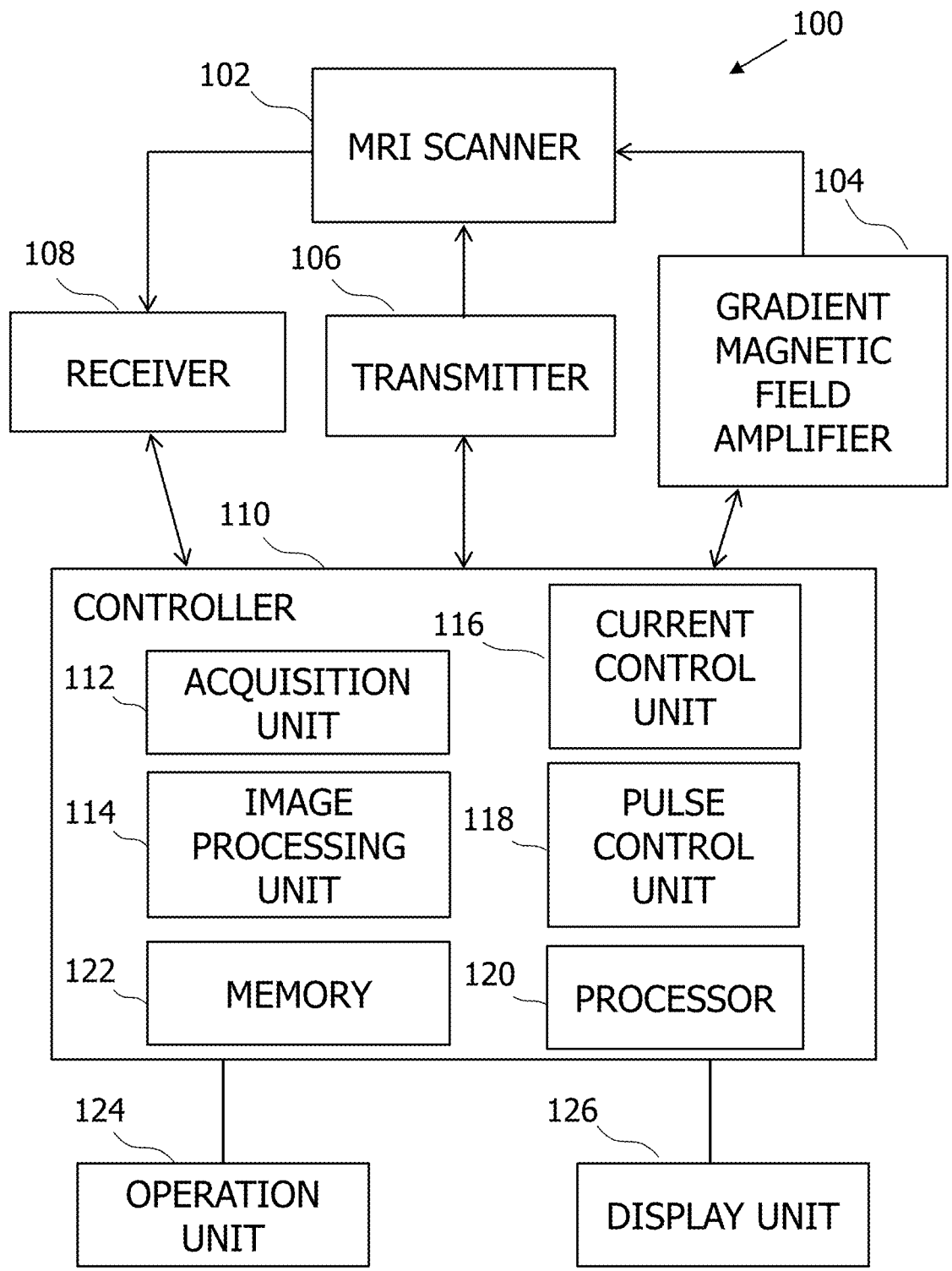
FIG. 1 is a block diagram illustrating the elements of a magnetic resonance imaging (MRI) system for generating MR images of an imaging volume in one aspect.

The systems and methods described herein relate to a free-breathing, self-navigated MR technique to obtain 4D MRI data for deformable motion resolution, enabling the production of motion-corrected MR images with high image quality compared to existing MRI motion compensation methods. In one aspect, MR imaging data are obtained using a 1D navigator imaging sequence. This sequence is a variant of the stack-of-stars sequence, in which a 1D navigator spoke defined along the $k_x$-axis (also referred to herein as "1D navigator") replaces the first spoke in each measured stack. Based on the projection-slice theorem, the inverse Fourier transform (FT) of each 1D navigator yields a projection of all transverse magnetization onto the x-axis, which is typically selected to be parallel to the axis of largest displacement associated with at least one motion cycle including, but not limited to, respiratory motion cycles and cardiac motion cycles. Because all 1D navigators are acquired at the same azimuthal angle (i.e. along the $k_x$-axis), the gradient delays associated with all 1D navigators are expected to be the same, thereby ameliorating at least one potential source of noise from the 1D navigator imaging sequence.

In various aspects, the 1D navigator imaging sequence is one of a variety of existing 3D image acquisition sequences that is modified to incorporate the acquisition of a 1D navigator at the beginning of each scan within the imaging sequence. The 1D navigator imaging sequence incorporates any 3D imaging sequence characterized by any k-space coverage scheme including, but not limited to, 3D stack of stars, 3D Cartesian, and 3D radial k-space coverage. In an additional aspect, the 1D navigator imaging sequence characterized by a 3D stack of stars k-space coverage is further characterized by an azimuthal sampling scheme including, but not limited to, a Golden Angle (GA) sampling scheme or a controlled frequency modulation (CFM) azimuth sampling scheme configured to displace the spectral content of MR signals associated with measurement artifacts to predetermined frequency ranges that are distinct from the frequency ranges associated with cardiac or respiratory motion cycles.

In another aspect, a method for automatically detecting motion cycles including, but not limited to, respiratory or cardiac processes includes concatenating the inverse FTs for all 1D navigators measured by each individual coil of the MRI scanner to form a plurality of navigator projection matrices $P_i$, where each $P_i$ corresponds to the $i^{th}$ coil of the MRI scanner used to detect MR signals during data acquisition. In another additional aspect, navigator projection matrices $P_i$ are subjected to a tuning process to identify an optimal coil and phase angle, and the motion cycle $r_{i,m}$ associated with the optimized coil and phase angle is identified as the optimized motion cycle that is used for subsequent binning of the 3D imaging data. The optimized coil and phase angle are identified according to a temporospectral quality metric that incorporates at least two quality factors including a relatively high proportion of MR signal spectral content within a frequency range associated with the desired motion cycles, and as relatively high peak-to-trough distance of the MR signals to enhance signal to noise ratio (SNR).

The systems and methods described herein overcome at least several limitations of existing systems and methods for obtain 4D MRI data for deformable motion resolution. The acquisition of 1D navigators at consistent positions within an imaging scan and within the k-space substantially alleviates the effects of gradient system imperfections and hence provides 'cleaner' signals, obviating the need for heavy filtering or complicated pattern recognition methods. Further, the tuned and robust motion cycle estimation method identifies the optimal complex projections of the 1D navigator from an optimal coil and phase angle identified by sampling the phase space for each coil of the MRI scanner.

As a result, each optimal coil and phase angle is customized for imaging dataset associated with each imaging subject, each position of the imaging subject within the MRI scanner, and various other parameters characterizing the MRI scanner including, but not limited to, the number and position of coils within the MRI scanner and the image acquisition sequence, thus enabling a robust and fully-automated method for motion signal detection, even in the presence of large inter-subject and inter-scan variations.

The systems and methods disclosed herein are configured to facilitate (i) improved MR signal clarity within a motion frequency range, (ii) improved image quality for MR images involving moving subjects, (iii) improved identification of motion phases, and/or (iv) multidirectional motion resolution for MR imaging. Although the motion cycles of the foregoing systems and methods are described with respect to respiratory and/or cardiac cycles, it is to be understood that other motion cycles within an imaging volume can be detected, measured, and imaged as described herein.

I. 1D Navigator Motion Resolution Method

Imaging of tissues subject to movements associated with cardiac and/or respiratory motion, such as non-small cell lung carcinoma (NSCLC) tissues, and the planning of treatments, such as surgical interventions and radiotherapy may be adversely affected by erroneous imaging data resulting from respiratory and/or cardiac motion. In various aspects, a 1D navigator motion resolution method is disclosed that is a modification of a motion resolution method associated with the stack of stars scanning methods described herein. In these various aspects, the acquisition of MR data associated with one of the data spokes in each stack of spokes is replaced by the acquisition of MR data associated with a 1D navigator spoke characterized by a position and azimuthal angle within the k-space that is equivalent for all stacks of spokes obtained during MR data acquisition, thereby providing a consistent reference measurement for each stack of spokes, thereby providing a means of associating each stack of spokes with a portion of a respiratory and/or cardiac cycle of a subject.

In one aspect, the 1D navigator motion resolution method enables self-navigated MR imaging, defined herein as a method of MR imaging, in which no external trigger or navigator imaging using separate radio frequency (RF) pulses and gradients are required to determine a motion phase associated with the acquired MR data. Without being limited to any particular theory, self-navigated MR imaging makes use of information extracted from the acquired MR imaging data to determine a motion phase associated with the acquired MR data. To enhance the effectiveness of any self-navigated MR imaging, the method of extracting information from the acquired MR data should incorporate features to reduce the confounding effects of magnetization history and spatial dependence of RF coil response.

Figure 32:
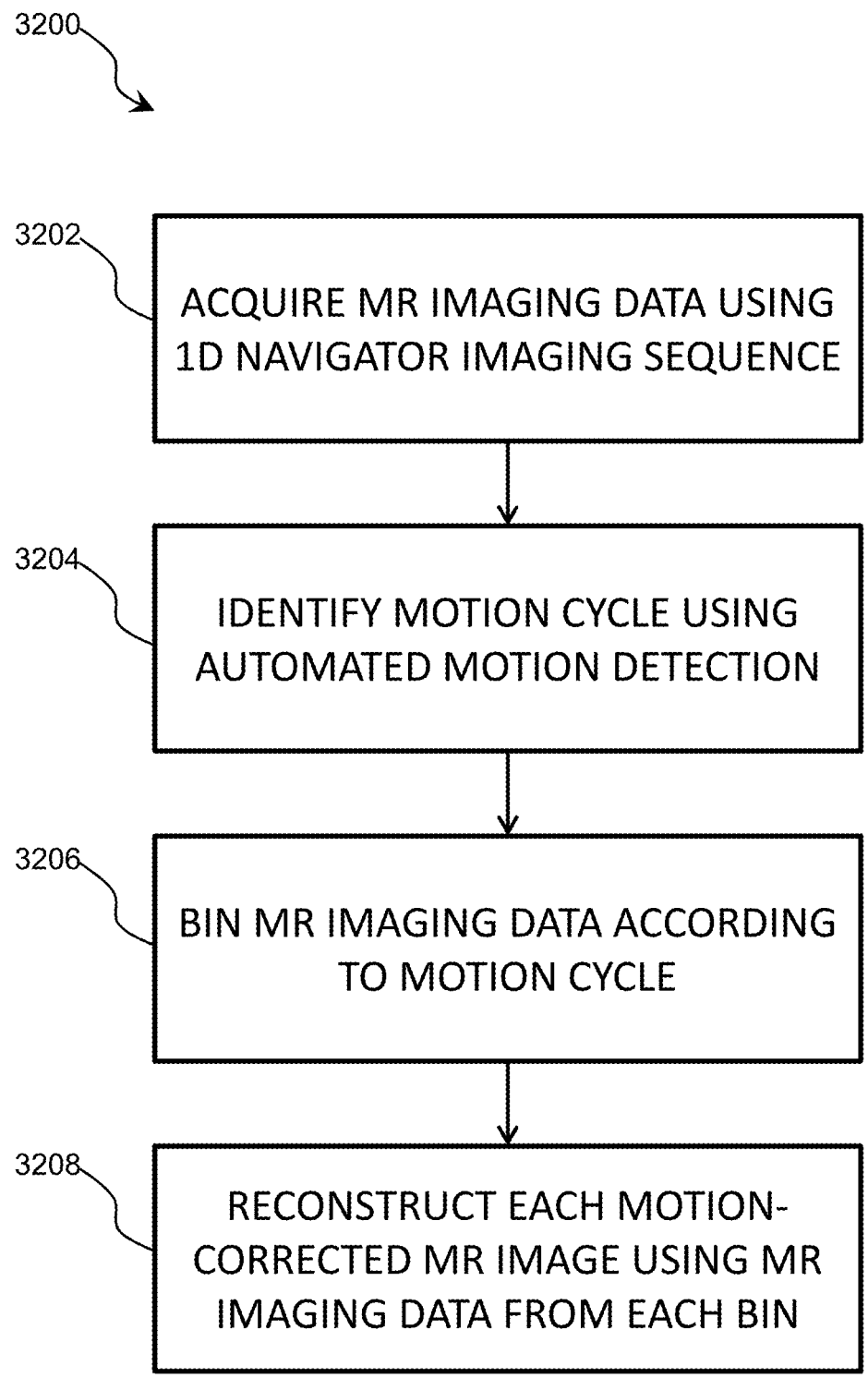
FIG. 32 is a flow chart illustrating a 1D Navigator Motion Resolution Method.

FIG. 32 is a flow chart illustrating the steps of a 1D navigator motion resolution method 3200 in one aspect. The method 3100 includes acquiring MR imaging data of a subject using a 1D navigator imaging sequence at 3102. As described in detail below, the 1D navigator imaging sequence includes obtaining MR imaging data for a 1D navigator aligned with the $k_x$ axis at the beginning of each scan, thereby providing a consistent reference measurement for each scan. In various aspects, the MR imaging data associated with each 1D navigator of each scan is associated with an index that is also associated with the remainder of the MR imaging data for that scan. This index is indicative of the elapsed time at which the MR imaging data was obtained for that scan.

Referring again to FIG. 32, the method 3200 further includes identifying a motion cycle of the subject using an automated motion detection method at 3204. As described in detail below, the automated detection method identifies an optimum coil and phase angle by processing by comparing motion cycles obtained from a plurality of complex projection matrices. Each complex projection matrix contain complex projections of all 1D navigators obtained by one of a plurality of coils of the MRI scanner deflected at one of a plurality of phase angles. The optimum coil and phase angle are identified according to a quality metric that includes a first factor configured to select motion cycles with frequency spectrum content that resides predominantly within the expect frequency range, and a second factor configured to select motion cycles with high peak-to-trough distances. In various aspects, the automated motion detection method enables fully-automated respiratory signal detection, even in the presence of large inter-subject and inter-scan variations.

Referring again to FIG. 32, the method 3200 further includes binning the MR imaging data at 3206 according to the motion cycle identified at 3204. As described in detail below, each bin contains MR imaging data associated with images obtained within a comparable portion of a motion cycle such as a respiratory cycle. All MR imaging data associated with a particular bin or portion of the motion cycle are combined and reconstructed into an MR image at 3208.

A. MR Scanning Using 1D Navigator Imaging Sequence

In various aspects, the 1D navigator imaging sequence may be a modification of an existing motion resolution method associated with a stack-of-stars data acquisition scheme. FIG. 2A illustrates a stack of spokes in k-space obtained at a first azimuthal angle $\phi_0$ and FIG. 2B illustrates a second stack of spokes in k-space obtained at a second azimuthal angle $\phi_1$ according to the existing stack-of-stars data acquisition scheme. As described previously herein above, the data acquired in each stack of spokes is frequency data associated with an imaging volume. For each stack of spokes obtained as illustrated in FIG. 2A and FIG. 2B, the k-space center 202 located at the origin of the k-space axes ($k_x=k_y=k_z=0$) is obtained. In the existing motion resolution method associated with the stack-of-stars data acquisition scheme, the k-space center 202 is typically used as a reference point associated with each stack of spokes to identify and resolve motion of the subject during MR imaging.

Without being limited to any particular theory, the MR signal variations across different azimuthal angles at the k-space center 202 are assumed to be caused by respiratory motion or other physiological motion, since all MR signal data obtained at the k-space center 202 for each azimuthal angle $\phi_i$ should be essentially identical for a stationary subject. However, due to gradient system imperfections including, but not limited to, gradient delay, eddy current, and/or off-resonance effects, the k-space center 202 prescribed in the pulse sequence is often shifted away from its presumed location. Furthermore, this offset of the k-space center varies between different stacks of spokes due to the different gradient waveforms applied in producing the different azimuthal angles for each stack of spokes within the k-space. As a result, the 'point' navigator of this existing method can generate artificial respiration-like signal variations even from a stationary phantom.

In various aspects, a 1D navigator imaging sequence is used to obtain MR imaging data, as illustrated in FIG. 2C and FIG. 2D. FIG. 2C illustrates a stack of spokes in k-space obtained at a first azimuthal angle $\phi_0$ and FIG. 2D illustrates a second stack of spokes in k-space obtained at a second azimuthal angle $\phi_1$ according to the 1D navigator imaging sequence in one aspect. The 1D navigator acquisition scheme obtains an embedded, 1D navigator spoke 204 for each stack of spokes. In this scheme, a first spoke 206 in each stack of spokes is skipped and replaced by the navigator spoke 204 (see FIG. 2C and FIG. 2D). Although the azimuthal angle $\phi_j$ changes from one stack of spokes to the next, a navigator angle $\phi_{nav}$ associated with the navigator spoke 204 is kept constant across all stacks of spokes. Since the same gradient waveforms are used to generate a constant navigator angle $\phi_{nav}$, any associated gradient delays or eddy current effects are unchanged for the 1D navigator spoke 204 from stack to stack, yielding a more standardized signal for motion detection than the point navigator of the existing motion resolution method.

Without being limited to any particular theory, the acquisition of a navigator spoke during acquisition of each stack of spokes at each azimuthal angle $\phi$ effectively adds an acquisition of spokes equivalent to the spokes at all azimuthal angles within a single $k_x$-$k_y$ plane. In various aspects, in order to preserve an overall data acquisition time that is comparable to an acquisition time of a comparable stack of spokes without obtaining a 1D navigator, the method may include skipping data acquisition for a single $k_x$-$k_y$ plane, as described herein above and illustrated in FIGS. 2C and 2D. In this aspect, any $k_x$-$k_y$ plane within the stack of spokes may be skipped without limitation. Without being limited to any particular theory, the $k_x$-$k_y$ planes positioned at the top or bottom of the stack of spokes (i.e. at the maximum and minimum values of $k_z$) are thought to contribute to the reconstructed image to a lesser degree compared to the data obtained at $k_x$-$k_y$ planes positioned near the center of the stack of spokes (i.e. $k_z$=0), and therefore may be skipped with minimal impact on image quality. In one aspect the method may include skipping data acquisition in the uppermost $k_x$-$k_y$ plane or the lowermost $k_x$-$k_y$ plane in the stack of spokes to maintain an acquisition time that is comparable to other the acquisition times of existing stack of spokes data acquisition schemes that do not obtain a 1D navigator spoke at each azimuthal angle $\phi$ of each stack of spokes.

In another aspect, the method may include obtaining the 1D navigator spoke at each azimuthal angle $\phi$ without skipping any of the other spokes at any $k_x$-$k_y$ plane. In this other aspect, the acquisition time is increased by the time needed to obtain the 1D navigator spoke during the acquisition of all other spokes at each azimuthal angle $\phi$. Without being limited to any particular theory, the acquisition time for the 1D navigator spoke may typically range from about 3 ms to about 4 ms and the overall data acquisition time may typically range from about 100 ms to about 200 ms. As a result, the additional time for acquiring the 1D navigation spoke as disclosed herein may increase the overall acquisition time by a relatively minor amount ranging from about 1% to about 4% of the overall acquisition time.

Referring again to FIG. 2C and FIG. 2D, the navigator angle $\phi_{nav}$ and an axis of the navigator spoke 204 (also referred to herein as a "navigator axis") is selected such that the navigator spoke 204 is aligned parallel to an axis of the imaging volume that has the largest motion. In one non-limiting example, to resolve respiratory motion of a patient, the navigator spoke 204 is oriented along a head-to-foot axis of the patient, also referred to herein as a superior-inferior (SI) axis. In another aspect, the navigator spoke 204 may selected to coincide with an x-axis (i.e., $k_y$=$k_z$=0) in the k-space such that the navigator angle $\phi_{nav}$ is zero. Although the axis of the navigator spoke 204 may be selected to align with the head-to-foot axis in some aspects, it is to be understood that the selected axis of the navigator spoke 204 may be oriented in any direction without limitation to facilitate motion resolution in any direction as needed. In the aspect illustrated in FIG. 2C and FIG. 2D, the navigator spoke 204 is acquired at $k_z$=0. In various other aspects, the navigator spoke 204 may be acquired at any non-zero $k_z$ value without limitation. In general, the 1D navigator spoke 204 may be flexibly selected along any orientation in the 3D k-space independently from the imaging orientation by applying a gradient rotational matrix just to the 1D navigator 204 to enable enhanced sensitivity in motion resolution.

In various aspects, more than one 1D navigator spoke defined along different orientations may be used to provide multiple-dimensional motion resolution in MR images. In another aspect, one or more additional navigator spokes (not illustrated) may be defined for use during acquisition to facilitate motion resolution in one or more additional directions. In one aspect, a first navigator spoke 204 may be defined to resolve respiratory motion while an additional navigator spoke may be defined to facilitate resolution of cardiac motion. It is to be noted that the additional 1D navigator spoke oriented along another non-collinear orientation may be included with minimal impact on the overall short scanning time. In this aspect, the use of a navigator spoke 204 and an additional navigator spoke may enable 2-D motion resolution. By way of non-limiting example, 2-D motion resolution may include simultaneous respiratory and cardiac motion resolution for heart imaging. In various aspects, one or more 1D navigator spokes may be obtained for each MR data scan associated with a stack of spokes with minimal impact on overall acquisition time, because acquisition time (TR) of a single 1D navigator spoke per stack of spokes typically takes approximately 3-4 ms out of about 100-200 ms for the entire stack of spokes. Since no additional RF pulses are needed to use the 1D navigator spoke, there is no signal interference among the navigator and imaging spokes.

In various aspects, since the 1D navigator spoke 204 needs no additional RF excitation, no artifacts associated with differences in magnetization disturbance result from the inclusion of the one or more 1D navigator spokes. In general, the 1D navigator motion resolution method as described herein may be incorporated into other 3D imaging sequences including, but not limited to, a 1D navigator data acquisition sequence characterized by a 3D stack of stars characterized by 3D Cartesian or radial k-space coverage.

In various aspects, the replacement of one of the spokes in each stack of spokes with the 1D navigator spoke for each azimuthal angle overcomes at least one or more limitations of previous navigator-based motion resolution methods. At least some existing navigator approaches to motion resolution in MR imaging make use of an additional navigator unit in an MRI system that uses separate radio frequency (RF) pulses and gradients to obtain a navigator for motion resolution, but these separate radio frequency (RF) pulses and gradients disturb the magnetization for the actual MR data scan and lengthens the total scan time. In various aspects, the navigator spoke 204 replaces a regular imaging spoke without need for additional RF pulses, and thus does not disturb the magnetization or lengthen the data acquisition time.

In various aspects, the 1D navigator imaging sequence further includes changing azimuth angle between successive stacks of spokes according to an azimuth sampling scheme selected from the group consisting of a Golden Angle (GA) azimuth sampling scheme and a controlled frequency modulation (CFM) sampling scheme.

FIG. 13A is a schematic illustration of an existing Golden Angle (GA) stack of spokes azimuth scanning scheme. Typically in any stack of spokes data acquisition scheme, radial sampling (depicted as a red or blue line) at a constant azimuthal angle ϕ for each radial sample is used to sample MR data within each $k_x$-$k_y$ plane, leading to star-like coverage for each $k_x$-$k_y$ plane after combined sampling along all spokes at all azimuthal angles ϕ$_i$. In the GA stack of spokes data acquisition scheme, Cartesian encoding is utilized along the $k_z$ direction to form a stack of these stars. As used herein, a spoke refers to MR imaging data collected along a specific direction and azimuthal angle within a kx-$k_y$ plane, typically including the $k_z$ axis (i.e. $k_x$=$k_y$=0).

Referring again to FIG. 13A, the 3D GA azimuth scanning scheme includes acquiring MR data along each stack of spokes for a plurality of stacks of spokes. Each stack of spokes is defined herein as a set of spokes at constant azimuth angles ϕ$_j$ acquired in succession along the $k_z$ axis for all $k_x$-$k_y$ planes. The Golden Angle azimuth sampling scheme is used to determine the azimuthal angle of each stack of spokes according to Equation (1) or Equation (2):

$$\phi_j = j*111.25° \quad \text{Equation (1)}$$

$$\phi_j = j*68.75° \quad \text{Equation (2)}$$

where j=0, 1 . . . N−1, with N being the total number of stacks of spokes to provide uniform radial sampling for sufficiently high N. In this acquisition scheme, one whole stack of spokes 1302 is acquired at a first azimuthal angle before proceeding to a second subsequent stack of spokes 1404 acquired at a second azimuthal angle. Referring to FIG. 13A, the first stack of spokes 1302 is acquired at ϕ=0, while the second subsequent stack 1304 is acquired at ϕ=111.25° (using Equation (1)). The "Golden Angle" as used herein, refers to the 111.25° (or) 68.75° azimuthal angular increment between two adjacent stack-of-spokes.

Without being limited to any particular theory, magnetization history (e.g., eddy currents) associated with the sequence of azimuthal angles ϕ$_j$ used to acquire MR imaging data according to an azimuth scanning scheme such as the Golden Angle (GA) scheme may introduce physiologically irrelevant signal variations that negatively impact MR image quality and may further act to confound respiratory motion resolution.

In one non-limiting example of the existing stack-of-spokes data acquisition scheme, the MR data acquired for a free-breathing subject and for a stationary phantom were obtained and compared. FIG. 3A is a graph of DC signals measured from the free-breathing patient as a function of time, and the frequency spectrum corresponding to the DC signals of FIG. 3A is shown in FIG. 3B. Referring again to FIG. 3B, DC signals falling within a frequency range of 0.1-0.5 Hz (red bars), and 0.5-2.5 Hz (green bars) were assumed to represent respiratory and cardiac motion, respectively. As illustrated in FIG. 3B, DC signal peaks were observed at signal frequencies falling well outside of expected physiological ranges. Typically, these DC signals characterized by signal frequencies falling outside of physiological ranges were considered to be artifacts resulting from the combination of respiratory or cardiac motion and the spatial dependence of coil sensitivity as discussed herein above.

It was unexpectedly discovered that the 3D GA stack-of-stars data acquisition scheme introduced similar signal artifacts even when imaging a stationary phantom. As a result, at least a portion of the artifacts typically observed in MR data obtained using the 3D GA stack-of-stars data acquisition scheme could not be attributed to the interaction of patient movements and spatial dependence of coil sensitivity. FIG. 3C is a graph of DC signals measured from a stationary phantom as a function of time, and the frequency spectrum corresponding to the DC signals of FIG. 3C is shown in FIG. 3D. Although no DC signal variations from the scan on a stationary phantom would be expected, the frequency spectrum of FIG. 3D includes DC signal variations falling both inside and outside of cardiac and respiratory ranges. Significantly, a comparison of the frequency spectrum of a breathing patient (FIG. 3B) and of a stationary phantom (FIG. 3D) are characterized by DC signal peaks falling within expected physiological ranges, indicating that DC signals associated with "pseudo-motion" was detected from the stationary phantom using the 3D GA stack-of-stars data acquisition scheme.

Without being limited to any particular theory, the spatial dependence of coil sensitivity and gradient system imperfections, such as gradient delay, eddy current, and off-resonance effects may shift the k-space center defined in the RF pulse sequence away from its presumed location. Furthermore, this k-space center offset may vary between different azimuthal angles of different stacks of spokes due to the different gradient waveforms applied to produce various azimuthal angles, causing the generation of artificial respiration-like signals even in a stationary phantom. As a result, 'pseudo-motion' may be detected from a stationary phantom using the Golden Angle radial acquisition scheme as illustrated in FIG. 3D.

In another aspect, the 1D navigator imaging sequence includes a controlled frequency modulation (CFM) azimuth sampling scheme to determine the azimuth angles of each stack of spokes. The controlled frequency modulation (CFM) azimuth sampling scheme is configured to: (i) reduce interference from physiologically irrelevant signal variations, and (ii) provide substantially uniform radial k-space coverage, thereby improving the quality of MR images reconstructed using the MR data and enhancing the accuracy of physiological motion determined from MR data obtained using the CFM sampling scheme.

In various aspects, a 3D controlled frequency modulation (CFM) azimuth sampling scheme is used to obtain MR data with minimal "pseudo-motion" artifacts. FIG. 13B is a schematic representation of the 3D CFM azimuth sampling scheme, and FIG. 13A is a schematic representation of a Golden Angle azimuth sampling scheme. In an aspect, the 3D CFM azimuth sampling scheme includes a stack of spokes data acquisition scheme in which radial sampling (depicted as a red or blue line) at a constant azimuthal angle ϕ for each radial sample is used to sample MR data within each $k_x$-$k_y$ plane, leading to star-like coverage for each $k_x$-$k_y$ plane after combined sampling along all stacks of spokes at all azimuthal angles ϕ$_n$. In a manner similar to the GA stack of spokes data acquisition scheme, Cartesian encoding may be utilized along the $k_z$ direction to form a stack of these stars in the 3D CFM azimuth sampling scheme in an aspect.

Referring again to FIG. 13B, the 3D CFM data acquisition scheme includes acquiring MR data along each stack of spokes for a plurality of stacks of spokes. Each stack of spokes is defined herein as a set of spokes at constant azimuth angles ϕ$_j$ acquired in succession along the $k_z$ axis for all $k_x$-$k_y$ planes. In an aspect, the 3D CFM sampling scheme determines each azimuthal angle of each stack of spokes according to Equation (3):

$$\phi_j = (j*180°/N)*\cos(j*180°) = (j*180°/N)*(-1)^j \quad \text{Equation (3)}$$

where j=0, 1 ... N−1 with N being the total number of stacks of spokes to provide uniform radial sampling for sufficiently high N. In an aspect, the first term of Equation (3), (j*180°/N), provides substantially uniform coverage between 0° and 180° for all stacks of spokes. The second term, cos(j*180°) (alternatively $(-1)^j$) introduces an alternating sign that expands the coverage of the stacks of spokes to (−180°, 180°), or, equivalently, to [0, 360°).

In another aspect, the 3D CFM sampling scheme determines each azimuthal angle of each stack of spokes according to Equation (4):

$$\phi_j = (j*180°/N)*\cos(j*2\pi*f/f_s)$$ Equation (4)

where f is a modulation frequency and $f_s$ is a sampling frequency. In one aspect, the modulation frequency may be defined to be half of the sampling frequency fs, thereby rendering Equation (4) equivalent to Equation (3). In an aspect, the 3D CFM sampling scheme may also be referred to as a "cosine-modulated sampling scheme" as used herein.

Referring again to FIG. 13B, the 3D CFM sampling scheme includes acquiring one whole stack of spokes 1306 at a first azimuthal angle and then proceeding to a second azimuthal angle to acquire a second subsequent stack of spokes 1308. The first stack of spokes 1306 is acquired at φ=0, while the second subsequent stack 1308 is acquired at an azimuthal angle determined by Equation (3) or Equation (4). In this aspect, azimuthal angle associated with each stack of spokes is determined by Equation (3) or Equation (4), rather than adding a constant increment as described in the GA data acquisition method herein above.

In various aspects, all spokes in a given stack of spokes are assumed to be acquired at essentially the same phase in the respiratory cycle due to the relatively short acquisition time for a stack of spokes relative to the characteristic period of a cardiac and/or respiratory cycle. The typical acquisition time ($T_S$) for each stack-of-spokes is approximately $Nz \times T_R$ and usually ranges from about 100 ms to about 200 ms; Nz refers to the number of $k_x$-$k_y$ planes defined within the k-space and $T_R$ refers to the time to acquire MR data along a single spoke. Because respiratory and cardiac motions are typically slower than the acquisition time ($T_S$) for each stack-of-spokes, it is assumed that all spokes in the same stack-of-spokes share the same body 'pose' or position in a respiratory or cardiac cycle.

In this stack-of-stars acquisition, the K-space center ($k_x$=$k_y$=$k_z$=0) is sampled by every stack-of-spokes. In the stack of stars acquisition scheme, the MR signal detected at this K-space center across different azimuth angles (i.e. different spokes within the same $k_x$-$k_y$ plane) is assumed to be the same in the absence of motion. However, due to the spatial dependence of coil sensitivity, the position change of organs due to respiratory and cardiac motions can lead to DC signal variations in a few coils. This spatial dependence may manifest itself as DC signals that are not related to physiological motion that may occur at frequencies both inside of and outside of expected physiological ranges. In addition, because the full range of azimuthal angle φj is [0, 360°), the two widely utilized Golden Angle scanning schemes (see Equations (1) and (2)) begin to almost repeat themselves, inducing multiple large and small pseudo-periodicities.

In various aspects, the number of stacks of spokes N may be selected to provide sufficient radial coverage over the extent of the field of view within each $k_x$-$k_y$ plane so as to enable a desired MR image resolution. Without being limited to any particular theory, the selection of the number of stacks of spokes N may be influenced by any one or more of at least several factors including, but not limited to: the imaging field of view (FOV), spatial resolution of the image, and acquisition time of the imaging data. Without being limited to any particular theory, the selected number of stacks of spokes may balance at least two factors including, but not limited to: i) the enhanced MR image resolution enabled by a higher N; and ii) the shorter overall data acquisition time enabled by a lower N. In one aspect, the number of stacks of spokes (N) may range from about 500 to about 5000. In various other aspects, the number of stacks of spokes (N) may range from about 500 to about 1000, from about 750 to about 1250, from about 1000 to about 1500, from about 1250 to about 1750, from about 1500 to about 2500, from about 2000 to about 3000, from about 2500 to about 3500, from about 3000 to about 4000, from about 3500 to about 4500, and from about 4000 to about 5000. In yet another aspect, the number of stacks of spokes (N) may be about 2000.

Figure 9B:
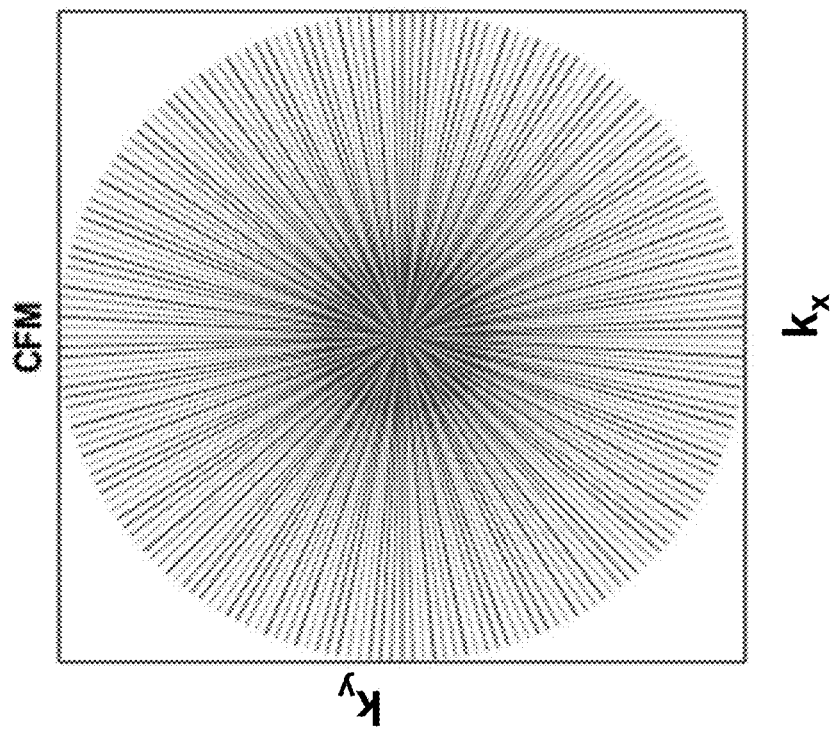
FIG. 9B is a graph of the data acquisition spokes specified using the CFM sampling scheme as viewed in the $k_x$-$k_y$ plane; similarly colored spokes are associated with similar bins within the respiratory cycle.
Figure 9A:
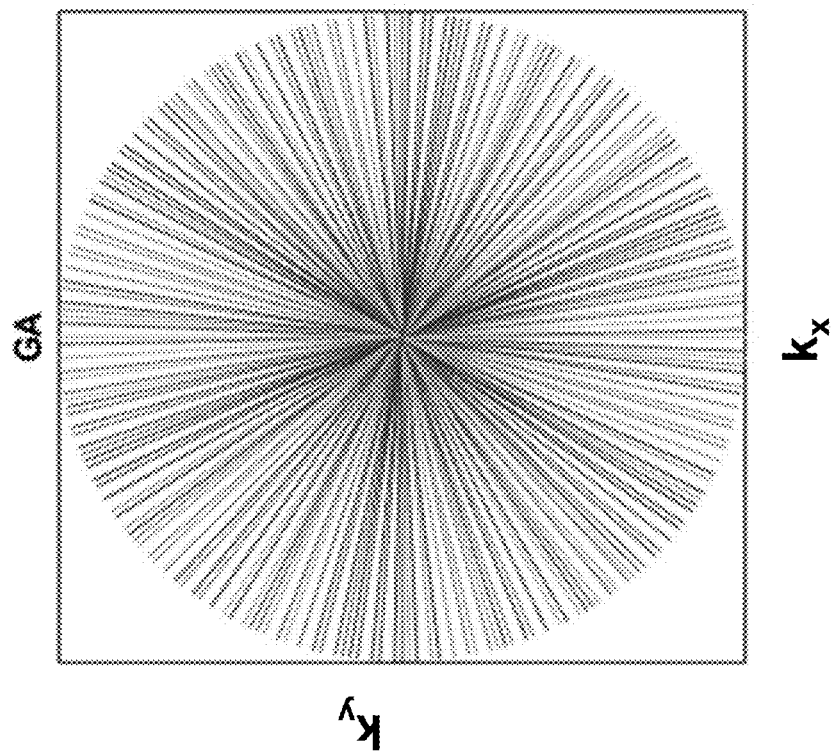
FIG. 9A is a graph of the data acquisition spokes specified using the GA sampling scheme as viewed in the $k_x$-$k_y$ plane, illustrating the radial k-space coverage; similarly colored spokes are associated with similar positions within the respiratory cycle.

FIG. 9A and FIG. 9B are schematic illustrations of the radial k-space coverage over the $k_x$-$k_y$ plane of the GA sampling scheme and the CFM sampling scheme, respectively, for about 2000 stacks of spokes (N≈2000). Comparing FIG. 9A to FIG. 9B, the CFM sampling scheme achieves comparable radial k-space coverage to the GA sampling scheme, and further facilitates substantially uniform MR data acquisition. Without being limited to any particular theory, the distribution of spokes specified by the GA sampling scheme illustrated in FIG. 9A is characterized by an angular increment between spokes defined at adjacent scans that is much larger than the comparable angular increments between adjacent spokes specified by the CFM sampling scheme illustrated in FIG. 9B. As a result, the radial k-space coverage over the $k_x$-$k_y$ plane of the GA sampling scheme is likely to be more complete and uniform for a partial dataset resulting from an interrupted imaging session as compared to the corresponding radial k-space coverage of the CFM sampling scheme for a partial dataset.

Figure 8:
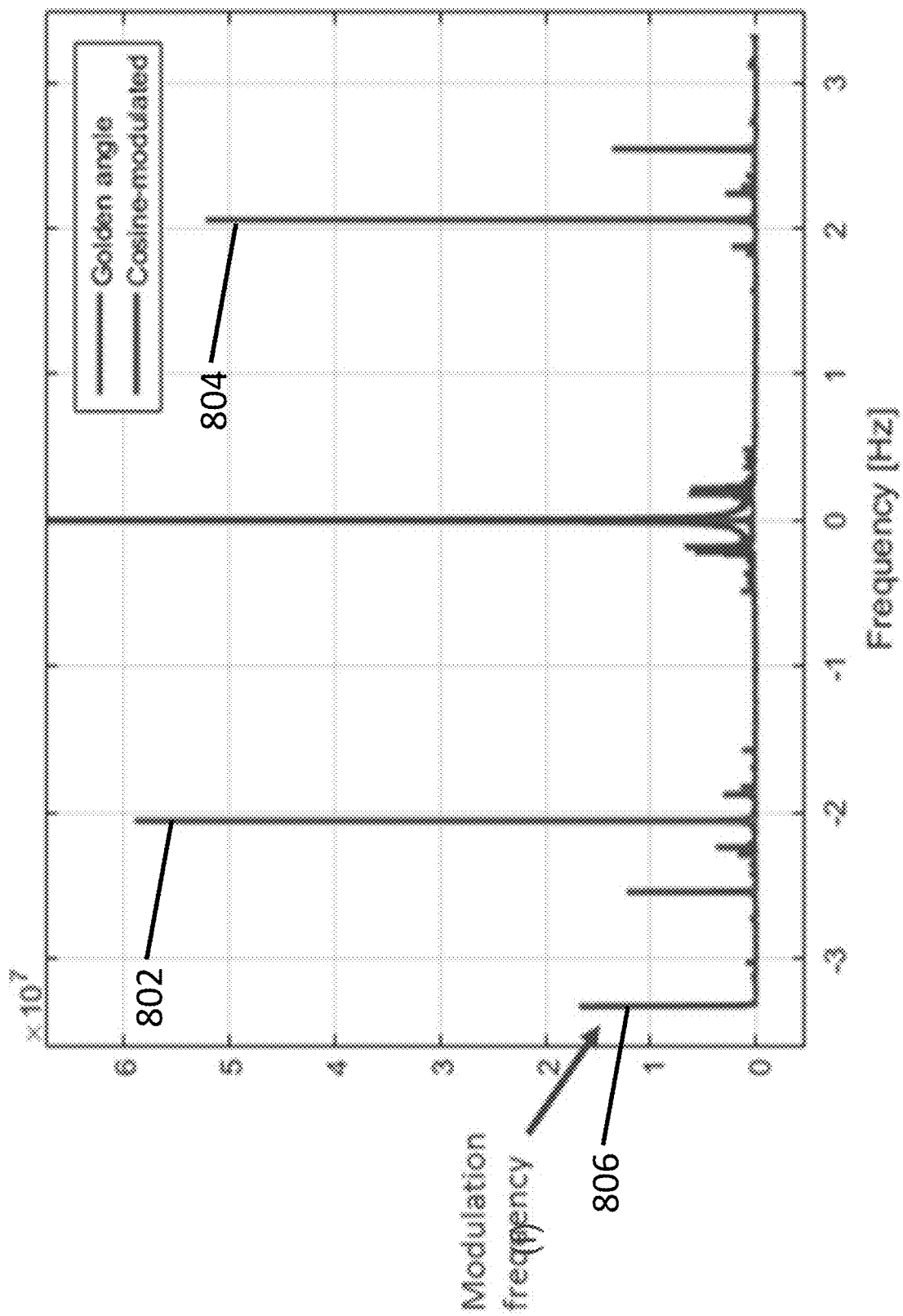
FIG. 8 is a graph comparing a first (blue) frequency spectrum of MR imaging data obtained from a subject using a Golden Angle (GA) sampling scheme to a second (red) frequency spectrum of MR imaging data obtained from a subject using a controlled frequency modulation (CFM) sampling scheme.

FIG. 8 is a frequency spectrum graph comparing the Fourier-transformed MR signals sampled by a 3D GA stack-of-stars data acquisition scheme (blue line) to Fourier-transformed MR signals sampled by the CFM data acquisition scheme for a normal subject. Referring to FIG. 8, the 3D GA stack-of-spokes data acquisition scheme induces physiologically irrelevant frequency components, such as peaks 802, 804. These peaks 802, 804 can also be present within frequency ranges typical of physiological movements, including a frequency ranging from about −2.5 Hz to about +2.5 Hz associated with respiratory motion (0.1-0.5 Hz) and/or cardiac motion (0.5-2.5 Hz). These introduced artifacts may be difficult to distinguish from legitimate motion-based frequency signatures (see FIG. 3D). The CFM sampling scheme generates a frequency peak 806 associated with acquisition-induced signal variations at the modulation frequency, but the motion frequency range is substantially free of physiologically irrelevant frequency components. The remaining frequency peaks within the physiological range is assumed to be indicative of motion within the imaging volume. In an aspect, the position of this frequency peak 806 may be modulated by adjustment of the modulation frequency (f) factor in Equation (4).

In various aspects, the modulation frequency f may be specified to be any frequency value sufficiently distinct from the expected physiological frequency range so as to enable separation of the physiologically irrelevant frequency components from those frequency components associated with respiratory and/or cardiac motion. In one aspect, if the field of view (FOV) of MR imaging includes tissues subject to movement associated solely with respiratory movements, the modulation frequency f may be specified to be any value greater than about 0.5 Hz. In another aspect, if the field of view (FOV) of MR imaging includes tissues subject to movement associated solely with cardiac movements, the modulation frequency f may be specified to be any value greater than about 2.5 Hz. In various other aspects, the modulation frequency f may be specified to be any value greater than about 0.5 Hz, any value greater than about 0.6 Hz, any value greater than about 0.7 Hz, any value greater than about 0.8 Hz, any value greater than about 0.9 Hz, any value greater than about 1.0 Hz, any value greater than about 1.2 Hz, any value greater than about 1.4 Hz, any value greater than about 1.6 Hz, any value greater than about 1.8 Hz, any value greater than about 2.0 Hz, any value greater than about 2.5 Hz, any value greater than about 3.0 Hz, or any value greater than about 5 Hz or higher.

In contrast to the Golden Angle schemes described herein above, the CFM data acquisition scheme does not introduce physiologically irrelevant MR signals within the respiratory and cardiac frequency range. Instead, the CFM data acquisition scheme is configured to shift all acquisition-related frequency components of the MR signals (i.e., the physiologically irrelevant frequency components) to a region of the frequency spectrum that is distinctly separated from the MR signal frequency ranges associated with respiratory and cardiac motion. Accordingly, the MR data falling within the respiratory and cardiac frequency ranges may be used for motion resolution, and the physiologically irrelevant frequency components may be filtered from the acquire MR signal data. By way of non-limiting example, a low pass filter may be used to filter spectral content beyond 0.6 Hz to exclude the physiologically irrelevant frequency components prior to binning the remaining MR signal data based on the respiratory cycle.

In various aspects, the elimination of pseudo-periodicities in the MR signals obtained using the CFM sampling scheme may result in a reduction in MR image blurring. By way of non-limiting example, FIGS. 10A and 10B are sets of MR images reconstructed from MR data obtained using the 3D GA sampling scheme and the 3D CFM sampling scheme, respectively. Each set of MR images represents five respiratory phases of a respiratory cycle. Referring to FIG. 10A, the image set reconstructed from MR data obtained using the 3D GA sampling scheme includes blurred images due to the signal variations introduced during acquisition. However, referring to FIG. 10B, the physiologically irrelevant signal variations removed by use of the 3D CFM sampling scheme resulted in sharper MR images compared to the corresponding images of FIG. 10A.

B. Automated Detection of Motion Cycles Using 1D Navigator Imaging Data

In various aspects, the MR data associated with the 1D navigator spokes of each stack of spokes may be combined and used to resolve motion of the subject within the k-space during the MR scanning. The 1D navigator spoke associated with each stack of spokes provides a robust basis for motion resolution during MR imaging. Without being limited to any particular theory, the Fourier projection-slice theorem as applied to the 1D navigator method specifies that the inverse Fourier transform of the k-space frequency signals of the 1D navigator spoke 204 (see FIG. 2C) is equivalent to a projection of the whole imaging volume onto a line along a corresponding axis in the image domain. In one aspect, the inverse Fourier transform of the k-space frequency signals of the 1D navigator spoke may be used to determine a projection magnitude along the corresponding axis in image space, which corresponds to the x-axis using the relation expressed in Equation (5):

$$FT^{-1}\{\text{Navigator } k\text{-space data}\} = \iint I(x,y,z)\,dy\,dz \quad \text{Equation (5)}$$

where $I(x,y,z)$ is a spatial function of the imaging volume.

In one aspect, the inverse Fourier transforms of the 1D navigator k-space data associated with each MR data scan may be compared to identify any motion that may have occurred within the field of view during MR imaging. In various aspects, the inverse Fourier transform is a complex number with a real and imaginary portion associated with a signal magnitude and phase, respectively. In one aspect, the magnitudes of the inverse Fourier transforms of the 1D navigator data may be used to resolve any motion of the subject during MR scanning, as described herein below.

Figure 5C:
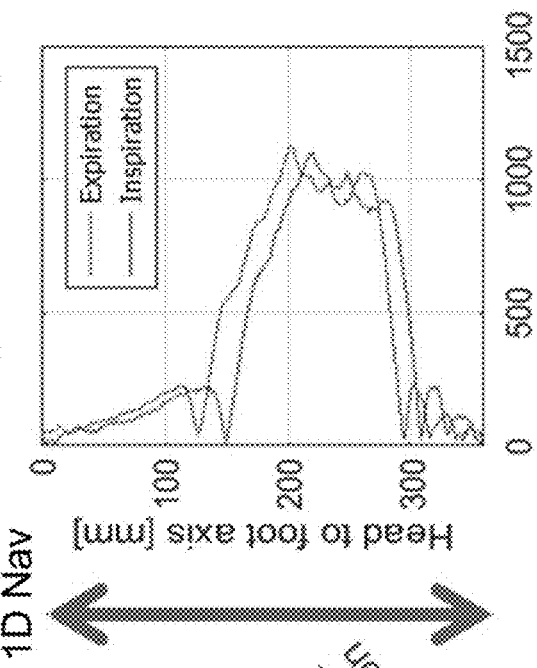
FIG. 5C is an example graph of the magnitude of the inverse Fourier transform of the 1D navigator shown in FIG. 2B versus spatial location along the head-to-toe axis for the expiration phase shown in FIG. 5A and for the inspiration phase shown in FIG. 5B.
Figure 5B:
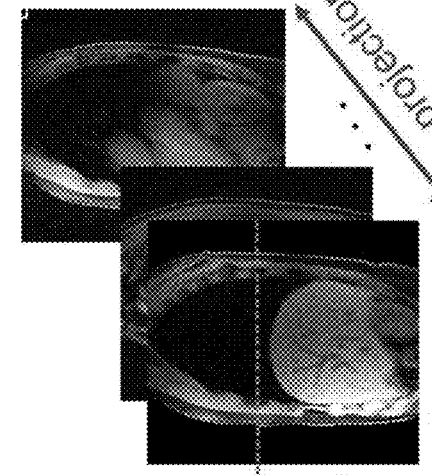
FIG. 5B is a schematic illustration showing a series of MR images reconstructed during a respiratory inspiration phase of a patient associated with the navigator-based acquisition method shown in FIG. 2B for the inspiration phase.
Figure 5A:
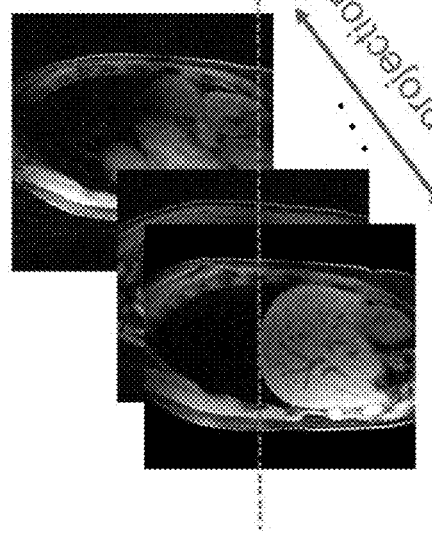
FIG. 5A is a schematic illustration showing a series of MR images reconstructed during a respiratory expiration phase of a patient associated with the navigator-based acquisition method shown in FIG. 2B for the expiration phase.

By way of non-limiting example, FIG. 5C is a graph showing the magnitude of the inverse Fourier transform of the 1D navigator as a function of distance along the head-to-toe axis in the image domain corresponding to the 1D navigator axis. As illustrated in FIG. 5C, the peaks and valleys of the inverse Fourier transform magnitudes shift to higher values during an expiration phase (blue line) versus during an inspiration phase (red line) of respiratory movements of the subject, indicating movements of organ positions at various respiratory motion phases that may be distinguished using the 1D navigator motion resolution method. In one aspect, the inverse Fourier transforms of the 1D navigators from all data scans may be compared and used to group subsets of all data scans into groups of scans obtained during a similar phase within the respiratory cycle. In this aspect, each group of scans obtained during a shared phase of the respiratory cycle may be combined to reconstruct an MR image of the subject during that shared respiratory cycle phase.

In various aspects, the magnitude and/or phase of the inverse Fourier transforms of the k-space data of each 1D navigator spokes associated with each MR data scan onto the corresponding axis in image space for each stack may be concatenated to identify changes in spatial location of one or more organs along the projected axis (i.e., the image x-axis) with respect to time.

In one aspect, each reverse Fourier transform of the k-space data of each 1D navigator spoke obtained during each MR data scan may be assembled into a map that includes a plurality of pixels in which each column of pixels on the map corresponds to a time at which the MR data scan was performed, and in which each row corresponds to a location along the image axis corresponding to the navigator axis. In various aspects, the map constructed from the combined inverse Fourier transforms of all 1D navigator measurements may further include a pixel brightness defined according to a characteristic value of the inverse Fourier transforms including, but not limited to, a magnitude and/or a phase of the inverse Fourier transform of the 1D navigator corresponding to the time of the scan and location along the image axis corresponding to the 1D navigator axis.

By way of non-limiting example, FIG. 6A and FIG. 6B are images of maps obtained by combining the magnitude (FIG. 6A) and the phase (FIG. 6B) of the inverse Fourier transform of the MR data associated with the 1D navigator for each data scan obtained at each scan time, in which the horizontal distance within each map corresponds to different data acquisition times used to index each data scan, and in which the vertical axis of each map corresponds to a position along the image axis corresponding to the 1D navigator axis in k-space. In one aspect, each pixel value may be proportional to the magnitude of each inverse Fourier transform, as illustrated in FIG. 6A. In another aspect, each pixel value may be proportional to the phase of each inverse Fourier transform, as illustrated in FIG. 6B.

In various aspects, at least a portion of the magnitude and/or phase map of the inverse Fourier transforms of the 1D navigator MR data may be used to construct a respiratory curve. Referring again to FIG. 6A and FIG. 6B, each column of pixels in the map are characterized by transition regions 602, 604, 606 characterized by relatively large changes in pixel value/brightness in the vertical direction, representing a change from one tissue/material to another, such as an outer surface of a liver or heart within a subject. Over the entire MR imaging period, represented by horizontal distance along each map, these transition regions 602, 604, 606 may shift vertically up or down the image axis corresponding to the 1D navigator axis in k-space as a result of respiratory and/or cardiac motions within the subject during MR imaging. In various aspects, the movements of one or more of these transition regions 602, 604, 606 may be used to determine a motion cycle of the subject during the MR imaging period.

FIG. 6C is a graph showing a motion cycle 608 assembled by combining the relative distances moved by transition region 602 at each time (i.e., column) within the phase map (see FIG. 6B) along the image axis during the acquisition of MR data. In one aspect, the upward and downward movements of the transition region 602 are determined by analysis of the phase map, and the values of movement are graphed as illustrated in FIG. 6C to assemble the movement cycle. In one aspect, the movement distances may be graphed as determined from the analysis of the magnitude map (FIG. 6A) or phase map (FIG. 6B) without further data processing. In various other aspects, the movement distances may be normalized using any known method of normalization without limitation. Non-limiting examples of suitable normalization methods include: subtracting the average of all movement distances from each movement distance, dividing all movement distances by a maximum movement distance, and any combination thereof.

In one aspect, if multi-element coils are used to acquire the images, only the signal of the single coil element that covers the moving organ well is used. To improve the robustness of respiratory curve detection, a low pass filter, including, but not limited to, a Hamming filter, may be applied to the K-space 1D navigator (N(k)) signal to reduce Gaussian noise prior to further analysis. A 1D FFT is applied to the filtered 1D navigator signal to convert the K-space signal N(K) into a spatial domain signal n(r), in which n(r)=FFT(N(k)).

By way of non-limiting example, magnitude and phase maps of a spatial domain signal n(r) produced as described above are illustrated in FIG. 6A and FIG. 6B, respectively. In an aspect, the respiratory signal may then be extracted by identifying the position of the maximal signal at each column (corresponding to a time of data acquisition) using any signal component including, but not limited to: signal magnitude, signal phase, real signal, or imaginary signal.

In various aspects, any one or more of a host of factors may induce contamination of the respiratory signal, including, but not limited to: phase shift of coils, background magnetic field, and magnet frequency drifting. Moreover, the degree of respiratory signal contamination due to any one or more of these factors may vary across separate scans of the same subject as well as between different subjects.

Figure 14A:
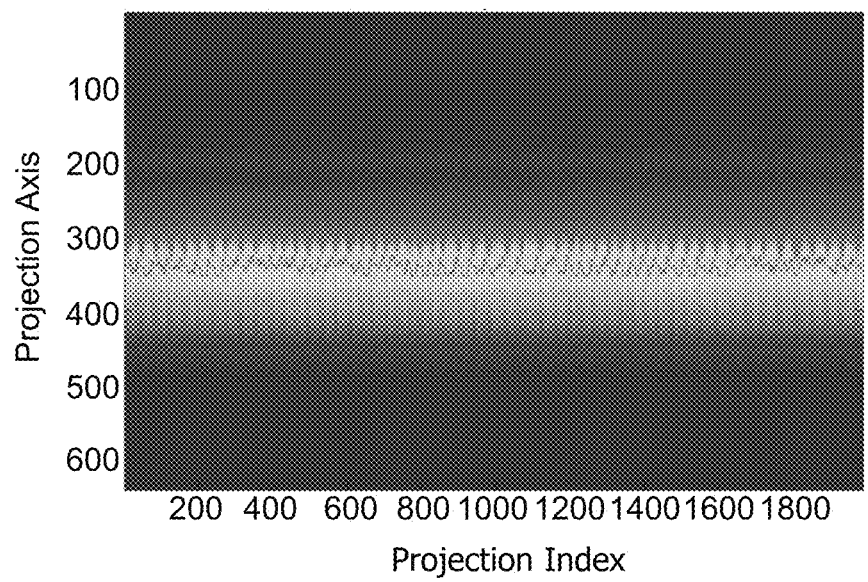
FIG. 14A is a map of the magnitude of n(r). The red line overlaid on the map denotes an automatically detected respiratory curve.
Figure 14B:
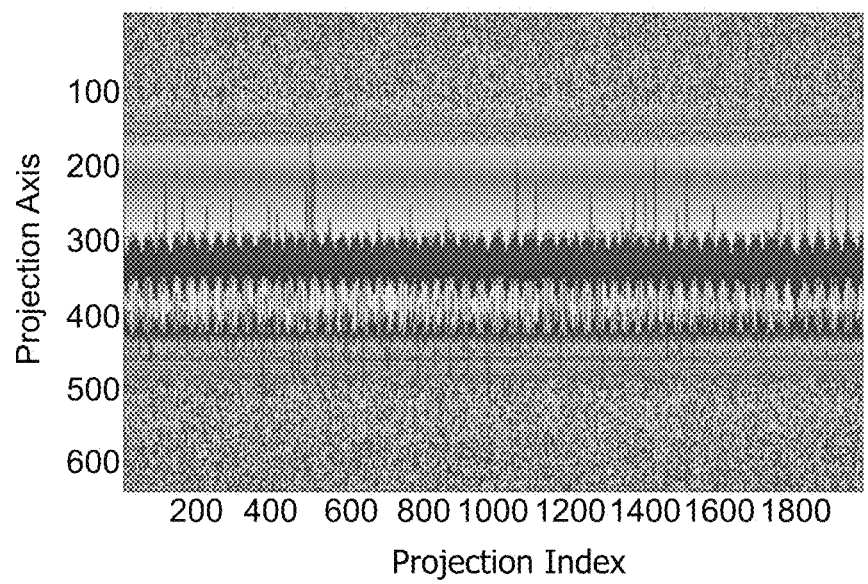
FIG. 14B is a map of the phase of n(r). The red line overlaid on the map denotes an automatically detected respiratory curve.
Figure 14C:
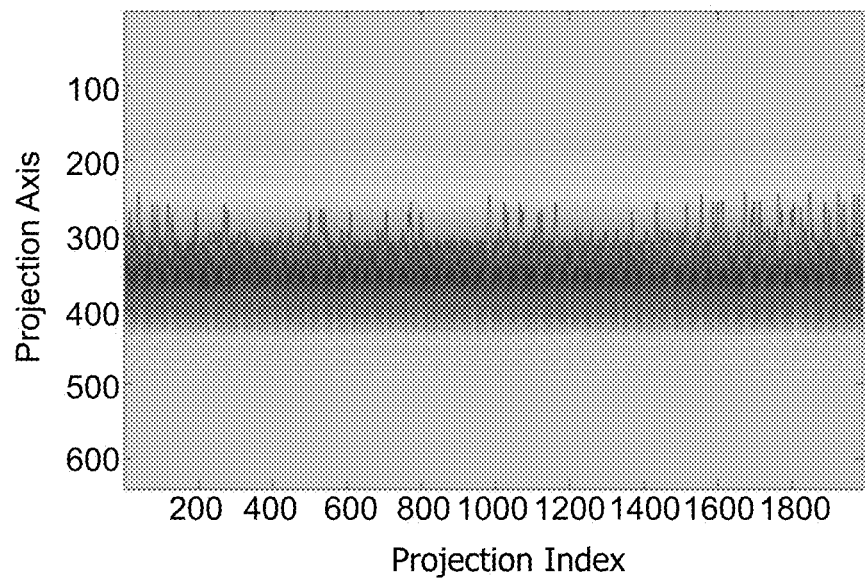
FIG. 14C is a map of the real part of n(r). The red line overlaid on the map denotes an automatically detected respiratory curve.
Figure 14D:
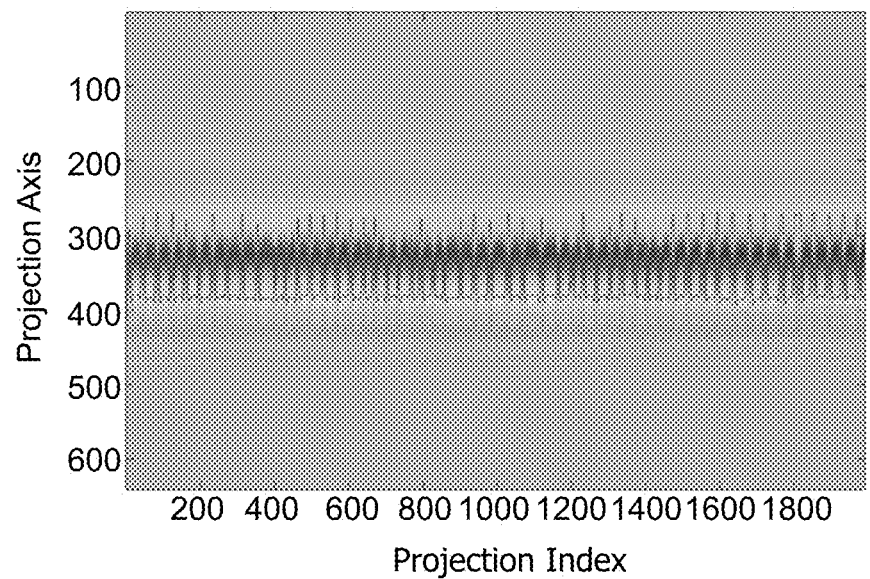
FIG. 14D is a map of the imaginary part of n(r). The red line overlaid on the map denotes an automatically detected respiratory curve.
Figure 15:
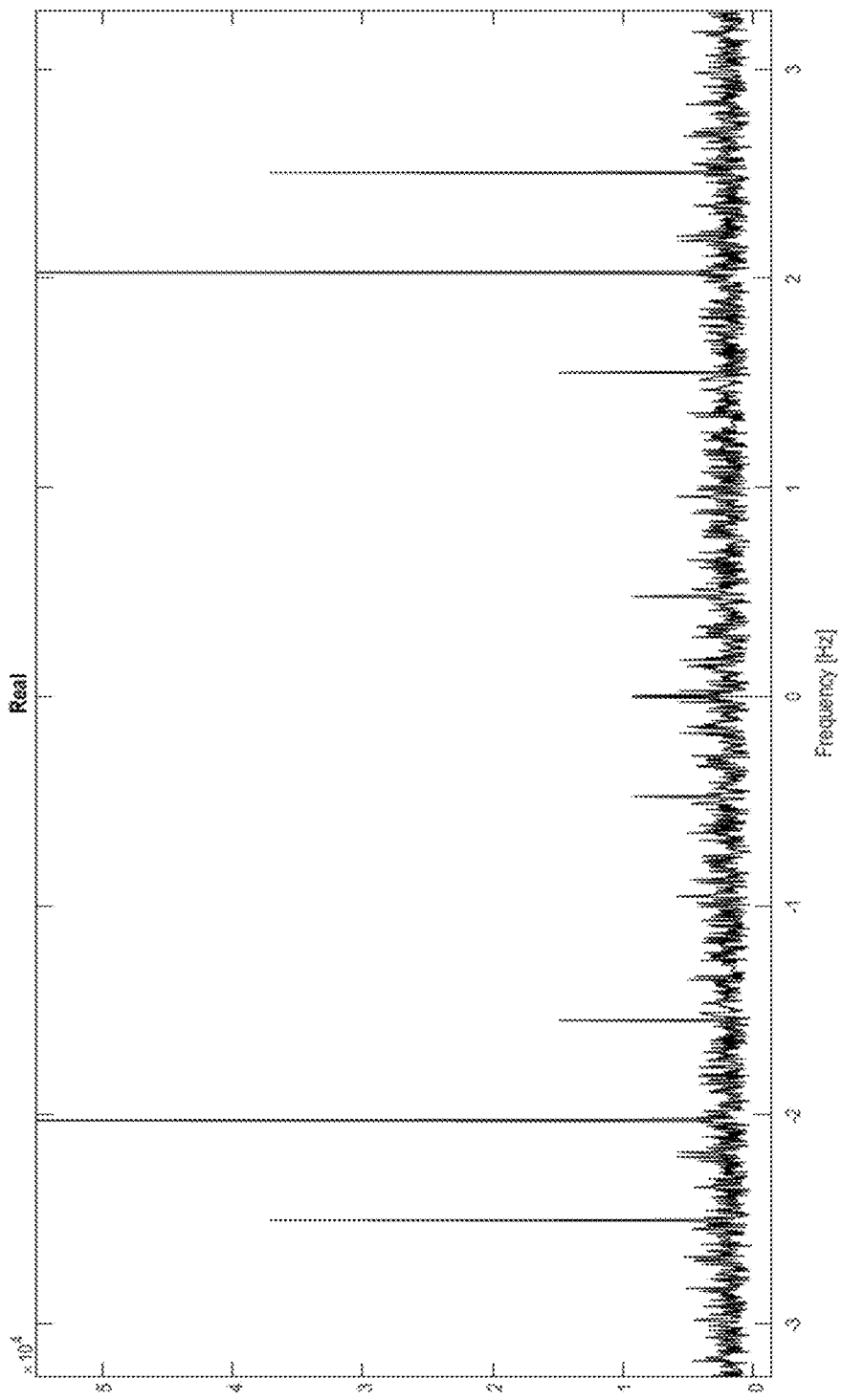
FIG. 15 is a graph showing the frequency spectrum derived from the map of the real part of n(r) shown in FIG. 14C.

As a result of erratic respiratory signal contamination, the reliable detection of the respiratory signal may be challenging. FIGS. 14A-14D are maps of automatically detected respiratory curves (denoted as superimposed red lines in all maps) using the magnitude of n(r) (FIG. 14A), the phase of n(r) (FIG. 14B), the real part of n(r) (FIG. 14C), and the imaginary part of n(r) (FIG. 14D). Comparing the respiratory signals illustrated in FIGS. 14A-14D, which were all derived from the same set of K-space 1D navigator signals, it is evident that signal contamination may lead to spurious respiration detection. As illustrated in the frequency spectrum derived from the real part of n(r) illustrated in FIG. 15, the respiratory curve detected using the real part of n(r) may be contaminated by the lack of strong signals in the expected physiological frequency range (0-0.5 Hz), while there is a presence of 'artificial signal' caused by gradient system imperfections in a frequency range >1 Hz.

In various aspects, the complex part of the n(r) signal may be tuned to produce an enhanced signal within the physiological frequency bandwidth that may be used to automatically detect physiological motion with enhanced reliability. In one aspect, n(r) may be rotated with an angle $\phi$ as $n(r)*\exp(-j\phi)$. In this aspect, 360 different candidate $\phi$ values in the range of [0 360°] with an increment of 1° may be used to rotate n(r) using the relation $(r)*\exp(-j\phi)$. The real part of the rotated n(r) (i.e. $\mathrm{Real}(n(r)*\exp(-j\phi_i))$) for each candidate $\phi_i$ may be used to extract a respiratory signal corresponding to the corresponding $\phi_i$.

In this aspect, a Fourier transform of the detected temporal respiratory curve may be used to obtain its frequency spectrum. In various aspects, the quality of the detected temporal respiratory curves for each candidate rotation angle $\phi_i$ may be evaluated by analysis of each corresponding frequency spectrum of the detected respiratory curve. In one aspect, the frequency spectrum may be integrated within an expected frequency range of physiological motion including, but not limited to, a frequency range from about 0.1 Hz to about 0.5 Hz to represent to degree to which each detected respiratory curve captures the expected respiratory motion. In another aspect, the frequency spectrum may be integrated within a frequency range expected to fall outside of expected frequencies of physiological motion including, but not limited to, a frequency higher than about 1 Hz to represent to degree to which each detected respiratory curve is confounded by the signal contamination effects described herein above. In another aspect, the values of the integrated frequency spectrums at different frequency sub-ranges may be combined to assess the quality of a respiratory signal derived using each of the candidate various rotation angle $\phi_i$. In this other aspect, the values of the integrated frequency spectrums may be combined in any mathematical relation without limitation, including, but not limited to: a sum, a difference, a product, a ratio, a trigonometric function, an exponential function, a correlation, and any other mathematical relation.

In one aspect, a ratio between the values of each frequency spectrum obtained at the expected physiological frequency range as described above (i.e. 0.1-0.5 Hz) and at the expected non-physiological/artifact frequency range as described above (i.e. >1 Hz) may be computed as an indicator of the relative strength of these signals. In an aspect, this computed ratio between the physiological signal and artifact signal may be analyzed as a quality metric, in which the largest ratio is thought to incorporate a higher proportion of signals within the expected physiological range relative to artifact signals.

Figure 16:
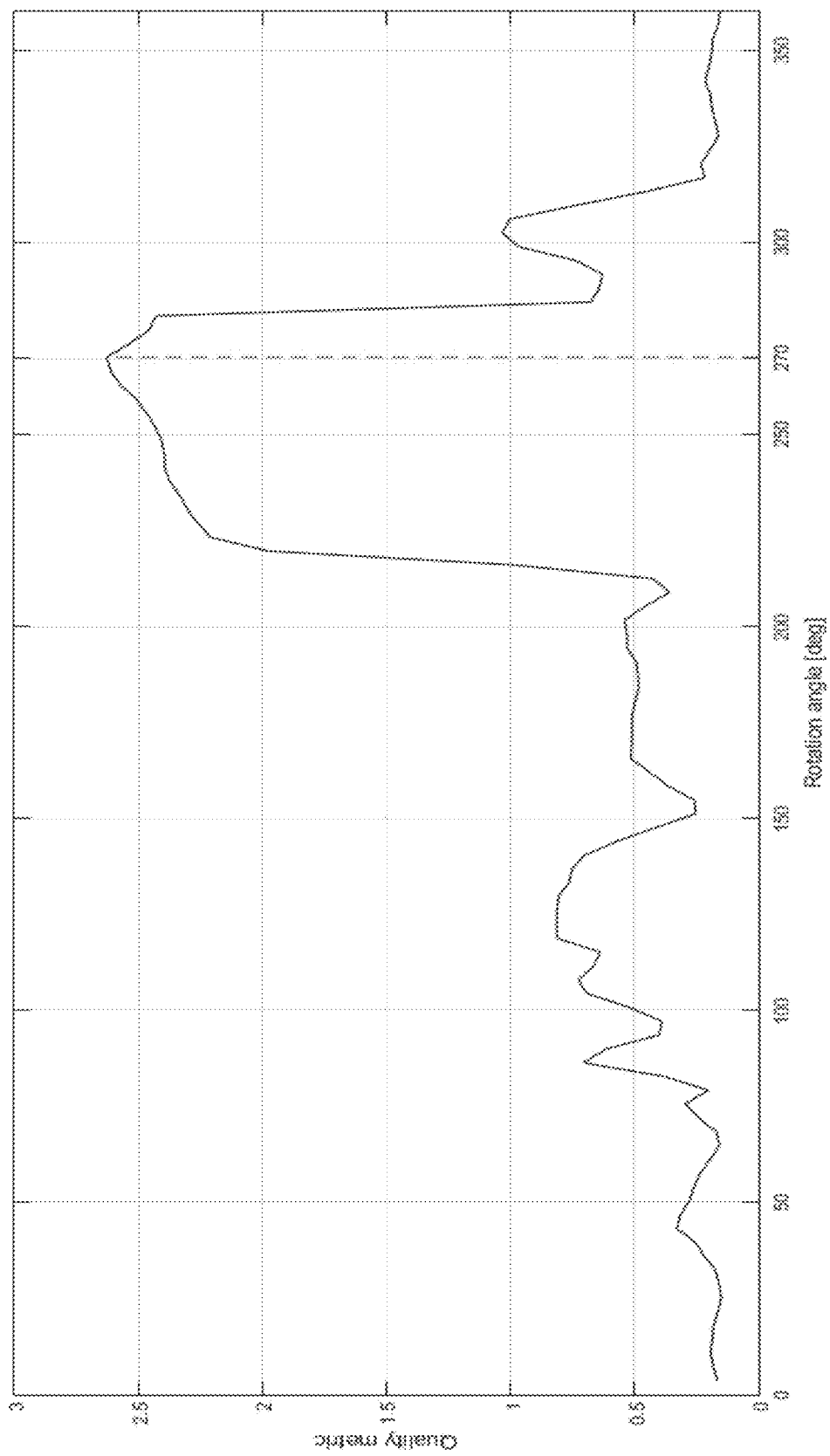
FIG. 16 is a graph showing a frequency spectrum energy ratio between the 0.1-0.5 Hz frequency range and the >1 Hz frequency range as a function of rotation angle, as derived from the frequency spectrum of FIG. 15.

FIG. 16 is a graph showing the calculated ratios of integrated portions of the respiratory signal frequency spectrums for each candidate $\phi_i$ (labeled as "Quality metric")

plotted as a function of the corresponding candidate $\phi_i$. Referring again to FIG. 16, the optimal candidate $\phi_i$ (i.e. $\phi_{optimal}$), may be identified as the $\phi_i$ that provides the largest ratio. As illustrated in FIG. 16, in this case $\phi_{optimal}$ was 270 degrees, as denoted by the overlaid dashed red line.

Figure 17:
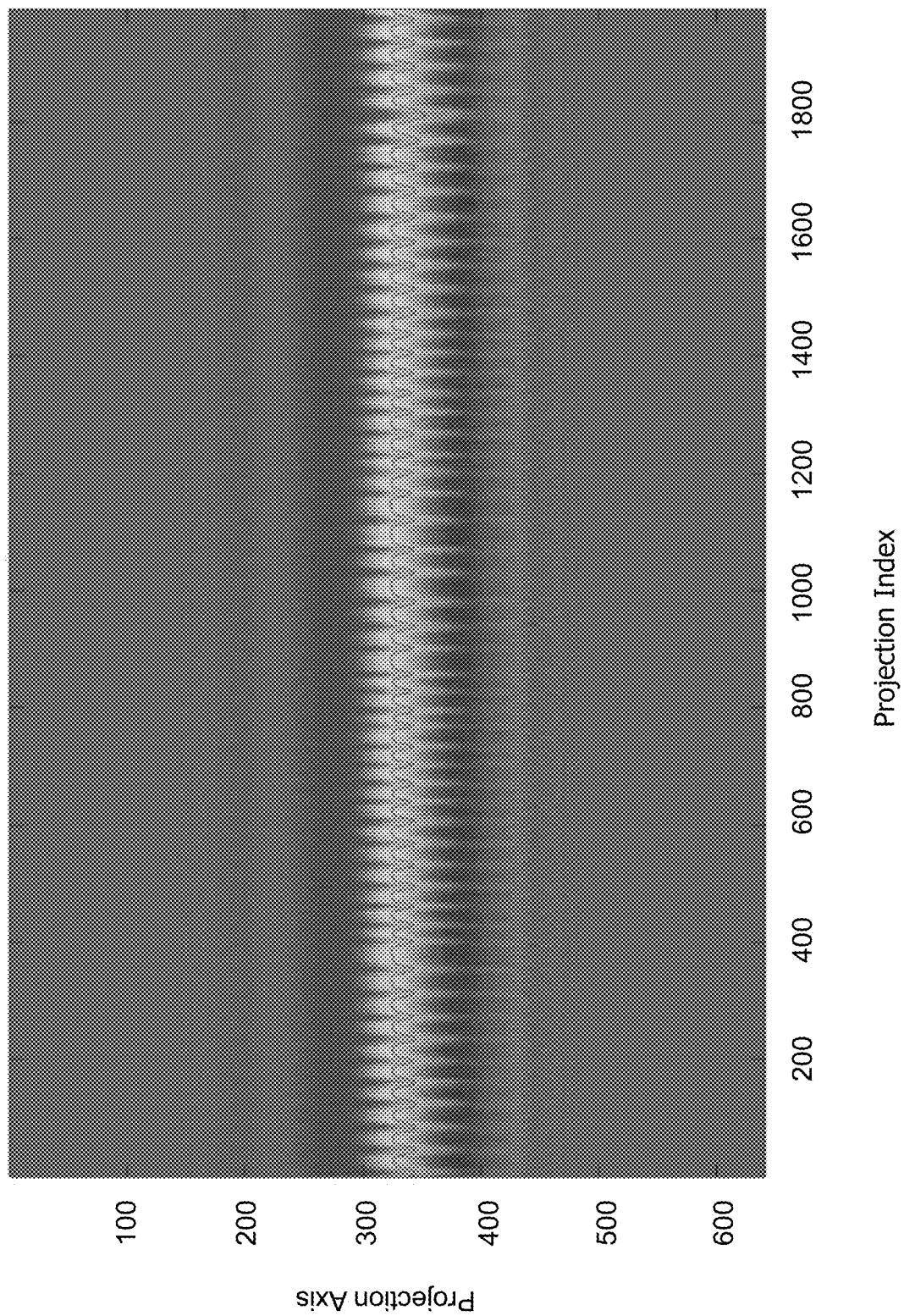
FIG. 17 is a map of the real part of the rotated complex navigator $n(r)exp(-j\phi)$ for $\phi=270$.
Figure 18:
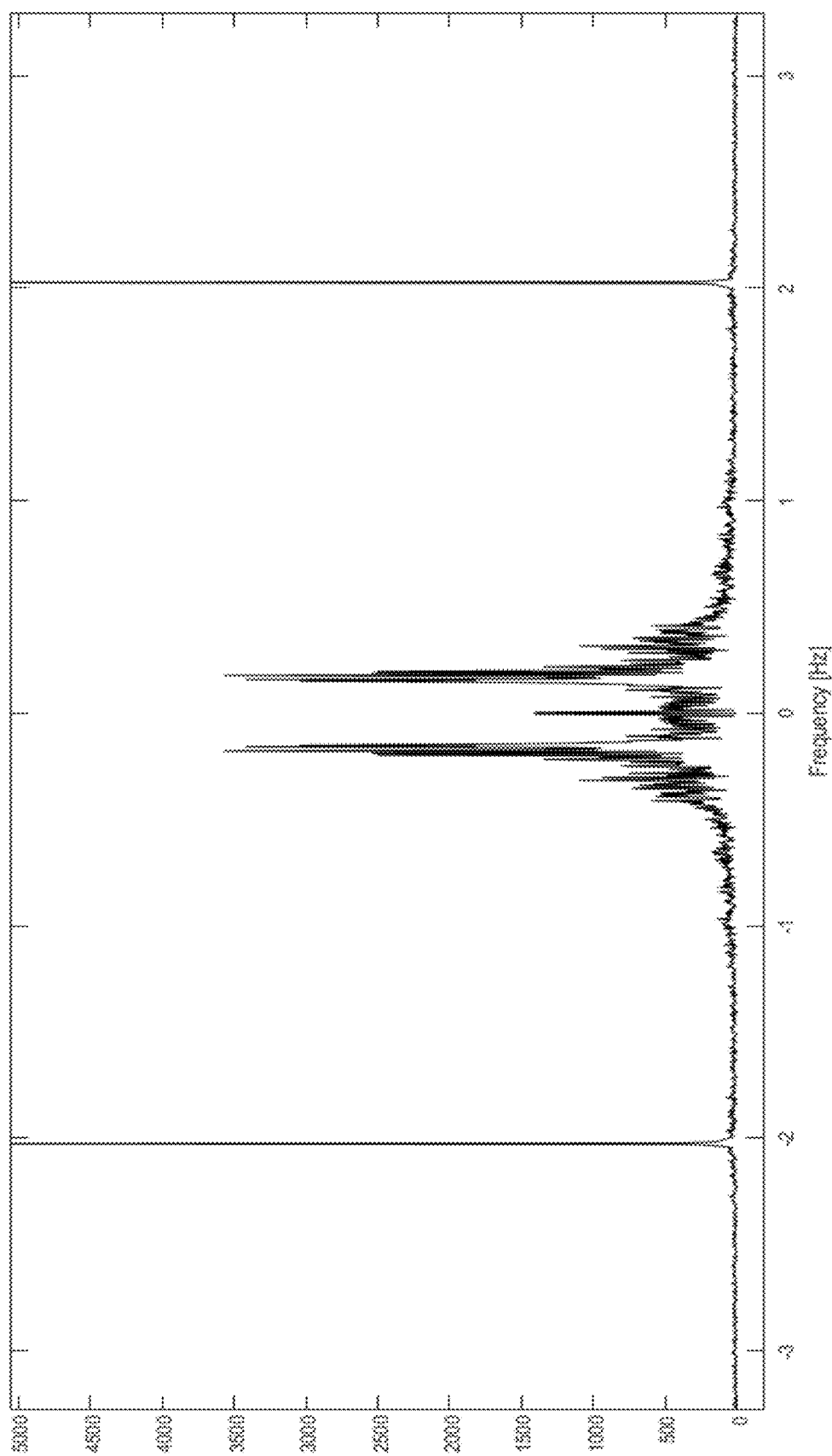
FIG. 18 is a graph showing a frequency spectrum derived from the map of the real part of the rotated complex navigator $n(r)exp(-j\phi)$ for $\phi=270$, shown in FIG. 17.

In this aspect, once the $\phi_{optimal}$ is identified, Real(n(r)*exp(−j$\Phi_{optimal}$)) may be used to detect the temporal respiratory curve as described herein previously. FIG. 17 is a map of Real(n(r)*exp(−j$\phi_{optimal}$) with the automatically detected respiratory signal denoted as a superimposed red line. The frequency spectrum of the respiratory signal shown in FIG. 17 is shown in FIG. 18. Comparing the frequency spectrum shown in FIG. 18 with the frequency spectrum shown in FIG. 15 (respiratory signal detected from uncorrected real portion of n(r)), the rotation of n(r) prior to detection of the respiratory signal results in a significant reduction in the contributions of signal contamination as described herein above. As illustrated in FIG. 17 and FIG. 18, the 'tuning' of the navigator n(r) may enhance the reliability of this signal to detect respiratory motion. Without being limited to any particular theory, the tuning of the phase of n(r) is analogous to the tuning of the frequency of a radio to enhance the desired signal (i.e. a signal produced by a frequency assigned to a radio station).

Figure 33A:
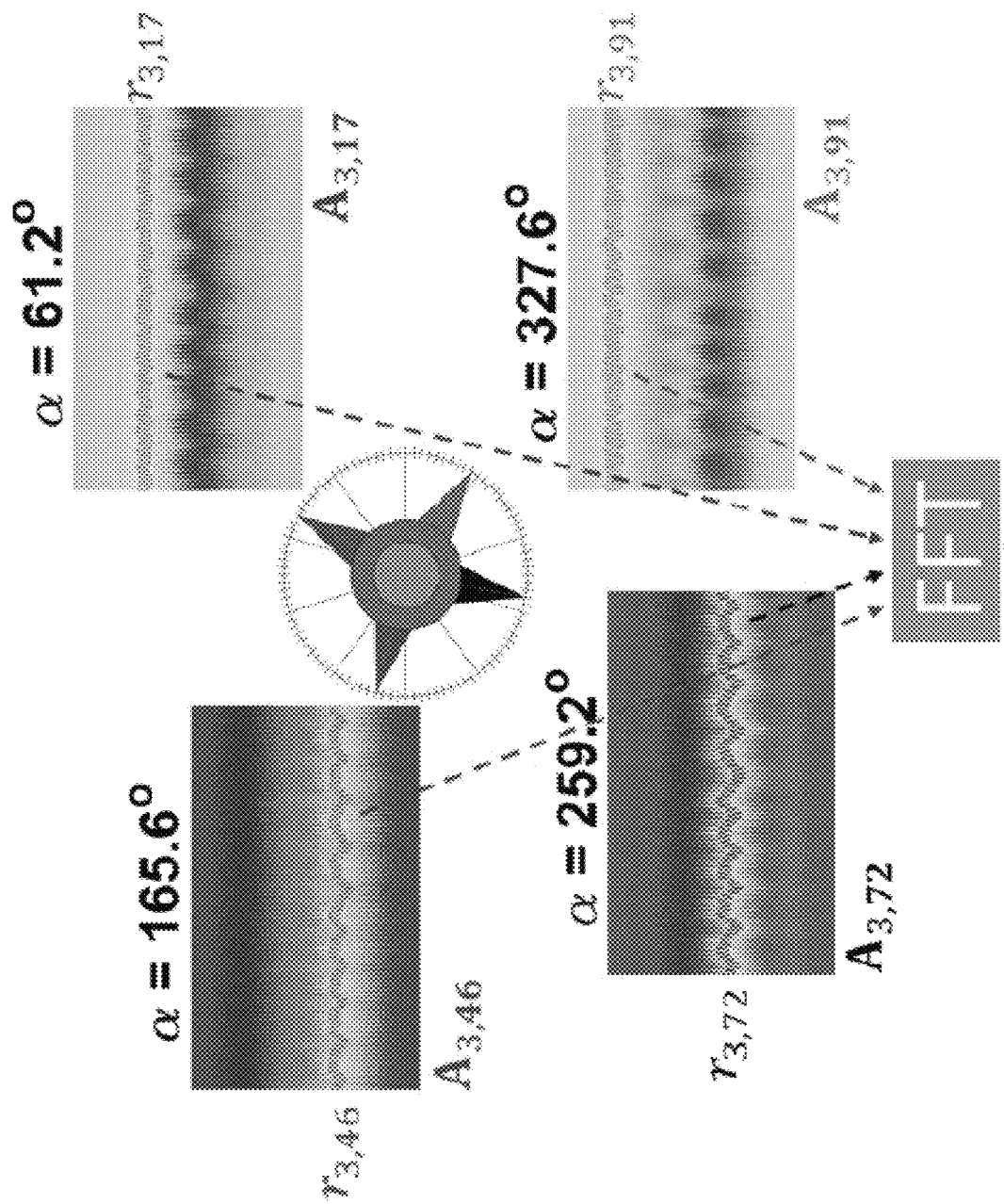
FIG. 33A contains four representative $A_{i,m}$ maps for four phase rotations for a chosen coil (Coil 3), in which the x-axis, the y-axis and the color-axis of each map represent time, navigator axis, and the signal intensity of $A_{i,m}$ respectively.
Figures 33B, 33C:
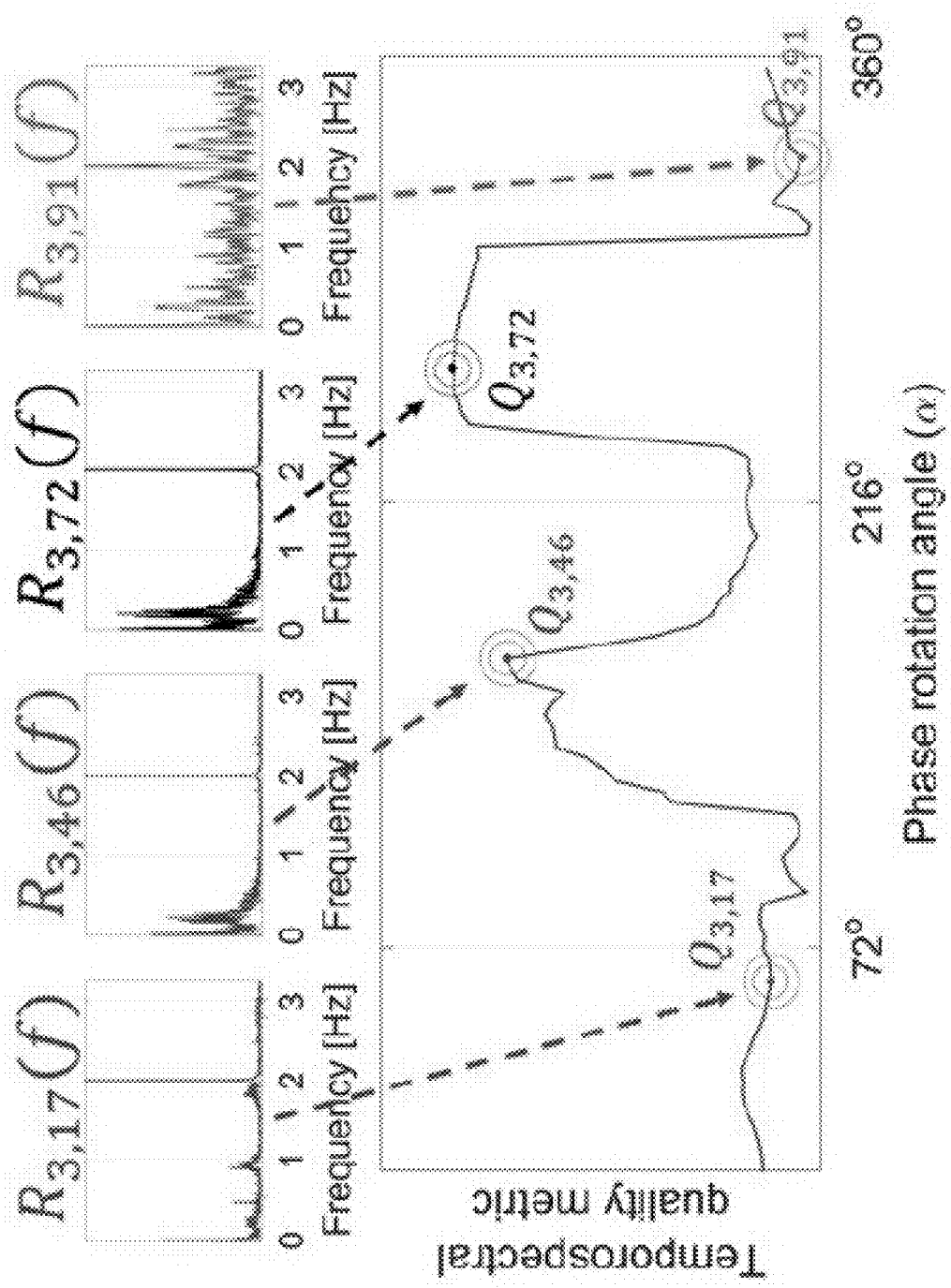
FIG. 33B contains four unfiltered respiratory curves $r_{i,m}[n]$ derived from the $A_{i,m}$ maps of FIG. 33A.
FIG. 33C is a graph of a temporospectral quality metric derived from all respiratory curves $r_{i,m}[n]$ and $A_{i,m}$ maps for the chosen coil (Coil 3); individual temporospectral quality metrics corresponding to the four respiratory curves $r_{i,m}[n]$ illustrated in FIG. 33B are overlaid on the graph of FIG. 33C. The optimal phase rotation identified from the graph of FIG. 33C was 259.2°, corresponding to $R_{3,72}(f)$.

FIG. 33A, FIG. 33B, and FIG. 33C are schematic illustrations of the automated motion cycle detection method in another aspect. In one aspect, the first 10 stacks of spokes obtained during MR imaging are discarded to ensure steady-state conditions. In another aspect, the navigator k-space data were apodized using a Hamming window to reduce noise. After a 1D inverse FT, the resulting complex projections $P_i$ received through the $i^{th}$ coil of the MRI scanner from all stacks of spokes were concatenated as columns of a 2D matrix $P_i = P_i[x, n]$ where x is the index for the physical locations on the superior-inferior (x) axis and n is the stack-of-spokes index or, equivalently, the discrete time index. A tuning process was then performed by phase-rotating Pi's over the full phase range, (0,360°], via 100 different complex scalar multiplications $e^{-(j\alpha_m)}P_i$ where $\alpha_m = m \times 3.6°$ with m=1, 2 ... 100. Four representative phase rotations are illustrated in FIG. 33A. For each $\alpha_m$, a respiratory curve $r_{i,m}[n]$ was obtained by detecting the location of the peak along each column of $A_{i,m} \triangleq Re\{e^{-(j\alpha_m)}P_i\}$, where Re{.} is the real part operator. The four illustrations of $A_{i,m}$ and the $r_{i,m}[n]$ corresponding to the four phase rotation angles $\alpha_m = [61.2°, 165.6°, 259.2°, 327.6°]$ and for Coil 3 (i=3) are also shown in FIG. 33A.

The detected respiratory curves, $r_{i,m}[n]$, were Fourier-transformed, yielding $R_{i,m}(f)$. Examples of $R_{i,m}(f)$ corresponding to the phase rotations illustrated in FIG. 33A are shown in FIG. 33B.

A temporospectral quality metric was calculated for each $r_{i,m}[n]$ and corresponding $R_{i,m}(f)$ as defined by Eqn. (6):

$$Q_{i,m} = \frac{\int_{0.1\,Hz}^{0.5\,Hz} |R_{i,m}(f)|df}{\int_{0.8\,Hz}^{\infty} |R_{i,m}(f)|df} \times \left(\frac{1}{\max_n r_{i,m}[n] - \min_n r_{i,m}[n]}\right) \quad \text{Eqn. (6)}$$

Figure 34A:
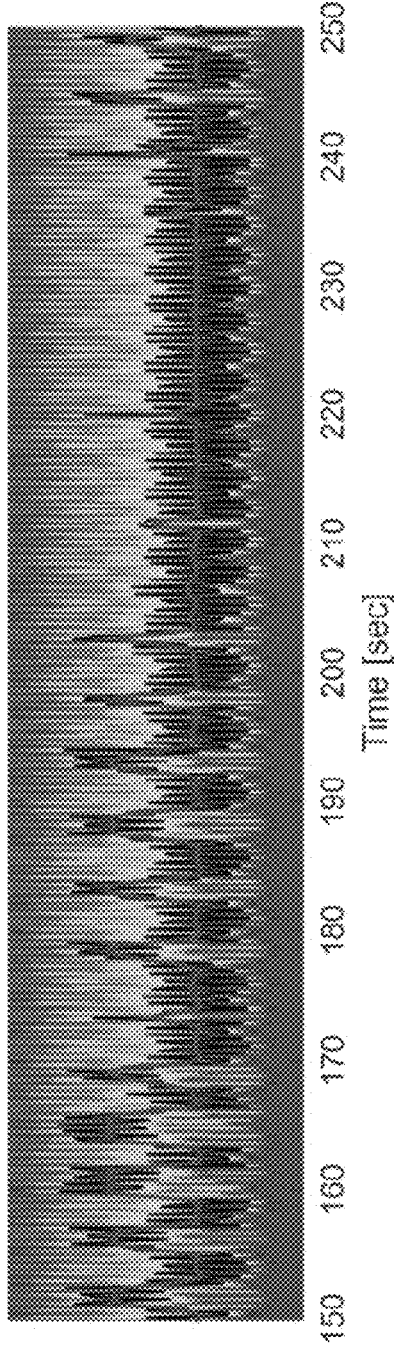
FIG. 34A is an image of an $A_{i,m}$ map obtained without use of range scaling.
Figure 34B:
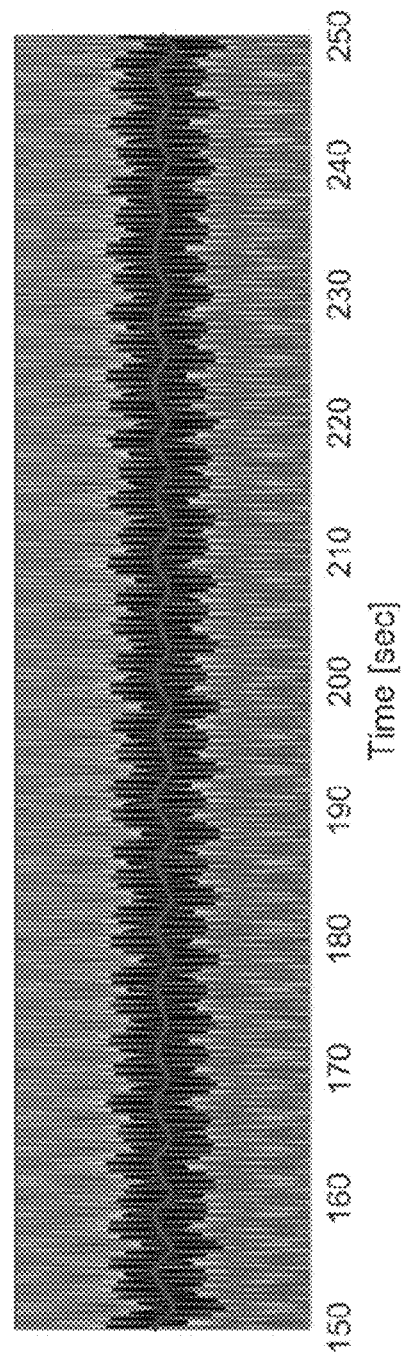
FIG. 34B is an image of $A_{i,m}$ map obtained with range scaling.

The first term of Eqn. (6) favors respiratory content over system-related spectral contamination, whereas the second term penalizes the peak-to-trough range of the detected curve. FIG. 34A and FIG. 34B illustrates the importance of this second term, i.e. the range term. For a number of tuning angles, parts of the detected respiratory curve can appear on spatially separated bands, as demonstrated in FIG. 34A. The abrupt signal changes observed in these cases can lead to spectral leakage into the respiratory range of frequencies, misleading the detection procedure. The second term penalizes these problematic abrupt changes, promoting only truly respiratory curves, as illustrated in FIG. 34B.

FIG. 33C is a graph of the temporospectral quality metric $Q_{i,m}$ values as a function of phase rotations.

In this aspect, the best coil (index i*) and phase-rotation (m*) were chosen according to Eqn. (7):

$$(i^*,m^*) = \text{argmax}_{(i,m)} Q_{i,m} \quad \text{Eqn. (7)}$$

A low-pass filter with a cut-off frequency of 1 Hz was used for removing physiologically irrelevant contamination. In order to avoid filtering-related distortion, Savitzky-Golay filtering output was used for replacing the samples at the two ends.

C. Production of Motion-Corrected MR Images

In various aspects, the motion cycle is be used to group the MR imaging data into portions, in which each portion is associated with a portion of the motion cycle. In one aspect, the portion of the MR imaging data associated with one bin is combined and reconstructed into an MR image of the subject at the corresponding portion of the motion cycle.

In various aspects, the motion cycle 608 may be divided or "binned" into different regions or "bins" corresponding to shared phases of the motion cycle with similar movement distances along the imager axis corresponding to the 1D navigator axis within the k-space. Referring again to FIG. 6C, adjacent bins within a motion cycle 608 may be separated by a horizontal boundary 610 constructed over the motion cycle 608. With respect to FIG. 6C, in one aspect, the MRI system (e.g., system 100, shown in FIG. 1) is configured to define boundaries 625 for the respiratory signal. The boundaries 625 define a plurality of motion phases of a motion cycle. In this example, the boundaries 625 define respiratory phases of a respiratory cycle. In the example embodiment, five motion phases are defined. In other embodiments, a different number of motion phases are defined by a different number of boundaries 625. Accordingly, the acquired data is binned based on these boundaries 625 to facilitate reconstructing the respiratory cycle for display to a user.

In various aspects, the motion cycle may be binned according to any suitable binning scheme without limitation. In one aspect, the binning scheme may be selected to divide the motion cycle into regions of relatively equivalent movement distances along the image axis. In another aspect, the binning scheme may be selected to divide MR data scans of the motion cycle into groups with essentially equal numbers of MR data scans. The number of regions or bins resulting from the binning scheme may be any suitable number without limitation. In various aspects, the number of bins may be selected to ameliorate blurring or other motion-related artifacts within the MR images reconstructed from the binned MR imaging data. In another aspect, the number of bins may be selected to enable the processing and reconstruction of MR imaging data into MR images of suitable image quality within a reasonable processing time. In various aspects, the number of bins of data resulting from the binning scheme may be at least two bins, at least three bins, at least four bins, at least five bins, at least six bins, at least seven bins, at least eight bins, at least nine bins, and at least ten bins or more. In one aspect, the binning scheme may divide the MR data scans associated with the motion cycle into 5 groups or bins.

Figure 7A:
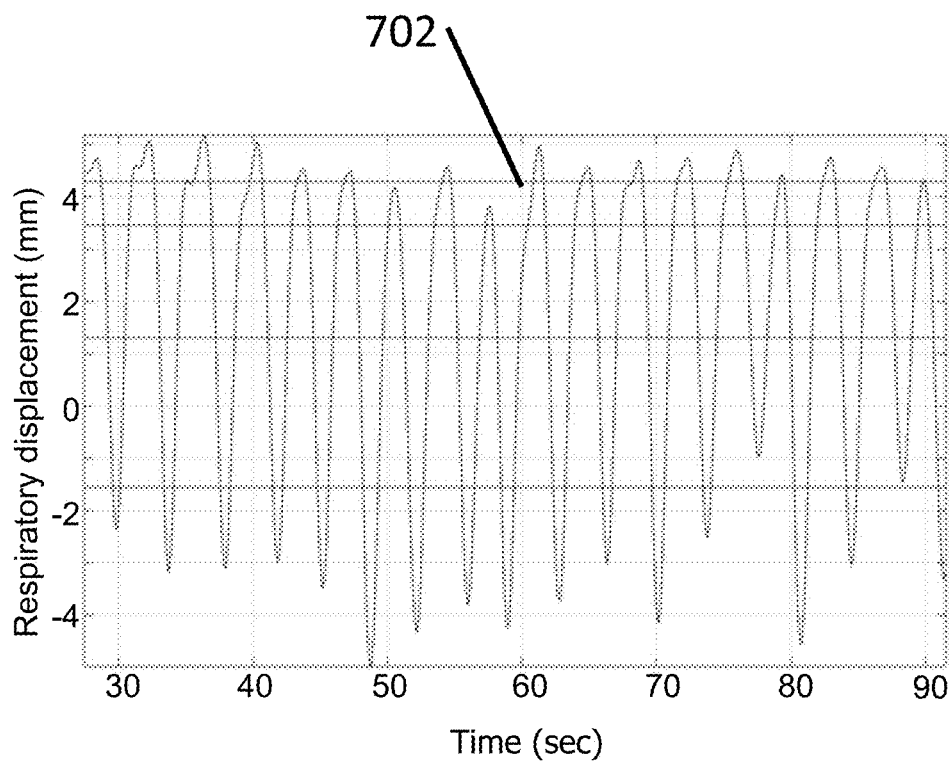
FIG. 7A is a graph of a respiratory cycle derived using the motion resolution method illustrated in FIGS. 6A, 6B, and 6C, in which the respiratory cycle has been binned into motion phases (shown separated by horizontal lines); each bin contains an equal number of spokes (corresponding to scans) according to the 3D stack-of-stars with 1D navigator MR acquisition sequence.
Figure 7B:
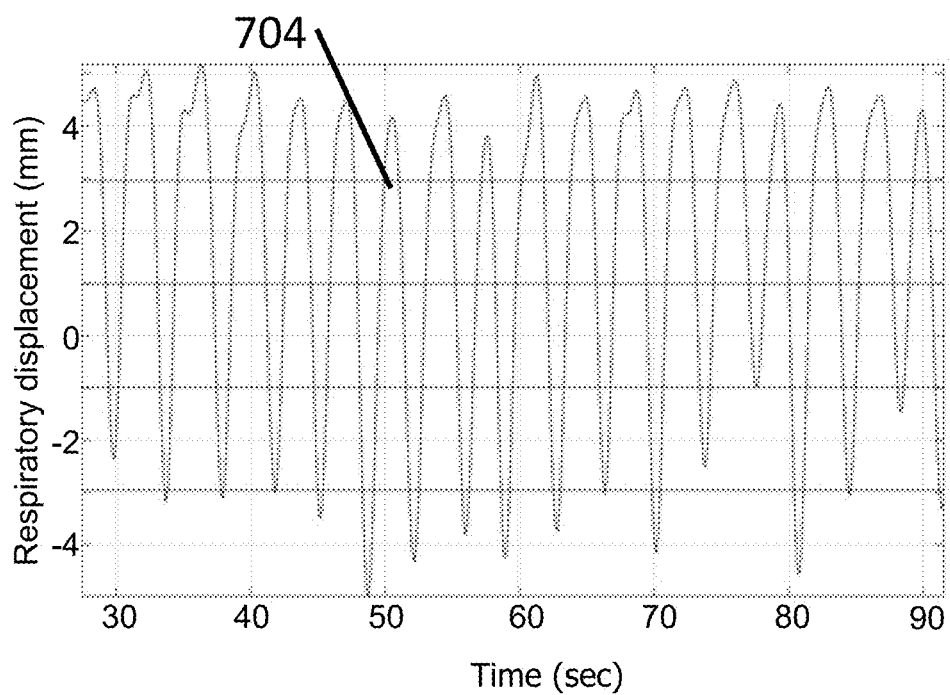
FIG. 7B is the graph of the respiratory cycle illustrated in FIG. 7A in which the respiratory cycle has been binned into motion phases (shown separated by horizontal lines); each bin corresponds to equal ranges of motion within the respiratory cycle.

FIG. 7A is a graph illustrating the binning the data based on an equal number of spokes (each spoke corresponding to an MR data scans at one azimuthal angle). In FIG. 7A, the binning of the MR data is specified such that each motion phase/bin includes the same number of radial spokes. Boundaries 702 defined between the motion phases are not equally spaced apart in FIG. 7A since the motion phases are not necessarily uniform in their duration. For example, in a typical respiratory cycle, the exhalation phase is longer that the inhalation phase. FIG. 7B is a graph illustrating the binning of the same data shown in FIG. 7A based on an equal motion distance. Boundaries 704 are positioned to be equally spaced apart in the graph (i.e. separate by equal displacement distances), in which the full range of motion is determined between the 1st and 99th percentile of the derived motion curve.

In various aspects, once the motion cycle is binned as described herein previously, the individual MR data scans corresponding to the motion cycle may be selected and grouped according to membership within one of the bins or groups corresponding to a phase within the motion cycle. In one aspect, the sub-ranges time on the motion cycle may be identified for each bin of the motion cycle, and those data scans with data acquisition times falling within the sub-ranges of time falling within each sub-range of time may be associated with the corresponding bin of the motion cycle and grouped for subsequent analysis.

In various other aspects, once the acquired MR data is binned within the various motion phases, each group/bin of MR motion data may be combined or otherwise analyzed to reduce motion artifacts within the reconstructed MR images for each motion phase/bin. In one aspect, each group of MR data associated with each bin of the motion cycle may be combined using any known method including, but not limited to, averaging, prior to MR image reconstruction in order to remove motion artifacts and other outlying data from the reconstructed MR images for each motion cycle phase.

In various aspects, the reduction of artifacts in the MR data acquired using the 1D navigator motion resolution method disclosed herein enhances the quality of MR images reconstructed using the acquired MR imaging data compared to existing methods. By way of non-limiting example, MR images of the same subject were generated using a point navigator method and using a 1D navigator method to compare the resulting image quality. FIG. 4A is a frequency spectrum of MR data obtained using the k-space center as a point navigator. FIG. 4B is a frequency spectrum of MR data obtained using the 1D navigator as described herein previously. Referring again to FIG. 4A, acquisition artifacts are induced near or within the motion frequency range (about −0.5 Hz to about +0.5 Hz). However, using the 1D navigator acquisition method, the acquisition artifacts are reduced, and the majority of any remaining artifacts are characterized by signal frequencies outside of the frequencies associated with physiological motion cycles, and as a result may be removed by any suitable data processing method including, but not limited to, data filtering. FIG. 4B is an MR image reconstructed using the MR data of FIG. 4A, and FIG. 4D is an MR image reconstructed using the MR data of FIG. 4C. Comparing FIG. 4B to FIG. 4D, the reduction of data artifacts resulting from the use of the 1D navigator method results in higher image quality; the MR image of FIG. 4D is sharper in comparison to the MR image of FIG. 4B.

Although the 1D navigator motion resolution method described herein is presented in the context of motion cycles such as respiratory and cardiac cycles, it to be understood that any general motion of the subject may be resolved using the 1D navigator motion resolution method including, but not limited to, cyclic motions such as respiratory and/or cardiac cycles, and non-cyclic motions such as positional shifts of the patient during MR scanning associated with muscle twitches, sneezing, hiccupping, sliding, and any other positional shift of the subject.

Figure 19:
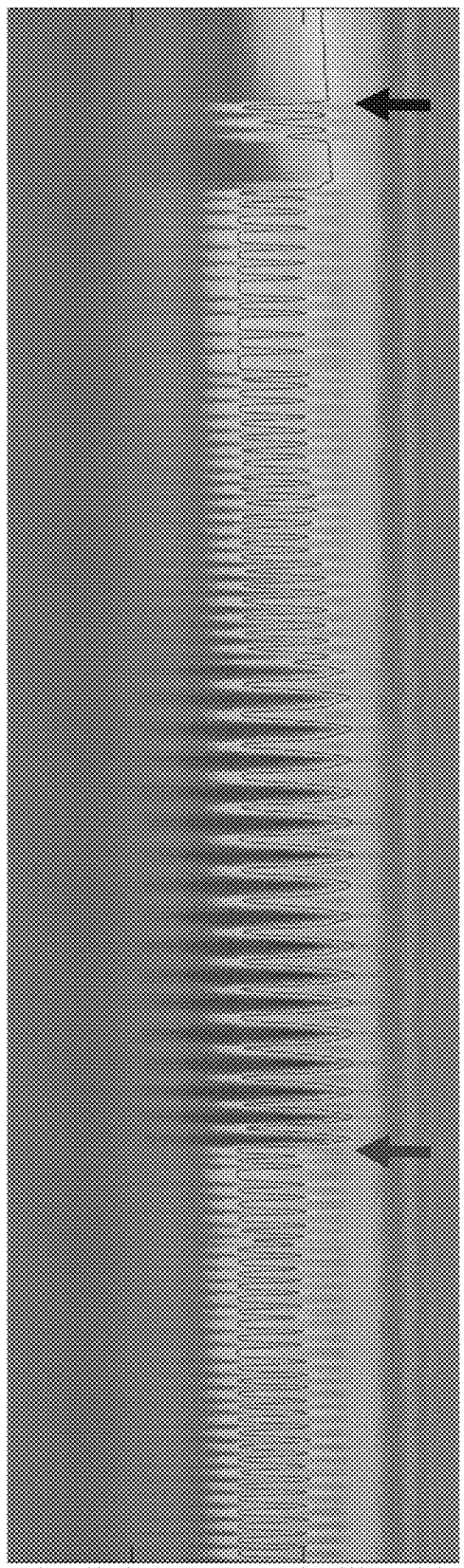
FIG. 19 is a map with an automatically detected respiratory motion curve overlaid as a red line obtained during different breathing patterns. Red and black overlaid arrows mark the duration (start and stop times, respectively) that a subject was asked to take a deep breath or a breath holding.
Figure 20:
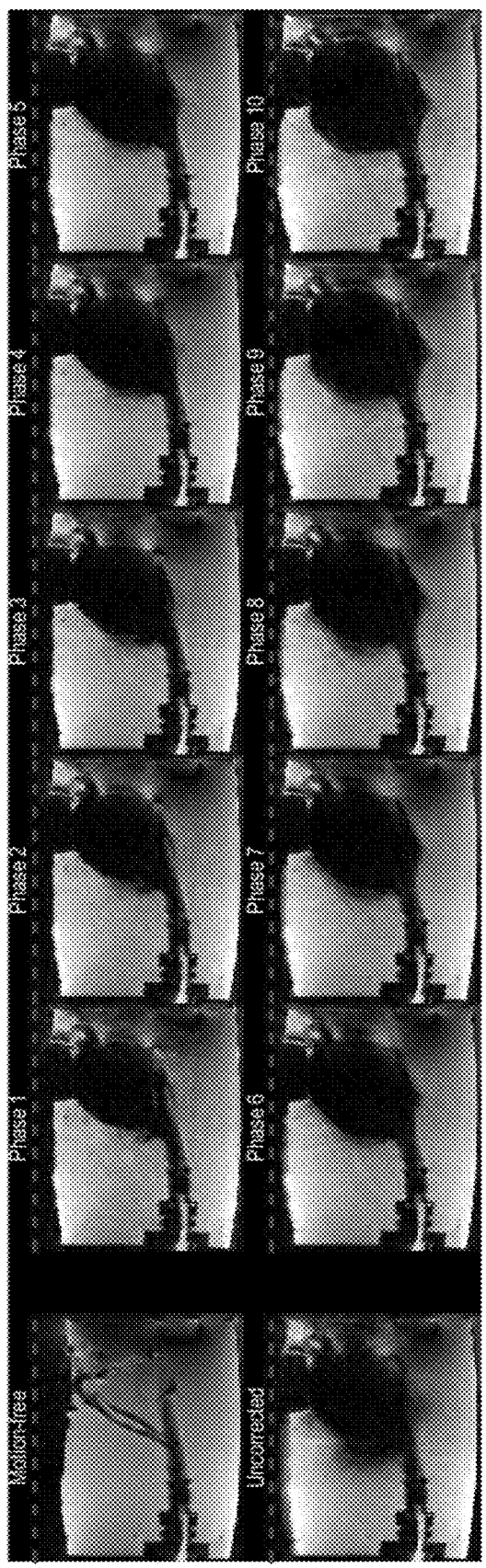
FIG. 20 is a series of images of a deformable motion phantom obtained using a method according to one aspect, during a variety of conditions, including motion-free and motion uncorrected, as well as motion corrected during 10 phases of a simulated 4D respiratory motion cycle (x, y, z, phase).
Figure 21B:
FIG. 21B is a series of images showing the transects from which the data of FIG. 21A were derived.
Figure 21A:
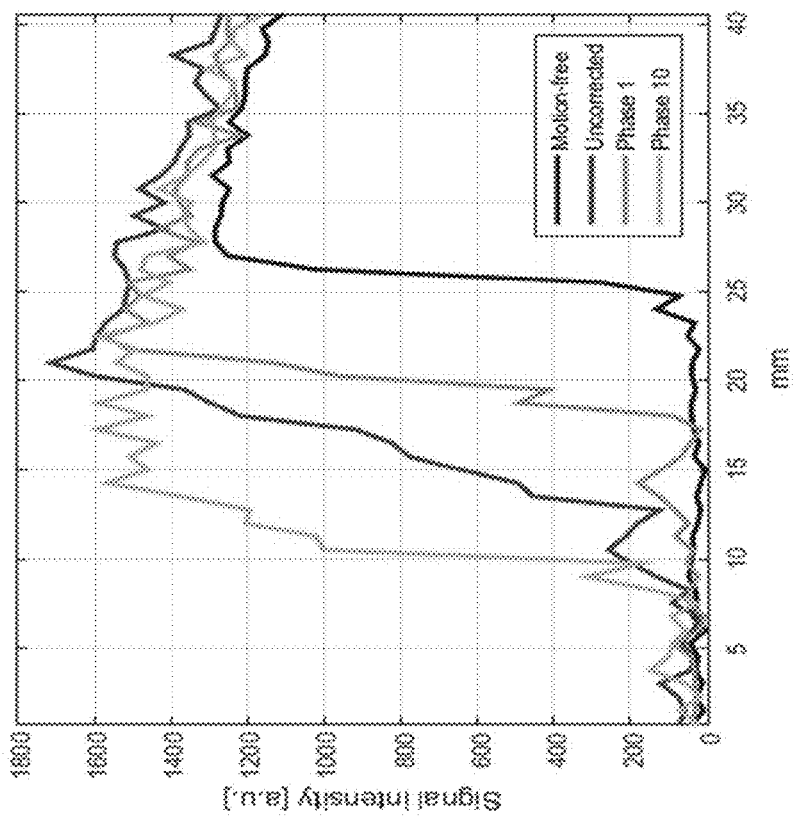
FIG. 21A is a graph showing the signal intensity profiles as a function of distance along a transect extending across a discontinuity in a deformable motion phantom, as illustrated in FIG. 21B, for several conditions, including motion-free (blue line), uncorrected (red line), phase 1 of a simulated respiratory cycle (green line), and phase 10 of a simulated respiratory cycle (turquoise line).
Figure 22:
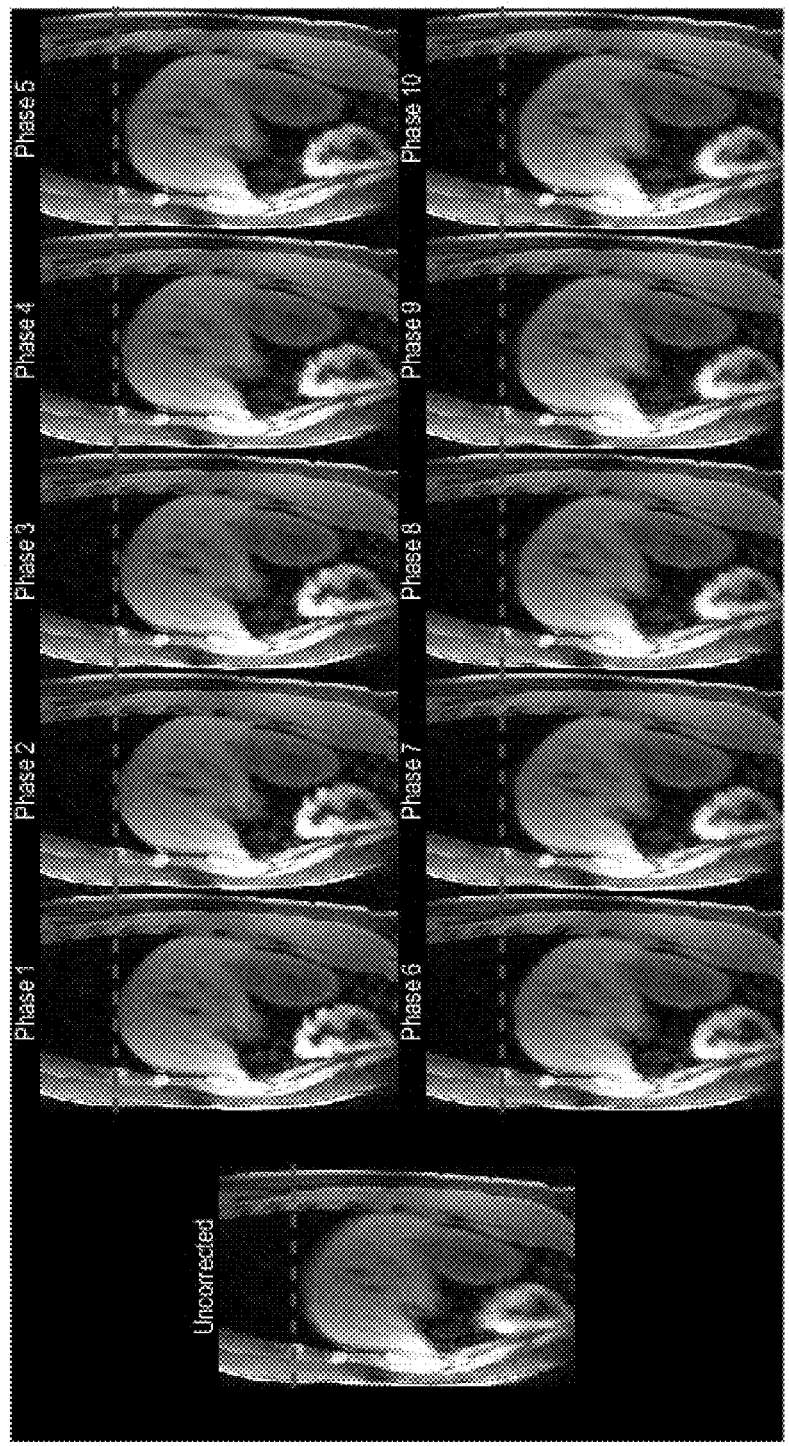
FIG. 22 is a series of images showing a sagittal view of a normal subject for a variety of conditions, including motion uncorrected and motion resolved for various phases of a respiratory cycle.
Figure 23:
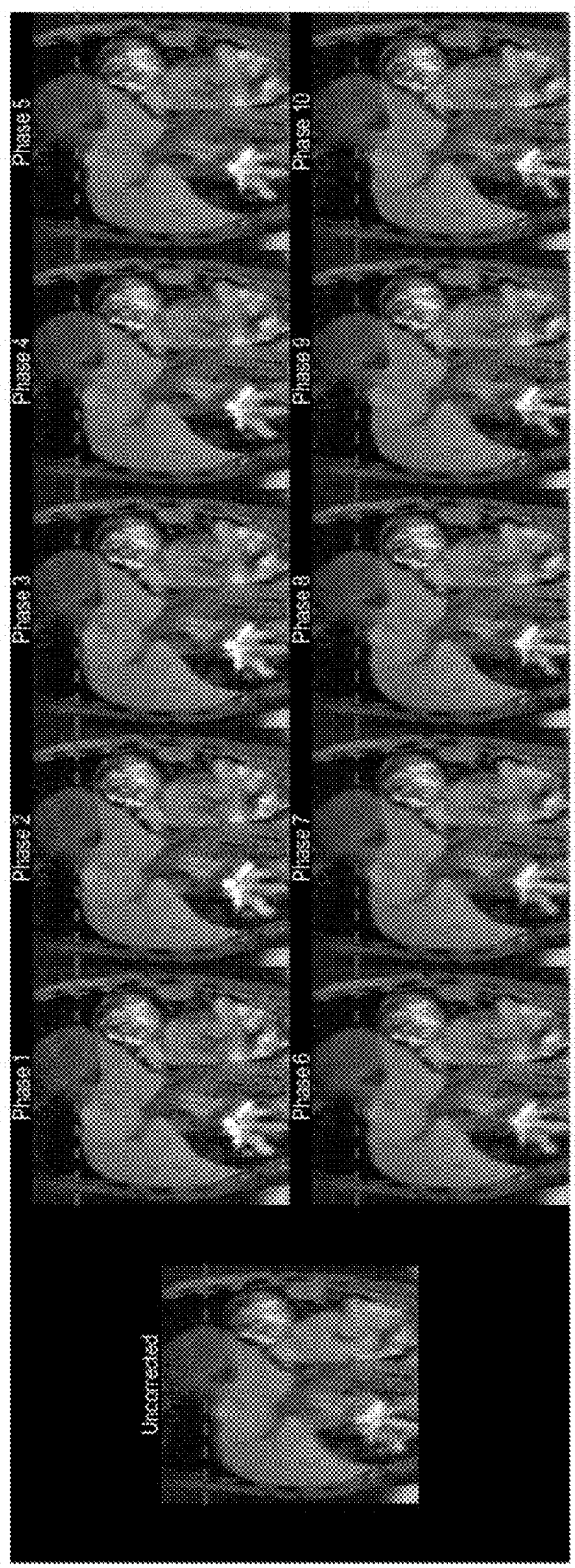
FIG. 23 is a series of images showing a coronal view of a normal subject for a variety of conditions, including motion uncorrected and motion resolved for various phases of a respiratory cycle.
Figure 24:
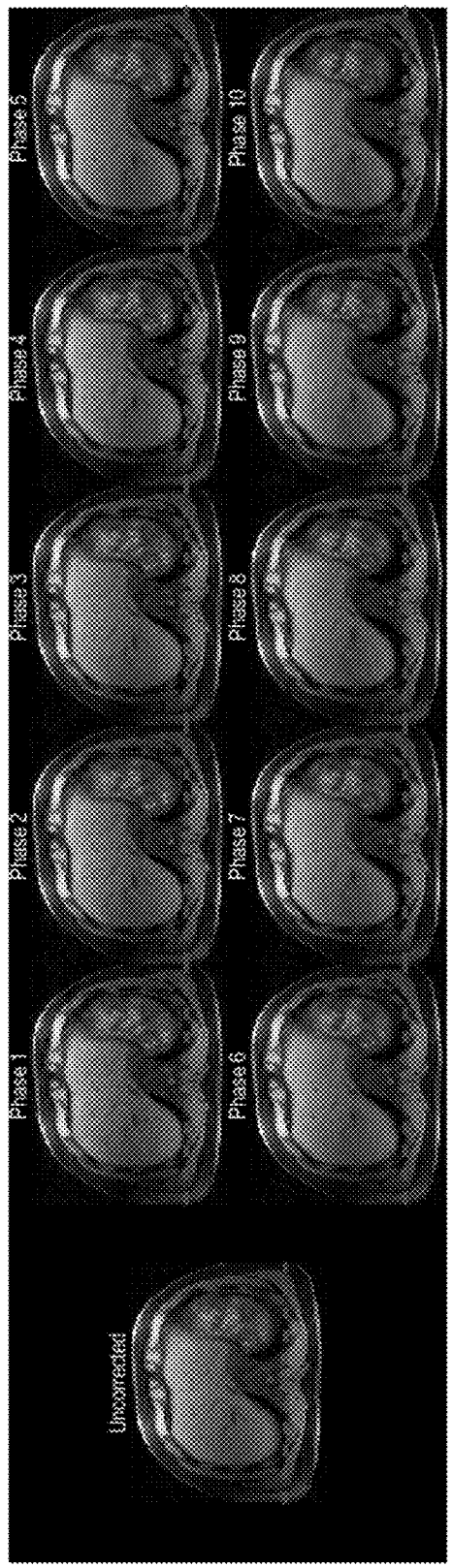
FIG. 24 is a series of images showing a transverse view of a normal subject for a variety of conditions, including motion uncorrected and motion resolved for various phases of a respiratory cycle.

As a demonstration of this ability, a volunteer was subjected to MR imaging as described herein above while performing a sequence of behaviors selected to produce a variety of motions. The volunteer was asked to breathe naturally, take a deep breath, return to natural breathing, and then hold breath. FIG. 19 is a map of the "tuned" navigator signal as described herein above with the automatically detected respiratory signal denoted as a superimposed red line. The method described herein above resulted in observable changes in the respiratory signal during the transition from natural breathing to deep breathing (marked by a red arrow in FIG. 19) and during the transition from normal breathing to breath holding (marked by a black arrow in FIG. 19). FIG. 19 confirms that the methods of motion resolution described herein are robust and capable of detecting a mixture of complex breathing patterns.

III. Self-Navigated MRI System

In various aspects, the 1D navigator motion resolution method described herein previously may be incorporated into any suitable MRI system to enable MR imaging on a free-breathing patient. In one aspect, the MRI system may use the 1D navigator imaging sequence of 1D navigator motion resolution method to reduce the artifacts induced by motion of the subject during MR scanning, thereby enhancing the quality of the MR image. In another aspect, the MRI system may use the CFM azimuth sampling scheme and the 1D navigator imaging sequence to further reduce artifacts. In yet another aspect, the MRI system may use the automated motion cycle detection using MR imaging data obtained using the 1D navigator imaging sequence to obtain a motion cycle used to group or bin subsets of the MR imaging data based on a phase of a motion cycle of the subject (i.e. a respiratory and/or cardiac motion cycles) to obtain MR images at discrete phases within the motion cycle of the subject with enhanced image quality.

The MRI system into which the CFM sampling scheme and/or the 1D navigator motion resolution method described herein may be incorporated may be any known suitable MRI system without limitation. In one non-limiting example, the MRI system may be a four-dimensional MR imaging (4DMRI) system that includes an MR imaging (MRI) device, a receiver, and a controller for operating and monitoring the elements of the MRI scanner. Typically, the MRI scanner may be configured to output a radio frequency (RF) signal to the receiver that, when processed by the controller, may be used to generate image data to be displayed to a user. In this example, the 4DMRI system may be configured to acquire and display MR imaging data obtained from a free-breathing patient characterized by movements associated with respiratory and/or cardiac motion. In an aspect, the controller may be further configured to condition the MR imaging data to reduce any artifacts introduced within the MR imaging data due to motion cycles and/or associated with the acquisition of the output signal by the MRI scanner as described herein previously.

In an aspect, the controller of the MRI system may be configured to acquire the output signal using a free-breathing, self-navigated MR data acquisition method with motion resolution. As defined herein, a "free-breathing" MR data acquisition method refers to a method of MR data acquisition in which a patient can freely breathe during MR scanning. Also as defined herein, a "self-navigated" MR data acquisition method refers to a method of MR data acquisition in which each MR data scan is associated with a phase within a motion cycle of the subject (e.g., a respiratory cycle) based on information within the output signal. As additionally defined herein, "motion resolution" refers to a method of processing MR data of a moving subject characterized by identifying a motion cycle of the subject during the acquisition of MR data, separating motion cycle into a plurality of motion phases, and optionally binning or grouping individual MR imaging scans according to the phase of the motion cycle during which each MR data scan was obtained.

FIG. 1 is a block diagram of a simplified MRI system 100 in one aspect. The MRI system 100 may include an MRI scanner 102, a gradient magnetic field amplifier 104, a transmitter 106, a receiver 1308, and a controller 110. In some aspects, the components of the MRI system 100 may be combined and/or separated in alternative arrangements. In other aspects, the MRI system 100 may include additional elements configured to provide support and/or additional capabilities for the elements of the MRI system 100 shown in FIG. 1.

Referring again to FIG. 1, the MRI scanner 102 may include at least one magnet (not shown) coupled to a plurality of coils (not shown). In an aspect, the MRI scanner 102 may include one magnet with a bore to house a patient (not shown). In some aspects, in which the MRI scanner 102 includes at least two magnets, the patient may be positioned between at least one pair of magnets. In various aspects, the coils may include a superconductive coil configured to produce a static magnetic field, an RF coil configured to produce an RF pulse, three gradient coils configured to produce a gradient magnetic field along each axis of the x-y-z grid, and a receiving coil (not shown) configured to capture the output MR signals of the MRI scanner 102. The gradient magnetic fields may be adjustable to collect output signals for a particular direction or angle relative to the x-y-z axes.

The gradient magnetic field amplifier 104 may be configured to couple to each gradient coil of the MRI scanner 102. The gradient magnetic field amplifier 104 may be configured to output an amplified gradient magnetic field signal to the gradient coils to induce the gradient magnetic fields. The transmitter 106 may be configured to couple to the RF coil to supply current to the RF coil of the MRI scanner 102 to generate RF pulses.

The receiver 108 may be configured to couple to the receiving coil to process the output signal of the MRI scanner 102. In an embodiment, the receiver 108 may be configured to periodically capture the output signal to be sent to the controller 110 for image processing. In other embodiments, the receiver 108 may be configured to capture the output signal in response to a trigger and/or a signal from controller 110.

The controller 110 may be configured to communicate with the gradient magnetic field amplifier 104, the transmitter 106, and the receiver 108 to send and receive data (e.g., image data) and control information (e.g., current monitoring). In some embodiments, the controller 110 may be configured to communicate with the MRI scanner 102 to monitor and/or to control the operation of the MRI scanner 102.

The controller 110 may include an acquisition unit 112, an image processing unit 114, a current control unit 116, a pulse control unit 118, at least one processor 120, and a memory 122. In the example embodiment, the controller 110 may be a computing device further including an operation unit 124 and a display unit 126. The at least one processor of the controller 110 may include the image processing unit 112, the acquisition unit 114, the current control unit 116, and/or the pulse control unit 118.

The acquisition unit 112 may be configured to control the gradient magnetic field amplifier 104 to adjust a direction or orientation of the output signal collected by the MRI scanner 102. More specifically, the acquisition unit 112 may be configured to control the gradient magnetic field amplifier based on a stack-of-spokes acquisition method described herein previously. In at least some embodiments, the acquisition unit 112 may be configured to receive the output signals for analysis prior to transmitting the output signals to the image processing unit 112. In other embodiments, the acquisition unit 112 may be configured to transmit acquisition data associated with the output signals to the image processing unit 112.

The image processing unit 114 may be configured to receive the output signal to produce an image to be displayed. In the example embodiment, the image processing unit 114 may be configured to process the output signal as frequency data to remove non-physiological components from the output signal and/or to determine a phase of a motion cycle associated with the output signal. The image processing unit 114 may be configured to generate MR image data based on the frequency data of the output signal. In an aspect, the MR image data may be used to reconstruct three-dimensional images of an imaging volume (e.g., a patient) over time to facilitate identifying and analyzing motion within the imaging volume. Additionally, the image processing unit 114 may be configured to provide additional display options at the display unit 125 such as three-dimensional (3D) models of images and time-lapsed videos.

The current control unit 116 may be configured to regulate the input current of the gradient magnetic field amplifier 104 and the transmitter 106 to facilitate currents within the current ratings of each component. In some embodiments, the current control unit may be configured to monitor electric current data received from the MRI system 100.

The pulse control unit 118 may be configured to communicate with the transmitter 106 to generate RF pulses within the MRI scanner 102 to create the output signal received by the receiver 108. In some embodiments, the pulse control unit 118 may be configured to communicate with the gradient magnetic field amplifier 104 to monitor and/or control the gradient magnetic field signals sent to the MRI scanner 102.

Processor 120 may include any type of conventional processor, microprocessor, or processing logic that interprets and executes instructions. Processor 120 may be configured to process instructions for execution within the controller 110, including instructions stored in the memory 122 to display graphical information for a GUI on an external input/output device, such as display 126 coupled to a high speed interface. In other implementations, multiple processors and/or multiple buses may be used, as appropriate, along with multiple memories and types of memory. Also, multiple controllers 110 may be connected, with each device providing portions of the necessary operations (e.g., as a server bank, a group of blade servers, or a multi-processor system). In some embodiments, the processor 120 may include the acquisition unit 112, the image processing unit 114, the current control unit 116, and/or the pulse control unit 118.

The memory 122 facilitates data storage in the MRI system 100. In some embodiments, the memory 122 includes a plurality of storage components such as, but not limited to, a hard disk drive, flash memory, random access memory, and a magnetic or optical disk. Alternatively or additionally, the memory 122 may include remote storage such as a server in communication with the controller 110. The memory 122 stores at least one computer program that, when received by the at least one processor, cause the at least one processor to perform any of the functions of the controller 110 described above. In one implementation, the memory 122 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more functions, such as those described herein. The information carrier may be a non-transitory computer- or machine-readable medium, such as the memory 122 or memory on the processor 120. Additionally, the memory 122 may be configured to facilitate storage of a plurality of images from the MRI scanner 102 as processed by the controller 110.

The operation unit 124 may be configured to enable a user to interface (e.g., visual, audio, touch, button presses, stylus taps, etc.) with the controller 110 to control the operation of the MRI system 100. In some embodiments, the operation unit 124 may be further coupled to the MRI scanner 102 to control the operation of the MRI scanner 102.

The display unit 126 may enable a user to view data and control information of the MRI system 100. The display unit 126 may further be coupled to other components of the MRI system 100 such as the MRI scanner 102. The display unit 126 may include a visual display such as a cathode ray tube (CRT) display, liquid crystal display (LCD), light emitting diode (LED) display, or "electronic ink" display. In some embodiments, the display unit 315 may be configured to present a graphical user interface (e.g., a web browser and/or a client application) to the user. A graphical user interface may include, for example, an image display for images acquired by the MRI system 100 of a patient, operational data of the MRI system 100, and the patient's physiological data (e.g., heart rate).

In the example embodiment, controller 110 may be configured to acquire frequency data associated with the imaging volume using a 1D navigator imaging sequence. In particular, controller 110 may be configured to collect radial frequency data for different azimuthal angles along the $k_x$-$k_y$ plane within k-space. When viewed graphically, each radial line for an azimuthal angle may be a spoke of a "star" formed by the spokes for the plurality of azimuthal angles. Additional spokes of frequency data are collected along the $k_z$ axis at one azimuthal angle to form a stack of spokes, and the stack of spokes may be combined to form the stack of stars.

To reduce the effect of noise or signal variations induced by breathing or the MRI scanner 102 (e.g., eddy currents and the like) on the MR image data, the controller 110 may be configured to (i) define a one dimensional navigator spoke within the frequency data that facilitates determining a motion phase associated with the output signal, and (ii) calculate an azimuthal angle for the radial acquisition of frequency data using a controlled frequency modulation that displaces non-physiological signal variations within the frequency domain to a region outside of the frequency range(s) associated with physiological motion within the imaging volume. Accordingly, the controller 110 may be configured to facilitate improved MR image clarity and improved identification of motion phases within a motion cycle.

As used herein, a processor such as the processor 120 may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As described herein, computing devices and computer systems include a processor and a memory. However, any processor in a computer device referred to herein may also refer to one or more processors wherein the processor may be in one computing device or a plurality of computing devices acting in parallel. Additionally, any memory in a computer device referred to herein may also refer to one or more memories wherein the memories may be in one computing device or a plurality of computing devices acting in parallel.

In various aspects, the controller 110 may be configured to perform the CFM sampling scheme described herein to reduce physiologically irrelevant signal variations and/or to implement the 1D navigator motion resolution method described herein during MR data acquisition to accurately bin the acquired data into motion phases. Once the MR data has been acquired and tagged with a particular motion phase, the controller 110 may be configured to generate motion-corrected MR images from the acquired data. In one example, the data may be used to generate a four-dimensional MR image set that includes a plurality of 3D spatial images in which each 3D spatial image is associated with a different phase within a motion cycle of the subject) for analyzing motion within the imaging volume. Based on the motion captured within the four-dimensional MR image set, a user may determine and/or identify any potential issues or other points of interest from the images.

EXAMPLES

The following examples illustrate various aspects of the disclosure.

Example 1: MR Imaging of Respiratory Image Phantom

To assess the effect of data acquisition and motion resolution methods under controlled conditions, the following experiments were conducted.

Figures 11A, 11B, 11C:
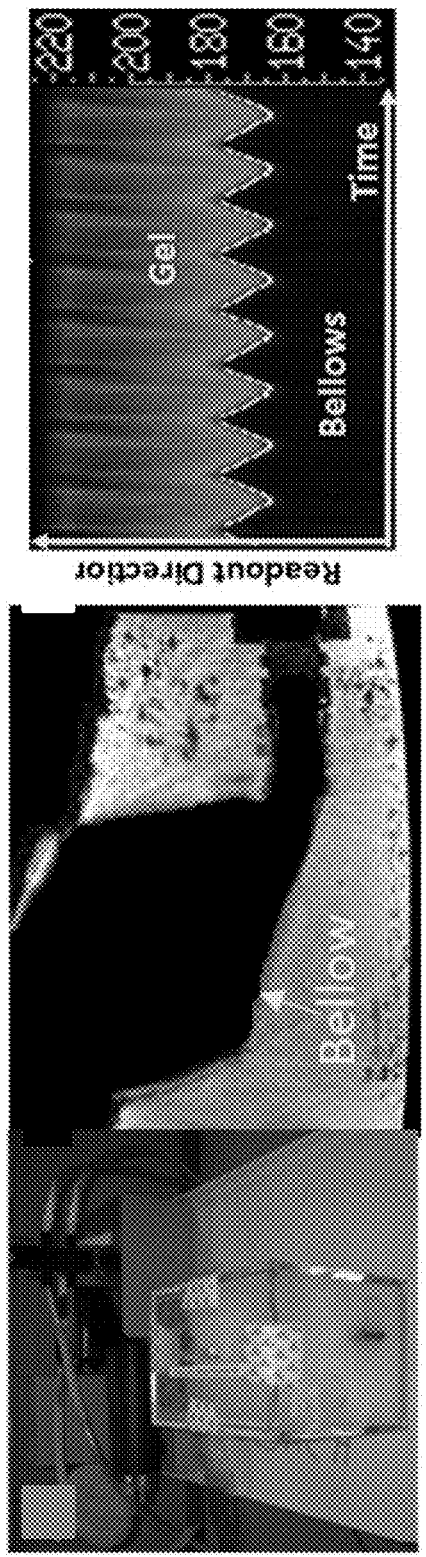
FIG. 11A is a photograph of a respiratory motion phantom.
FIG. 11B is a MR image of the respiratory motion phantom shown in FIG. 11A.
FIG. 11C is a map of pencil beam MRI navigator echoes obtained during multiple motion cycles of the respiratory phantom shown in FIG. 11A.

A respiratory motion phantom referred to herein as "Chest-R" was constructed as shown in the photograph of FIG. 11A. Chest-R included a bellow that was inflated and deflated by an adjustable ventilator pump (Model 607, Harvard Apparatus) with adjustable frequency and amplitude outputs. As shown in FIG. 11A, the bellow, which consisted of a 0.5 L neoprene ventilation bag was immersed in a sodium polyacrylate (~10 g/L) gel. The bellow's inflation and deflation cycle was modulated by varying the impedance between the ventilator pump and the bellow using variable diameter and length tygon tubing. Neoprene pockets were attached to the bellows to permit the insertion of PET phantoms for PET/MR simulations. Chest-R was configured to generate deformable motion that resembled respiratory motion.

The Chest-R phantom was subjected to MR imaging using a pencil beam excitation method and a 1D self-navigated MR data acquisition method. The 1D navigator method as described above was used to derive a respiratory motion cycle for Chest-R. FIG. 11C is an image of the map of the phase of the inverse Fourier transform of the MR data associated with the 1D navigator spoke as a function of distance along the image axis corresponding to the 1D navigator direction in k-space (vertical axis) as well as data acquisition time (horizontal axis). As shown in FIG. 11C, excellent contrasts in the phase map were achieved, and a respiratory curve was extracted as described herein above. FIG. 11B is a representative image reconstructed from the MR imaging data acquired in this experiment.

Figures 12A, 12B, 12C:
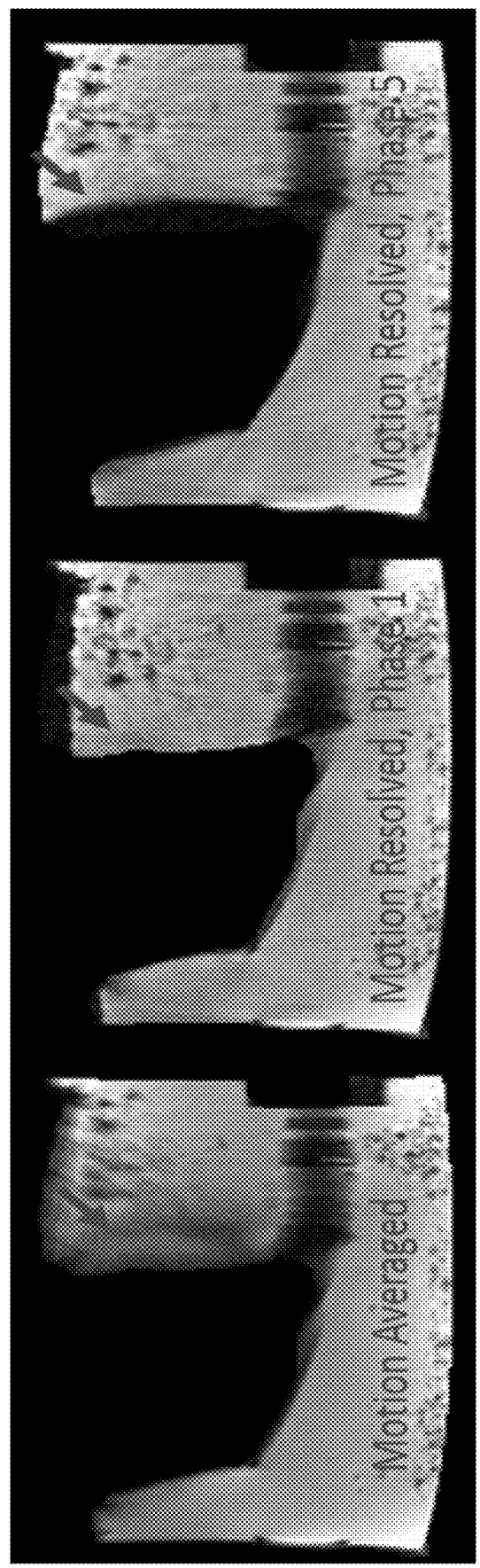
FIG. 12A is a motion-averaged MR image of the respiratory phantom shown in FIG. 11A.
FIG. 12B is a motion-corrected image of the respiratory phantom shown in FIG. 11A at Phase 1 of the simulated respiratory motion.
FIG. 12C is a motion-corrected image of the respiratory phantom shown in FIG. 11A at Phase 5 of the simulated respiratory motion.

The motion cycle of the Chest-R phantom derived from the phase map shown in FIG. 11C was binned into five phases, and all MR imaging data was subdivided according to the phase within the motion cycle at which each MR data scan was conducted as described herein above. All MR imaging data was combined to produce a motion averaged MR image of the Chest-R phantom as shown in FIG. 12A. In addition, MR imaging data corresponding to Phase 1 and to Phase 5 were grouped and analyzed according to the 1D navigator motion resolution method described herein above to produce the motion-resolved MR images of FIG. 12B and FIG. 12C, respectively. Comparing the regions of each MR image marked by the arrows in FIGS. 12A, 12B, and 12C, the 1D navigator motion resolution method was effective in correcting motion in a respiratory motion phantom.

Example 2: Effect of Motion Correction on In Vivo MR Signal Spectra

To assess the effect of motion correction on in vivo MR signal spectra, the following experiments were conducted.

The Chest-R phantom was subjected to MR imaging in a manner similar to the methods described in Example 1 to derive a respiratory motion cycle using the self-navigated respiratory correction methods described above in various aspects. The Chest-R phantom was imaged during six different simulated respiratory cycles characterized by three different motion frequencies of 10, 20, and 30 rpm and two air volumes of 400 and 600 cc, making for six different settings, were tested. The MRI acquisition parameters were as follows: TE/TR=1.99 ms/3.84 ms, matrix size=320×320, field of view (FOV)=240 mm×240 mm, slab thickness=163.2 mm, number of partitions=48, partial Fourier factor=6/8, reconstructed slices per slab=96 (yielding a slice thickness of 1.7 mm). The resulting voxel size for the phantom study was 0.75×0.75×1.7 mm$^3$. Static imaging was also performed to obtain a reference image sharpness at an air-gel interface.

Figure 25A:
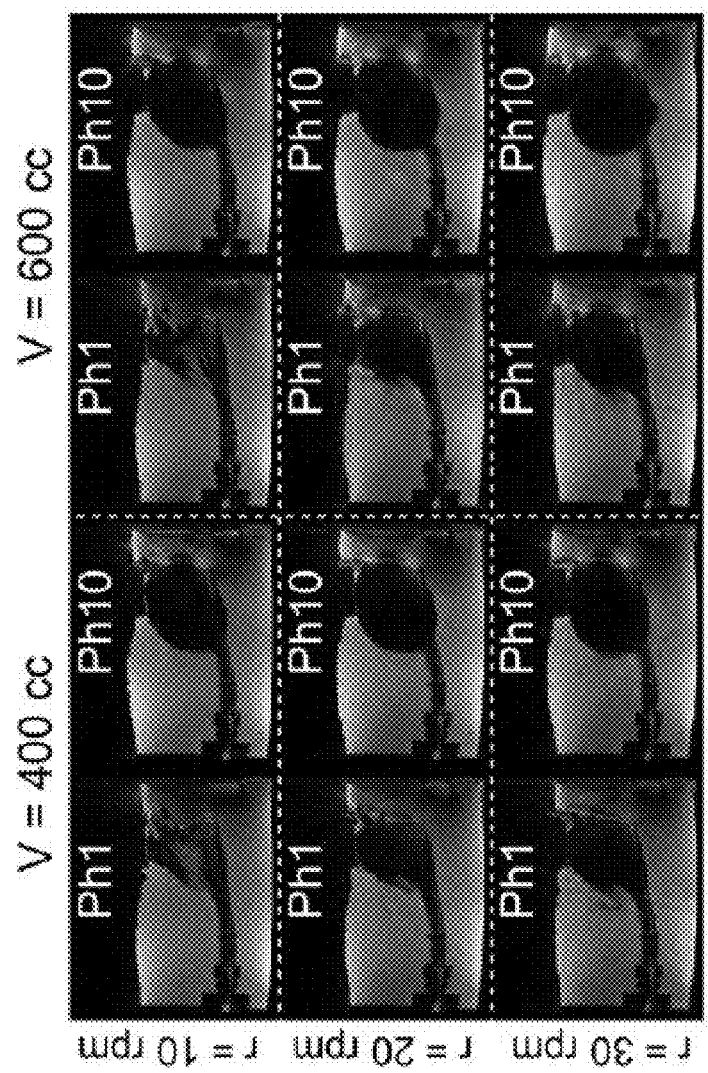
FIG. 25A is a series of images showing first and last respiratory phases for a respiration phantom under six different motion settings, motion frequencies being 10, 20, or 30 rpm and volume being 400 or 600 cc.
Figure 25B:
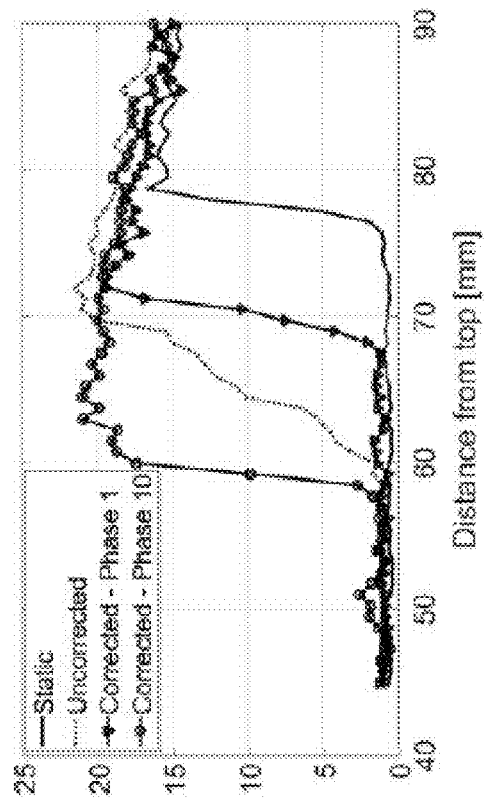
FIG. 25B is a graph and a series of images, the graph showing averaged intensity profiles from a location of an air-gel interface for a largest-volume highest-speed setting, and the series of images showing where the averaging was performed indicated by a white band in FIG. 25C.
Figure 25C:
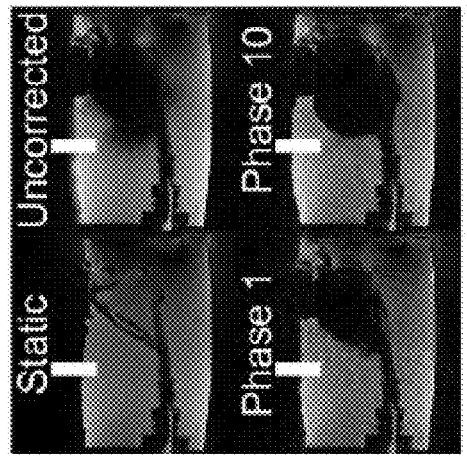
FIG. 25C is a series of images showing first and last respiratory phases for a respiration phantom under motion settings that included a motion frequencies of 30 rpm and a volume of 600 cc.

FIG. 25A shows static images of first and last phases for the Chest-R phantom motion cycles using the six different motion settings described above. Line profiles across the air-gel interface were used to assess performance. Apparent slopes were measured for the line profiles to serve as a metric for the adequacy of motion correction. Averaged intensity profiles from the same location of the air-gel interface for the largest-volume highest-speed setting (V=600 cc, r=30 rpm) are shown in FIG. 25B. The averaging was performed across 15 adjacent profiles indicated by white bands shown in FIG. 25C. FIG. 25B shows the line profile plots across the air-gel interface obtained from the static image, the uncorrected image of the moving phantom, the motion-corrected Phase 1 image, and the motion-corrected Phase 10 image. As shown in FIG. 25B, the apparent slopes across the air-gel interface of the line profiles obtained from the static image, motion-corrected Phase 1 image, and motion-corrected Phase 10 are more clearly defined than the apparent slope of the line profile from the uncorrected image. The apparent slope across the air-gel interface was diminished to 36% of the static case in the motion-uncorrected image and was recovered to 78% of the static case in the motion-corrected images, showing that motion correction leads to higher quality images.

The results of these experiments demonstrated that respiratory motion correction successfully resolved and corrected for respiratory motion for various respiratory cycles.

Example 3: Effect of Phase Tuning on Respiratory Motion Detection

To assess the effect of phase tuning on respiratory motion detection, the following experiments were conducted.

One healthy subject was subjected to two MR imaging scans using two different single-slice gradient recalled echo (GRE) sequences. The first GRE protocol was as follows: TE/TR=3.1 ms/5.6 ms, slice thickness=3 mm, matrix size=192×126, in-plane resolution=1.56×1.56 mm, number of sequence repetitions=500, and total scan time=67 seconds. The acquisitions were sagittal with the readout axis lying along the SI axis of the subject. Generalized autocalibrating partially parallel acquisitions (GRAPPA) was used for accelerating the acquisition so that each image could be acquired in 134.4 ms. In this time period, it was possible to observe the motion of the liver during respiration. The second GRE protocol was similar to the first protocol except that the slice thickness was set to 250 mm, rather than 3 mm.

The thick-slice acquisition of the second scan yielded a projection of the signals within a large spatial region onto the sagittal plane and was useful in mimicking the projections used by the image motion-correction system disclosed above. The thin-slice acquisition provided a better visualization of the liver's anatomical location along the SI axis. Both sets of GRE scans were reconstructed into complex images for each receiver channel of the system and phase tuning was applied to observe the variations in signal intensities. Those SI projections corresponding to projections of CAPTURE were obtained by taking the inverse FT of the central k-space lines of the thick-slice GRE data after apodization. Data obtained from the middle spine coil element is shown below.

Figure 26A:
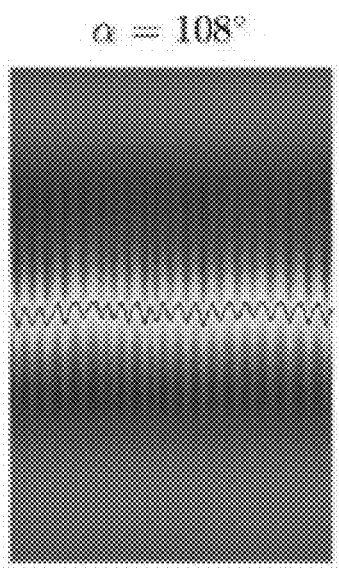
FIG. 26A is an image showing phase-tuned real parts of projections using an appropriate tuning angle of 108 degrees.
Figure 26B:
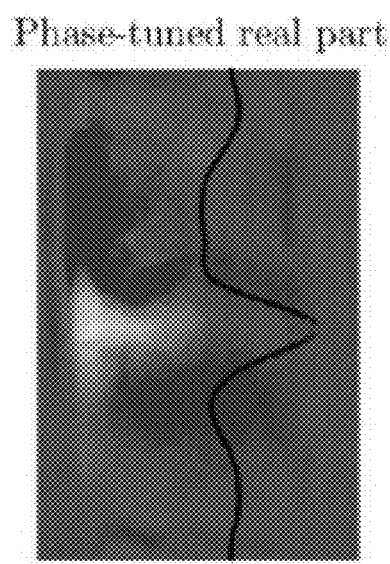
FIG. 26B is an image showing the phase-tuned real part images from a single sequence repetition of a thick-slice gradient recalled echo (GRE) acquisition with overlaid black curves corresponding to projections for that particular sequence repetition and red asterisk corresponding to a peak of the projection obtained using an appropriate tuning angle of 108 degrees.
Figure 26C:
FIG. 26C is a thin-slice GRE image providing an anatomical reference for the images of FIG. 26A and FIG. 26B.

The data from a middle spine coil element of an MRI imaging system is shown in FIGS. 26A, 26B, 26C, 26D, 26E and 26F. FIG. 26A shows the phase-tuned real part images of the projections, with the overlaid red curves showing the detected respiratory motion curves obtained by peak detection, using a suitable tuning angle of 108 degrees. FIG. 26B shows phase-tuned real part images from a single sequence repetition of the thick-slice GRE acquisition, and the overlaid black curves are the corresponding projections for that particular sequence repetition with the red asterisk indicating the peak of the projection. FIG. 26C is a thin-slice GRE image that provide anatomical reference for FIG. 26A and FIG. 26B.

Figure 26D:
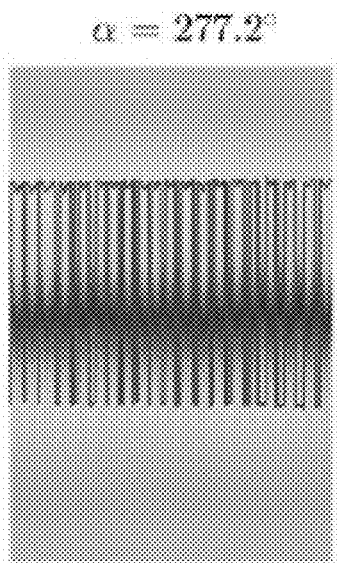
FIG. 26D is an image showing phase-tuned real parts of projections using a poor tuning angle of 277.2 degrees.
Figure 26E:
FIG. 26E is an image showing the phase-tuned real part images from a single sequence repetition of a thick-slice gradient recalled echo (GRE) acquisition with overlaid black curves corresponding to projections for that particular sequence repetition and red asterisk corresponding to a peak of the projection obtained using a poor tuning angle of 277.2 degrees.
Figure 26F:
FIG. 26F is a thin-slice GRE image providing an anatomical reference for the images of FIG. 26D and FIG. 26E.

FIG. 26D shows the phase-tuned real part image of the projection, with the overlaid red curves showing the detected respiratory motion curves obtained by peak detection, using a poor phase tuning angle of 277.2 degrees. FIG. 26E shows phase-tuned real part images from a single sequence repetition of the thick-slice GRE acquisition, and the overlaid black curves are the corresponding projections for that particular sequence repetition with the red asterisk indicating the peak of the projection, using a poor phase tuning angle of 277.2 degrees. FIG. 26F is a thin-slice GRE image that provide anatomical reference for FIG. 26D and FIG. 26E.

Similarly, FIG. 35A and FIG. 35C are maps of the real part image of the projection obtained without (FIG. 35A) and with (FIG. 35C) phase tuning, with the overlaid red curves showing the detected respiratory motion curves obtained by peak detection. FIGS. 35B and 35D are the spectra corresponding to FIG. 35A and FIG. 35C, respectively, demonstrating that phase-tuning enhances the capture of respiration-related spectral content.

The results of these experiments demonstrated that phase tuning the real part operator selectively highlights different parts of the body for different phase rotation angles and can be made to selectively highlight an anatomical region that moves significantly with respiration. FIG. 26A shows an example of where the highlighted region forms a bright band on the liver area, an area that moves with respiration. FIG. 26B shows an example of where the highlighted region does not move with respiration and in which case the detected respiratory motion curve does not represent respiration. These experiments also show why the ordinary real part and imaginary part operators fail to work in some cases because subjects and imaging systems vary so greatly from one another.

Example 4: Effect of Motion Correction on In Vivo Image Quality

To assess the effect of motion correct on in vivo image quality, the following experiments were conducted. Motion-corrected and uncorrected images were arranged side-by-side in a pairwise fashion with left-right randomization for each image pair. Two radiologists, each blinded to the motion-corrected versus uncorrected datasets, reviewed and rated the image pairs independently using a Likert scale of 1-5 (1=Very blurry, 2=Blurry, 3=Intermediate, 4=Sharp, 5=Very sharp). The radiologists assessed the largest liver finding for patients with liver tumors. For both healthy patients and patients with liver tumors, the radiologists assessed the largest portal vein and the lung-liver interface. For each radiologist, differences between motion-corrected and uncorrected image quality were statistically assessed using the signed rank test.

Figure 27:
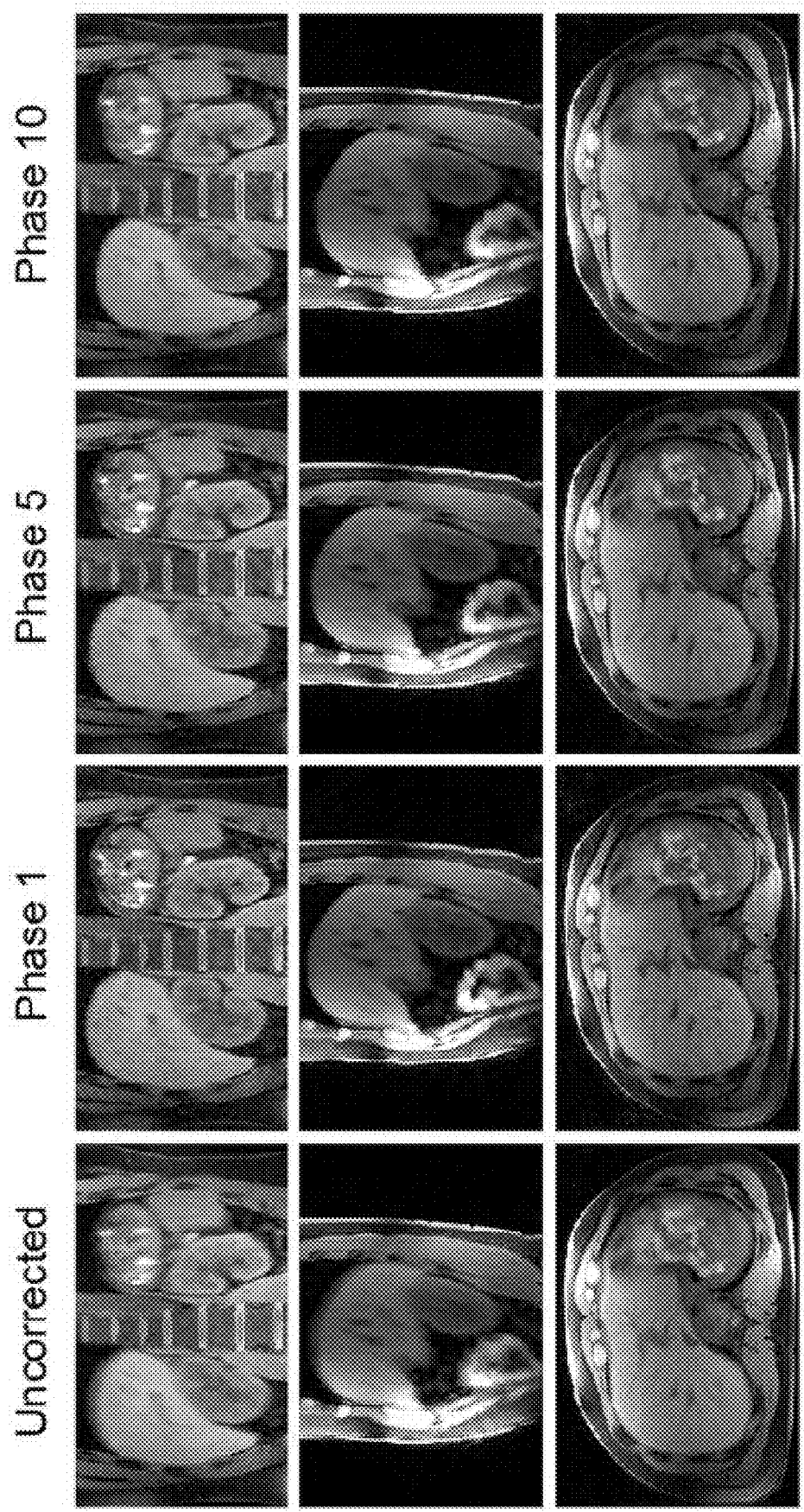
FIG. 27 is a series of images showing uncorrected images and three representative respiratory phases from a motion-corrected database of a healthy subject in coronal, sagittal, and transversal views.
Figure 28B:
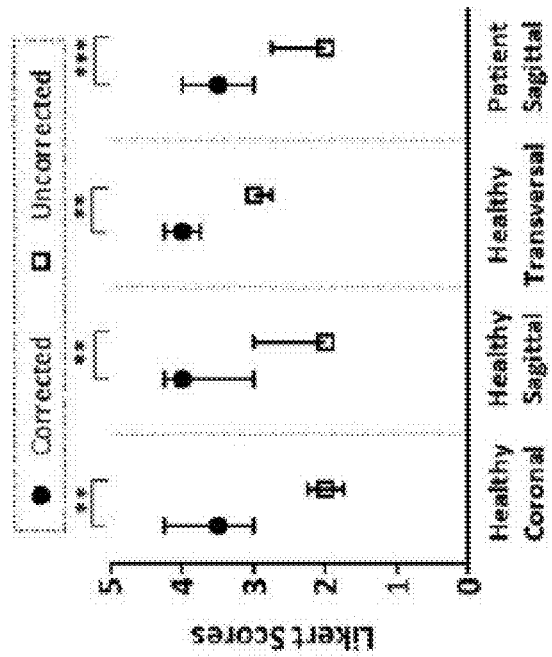
FIG. 28B is a chart representing medians and interquartile ranges of Likert scores given by a second rater for image quality of the images shown in FIG. 27 and FIG. 31.
Figure 28A:
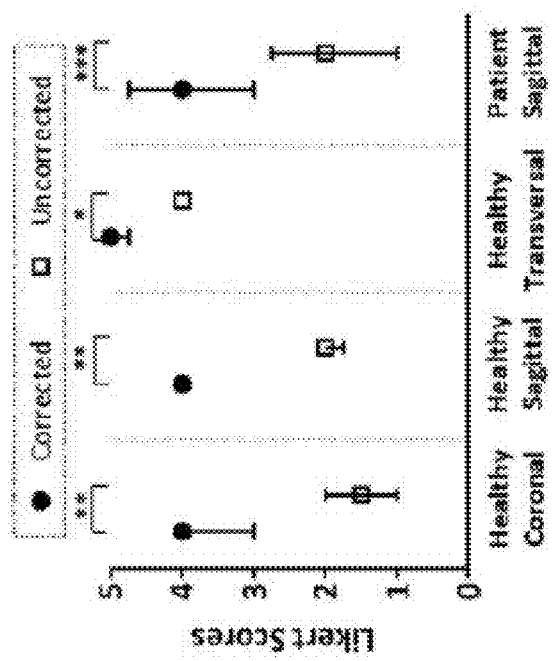
FIG. 28A is a chart representing medians and interquartile ranges of Likert scores given by a first rater for image quality of the images shown in FIG. 27 and FIG. 31.

FIG. 27 shows the images that were ranked by the radiologists, which included one set of uncorrected images and three sets of three representative respiratory phases of motion-corrected images. FIG. 28A and FIG. 28B show the medians and interquartile ranges of the Likert scores given by the two radiologists. Both radiologists typically scored the motion-corrected images at higher scores than the uncorrected images.

For the healthy volunteers, the first radiologist scored the motion-corrected images as higher image quality for all coronal and sagittal image sets, and for 7 of 10 transverse image sets; for the remaining 3 cases the motion-corrected and uncorrected images were scored equally with Likert scores nearly equal to the maximum attainable Likert score. The second radiologist assigned higher Likert scores for all motion-corrected images of the healthy volunteers in all three image orientations. For the liver tumor patients, the first radiologist scored the motion-corrected images as higher image quality in 11 out of 12 cases; for the remaining case, the motion-corrected and uncorrected images were scored equally, with Likert scores equal to the maximum attainable Likert score. The second radiologist scored higher image quality for all motion-corrected images of the liver tumor patients in all three image orientations.

A statistical assessment indicated that the motion-corrected images attained significantly higher image quality scores from both radiologists in both the healthy volunteer and the liver tumor patient populations, as summarized in FIG. 28A and FIG. 28B. The improvement in the median Likert scores due to motion-correction of the image ranged from 1 to 2 points across all image pairs.

The results of these experiments demonstrated that the motion-corrected images were of higher quality than uncorrected images. The motion-corrected image quality was enhanced relative to the uncorrected image independently of image orientation.

Example 5: Detection of Respiratory Cycles with Variations in Cycle Characteristics To assess the detection of respiratory cycles with variations in cycle characteristics, the following experiments were conducted.

Figure 29:
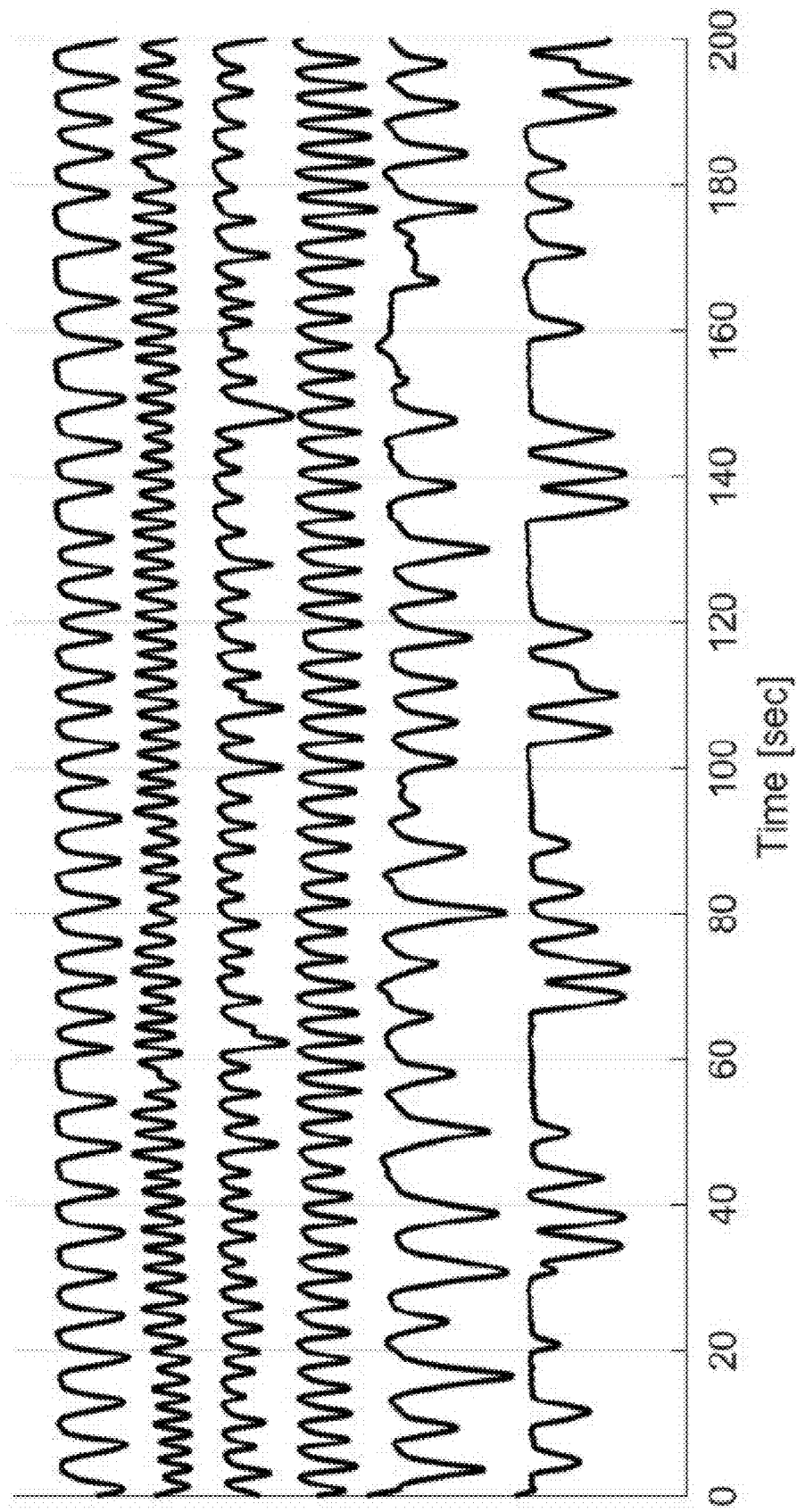
FIG. 29 is a graph showing, detected respiratory curves from three healthy subjects and three liver tumor patients, arranged from top to bottom.

To assess the degree of respiratory cycle variation between individuals, as well as variation by an individual, during an MR imaging session, the respiratory patterns detected using the methods described herein for three healthy volunteers and for three liver cancer patients were compared, as illustrated in FIG. 29. The respiratory motion patterns differed significantly between all patients and even within given patients within the same imaging session.

Figure 30:
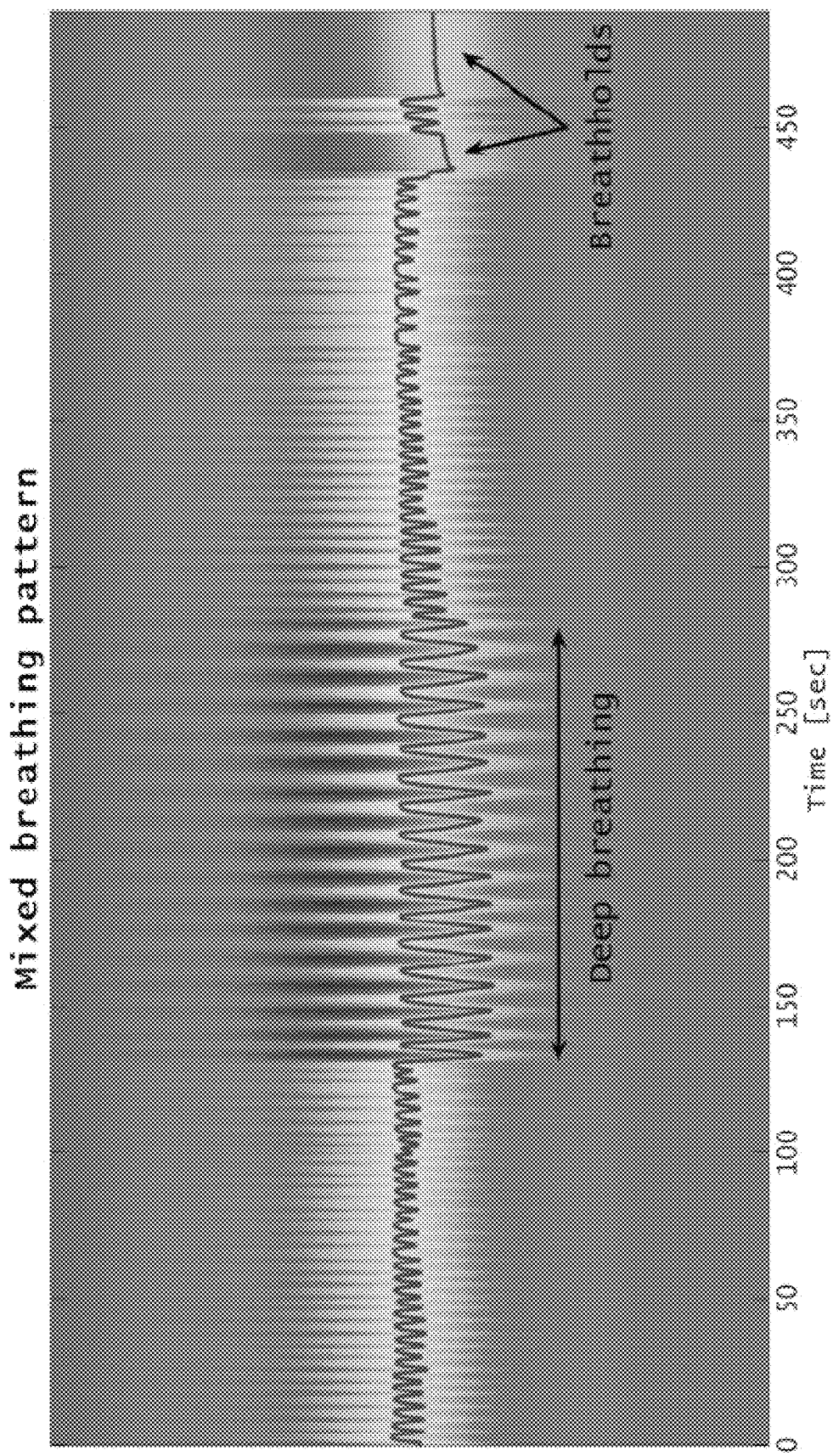
FIG. 30 is a graph showing a detected respiratory curve for a healthy subject with a varied breathing pattern.

To assess the robustness of the method for detecting respiratory cycle described herein, one healthy volunteer was instructed to intentionally modify breathing behavior during an imaging session. The modified breathing pattern included additional patterns such as deep breathing and breath holding, as illustrated in FIG. 30.

The results of these experiments demonstrated that the methods described herein successfully extracted respiratory content from all volunteer and patient datasets in a fully-automated manner despite the high variability in respiratory patterns. The disclosed method adapts to the unique characteristics of each participant's respiratory pattern, as demonstrated by the wide range of optimal phase rotation angles and coil elements among a group of twelve patients summarized in Table 1. As illustrated in FIG. 30, the disclosed method successfully extracted respiratory content from the imaging dataset of the patient instructed to deliberately change breathing pattern as described above.

TABLE 1

Optimal coils and phase rotation angles identified by an automated phase tuning method for 12 patient participants.

|  | Sagittal | |
| --- | --- | --- |
|  | Coil | Angle |
| Patient 1 | SP2 | 334.8° |
| Patient 2 | SP3 | 237.6° |
| Patient 3 | SP3 | 241.2° |
| Patient 4 | SP4 | 356.4° |
| Patient 5 | BO2 | 190.8° |
| Patient 6 | SP2 | 72.0° |
| Patient 7 | SP3 | 280.8° |
| Patient 8 | SP3 | 32.4° |
| Patient 9 | SP3 | 338.4° |
| Patient 10 | SP1 | 133.2° |
| Patient 11 | BO2 | 180.0° |
| Patient 12 | SP5 | 39.6° |

BO2 denotes an element of a flex body coil placed on the patient's chest; SP1-SP5 denote elements of the spine coil positioned in the scanner table adjacent to the patient's spine.

Example 6: Effect of Motion Correction on In Vivo Detection of Liver Lesions Using MR Imaging To assess the effect of motion correction on the in vivo detection of liver lesions using MR imaging, the following experiments were conducted.

Twelve patients previously diagnosed with various liver tumors were imaged using methods similar to those described above. Six patients were previously diagnosed with primary hepatic malignancies, and the other six patients were previously diagnosed with metastatic disease from an extrahepatic primary. The MR images were acquired on the sagittal plane using imaging parameters similar to those used for healthy volunteers as described above except for an increase in the number of slices in several patients for enhanced spatial coverage, and an increase of in-plane resolution from 0.8 mm to 1.125 mm for one patient. A scan for one patient was terminated early, resulting in acquisition of 82% of the specified imaging dataset for one patient. Motion-corrected and uncorrected images were rated by two radiologists using the methods similar to the methods of Example 4.

Figure 31:
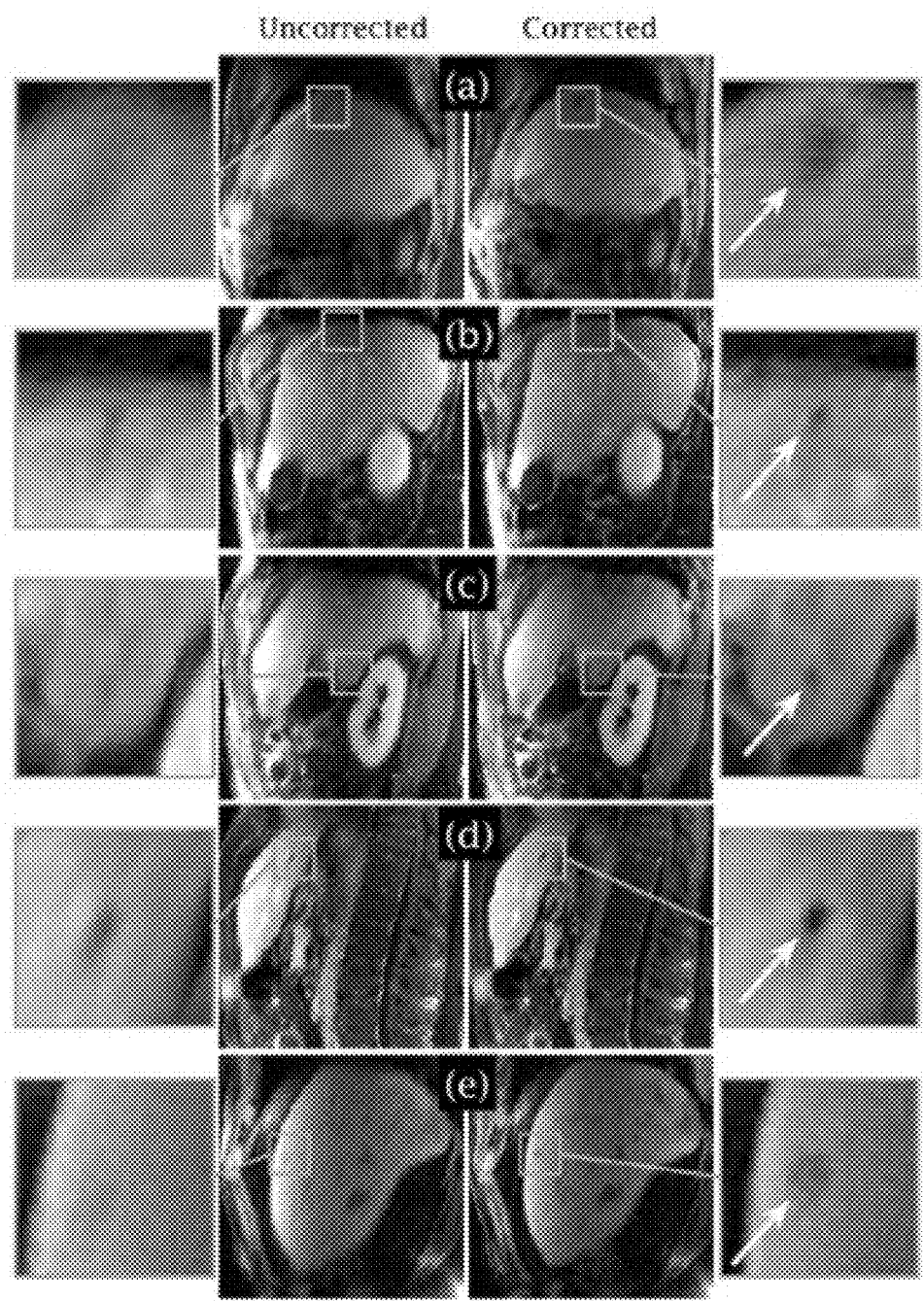
FIG. 31 is a series of images showing five representative slices of liver images obtained from three liver tumor patients. Each image slice is shown uncorrected (left column) and motion-corrected (right column) with enlargements of all images provided; white arrows mark improvements in motion-corrected image quality of small lesions.

A representative sample of images scored by the radiologists is shown in FIG. 31. The imaged lesions were rendered more conspicuous after motion-correction of the images. Smaller lesions of less than 1 cm in size were significantly obscured by motion artifacts in the uncorrected images, but were depicted clearly in the corresponding motion-corrected images. As described in Example 4, the radiologists rated the corrected images at a significantly higher image quality score than the uncorrected images.

The results of these experiments demonstrated that motion correction increases the in vivo detection of liver lesions. Small liver lesions depicted very clearly in the motion corrected images, and the overall score of image quality of the corrected images was significantly higher in these patients than the uncorrected images.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for producing motion-corrected MR images of at least a portion of a patient, the system including:
    an MRI scanner comprising a plurality of coils, the plurality of coils configured to detect a plurality of MR imaging datasets, each MR imaging dataset comprising a plurality of MR signals detected by one coil of the plurality of coils;
    a controller operatively coupled to the MRI scanner, the controller comprising:
        at least one processor and a non-volatile memory;
        a current control unit and a pulse control unit operatively coupled to the MRI scanner, wherein the current control unit and the pulse control unit are configured to operate the MRI scanner to detect the plurality of MR imaging signals according to a 1D navigator imaging sequence; and
    an image processing unit operatively coupled to the MRI scanner, the image processing unit configured to:
        receive the plurality of MR imaging datasets associated with the plurality of coils;
        identify a motion cycle using an automated motion detection method, the motion cycle comprising a plurality of phases; and
        partition the plurality of MR imaging datasets into a plurality of image groups, each image group comprising a portion of the plurality of MR imaging datasets associated with one of the phases of the motion cycle, wherein:
    the 1D navigator imaging sequence comprises obtaining a plurality of scans, each scan comprising a 1D navigator spoke coincident with a fixed $k_x$ axis in k-space obtained prior to a corresponding stack of spokes distributed along a $k_z$ axis and oriented along an azimuth angle in k-space, and further comprises incrementally changing the azimuth angle prior to obtaining an additional scan,
    the 1D navigator imaging sequence further comprises incrementally changing the azimuth angle according to an azimuth sampling scheme selected from the group consisting of a Golden Angle azimuth sampling scheme and a controlled frequency modulation azimuth sampling scheme, and
    the automated motion detection method further comprises:
        for each MR imaging dataset, obtaining an inverse Fourier transform each 1D navigator associated with each stack of spokes,
        for each MR imaging dataset, arranging each inverse Fourier transform into a 2D matrix $P_i = P_i[x, n]$ wherein i is a coil index indicative of the coil associated with the MR imaging dataset, x is a position index indicative of a position of the inverse Fourier transform along a spatial X axis, the spatial X axis comprising the inverse Fourier transform of the $k_x$ axis, and n is a discrete time index indicative of a time of data acquisition,
        tuning each 2D matrix $P_i$ to identify an optimal coil i* and an optimal phase angle m*, based on a temporospectral quality metric, and
        obtaining a motion curve $r_{i,m}[n]$ by detecting the location of each peak along each column of an optimum 2D matrix $P_i$, the optimum 2D matrix $P_i$ comprising a 2D matrix $P_i$ corresponding to the optimal coil i* and phase-rotated by the optimal phase angle m*.

2. The system of claim 1, wherein tuning each 2D matrix $P_i$ to identify an optimum coil i* and an optimum phase angle m* further comprises:
    phase-rotating each 2D matrix $P_i$ by a plurality of phase angles ranging from 0° to 360°, wherein phase-rotating comprises performing a complex scalar multiplication $e^{-(j\beta_m)} P_i$ wherein $\alpha_m = m \times 3.6°$ and m=1, 2, ..., 100;
    detecting a plurality of motion curves $r_{i,m}[n]$ from all phase-rotated 2D matrices $P_i$ corresponding to all combinations of i and m;
    Fourier-transforming the plurality of motion curves $r_{i,m}[n]$ to produce a plurality of motion curve spectra $R_{i,m}(f)$ corresponding to all combinations of i and m;

calculating a temporospectral quality metric for all combinations of i and m, the temporospectral quality metric given by:

$$Q_{i,m} = \frac{\int_{0.1\,Hz}^{0.5\,Hz} |R_{i,m}(f)|df}{\int_{0.8\,Hz}^{\infty} |R_{i,m}(f)|df} \times \left(\frac{1}{\max_n r_{i,m}[n] - \min_n r_{i,m}[n]}\right);$$

and
selecting the optimum coil i* and the optimum phase angle m* according to:

$$(i^*, m^*) = \mathrm{argmax}_{(i,m)} Q_{i,m}.$$

3. The system of claim 1, wherein the spatial X axis is defined along a direction of maximum motion.

4. The system of claim 3, wherein the spatial X axis is defined along a superior-inferior axis.

5. A system for producing motion-corrected MR images of at least a portion of a patient, the system including:
an MRI scanner comprising a plurality of coils, the plurality of coils configured to detect a plurality of MR imaging datasets, each MR imaging dataset comprising a plurality of MR signals detected by one coil of the plurality of coils;
a controller operatively coupled to the MRI scanner, the controller comprising:
at least one processor and a non-volatile memory;
a current control unit and a pulse control unit operatively coupled to the MRI scanner, wherein the current control unit and the pulse control unit are configured to operate the MRI scanner to detect the plurality of MR imaging signals according to a 1D navigator imaging sequence; and
an image processing unit operatively coupled to the MM scanner, the image processing unit configured to:
receive the plurality of MR imaging datasets associated with the plurality of coils;
identify a motion cycle using an automated motion detection method, the motion cycle comprising a plurality of phases; and
partition the plurality of MR imaging datasets into a plurality of image groups, each image group comprising a portion of the plurality of MR imaging datasets associated with one of the phases of the motion cycle, wherein:
the 1D navigator imaging sequence comprises obtaining a plurality of scans, each scan comprising a 1D navigator spoke coincident with a fixed $k_x$ axis in k-space obtained prior to a corresponding stack of spokes distributed along a $k_z$ axis and oriented along an azimuth angle in k-space, and further comprises incrementally changing the azimuth angle prior to obtaining an additional scan,
the 1D navigator imaging sequence further comprises incrementally changing the azimuth angle according to an azimuth sampling scheme selected from the group consisting of a Golden Angle azimuth sampling scheme and a controlled frequency modulation azimuth sampling scheme, and
the controlled frequency modulation azimuth sampling scheme comprises calculating the azimuth angle as described by one of:

$$\varphi = (j^*180°/N)^*\cos(j^*180°) = (j^*180°/N)^*(-1)^j;\text{ and}$$

$$\varphi_j = (j^*180°/N)^*\cos(j^*2\pi^*f/f_s);$$

wherein j=(0, 1 ..., N−1), N is a total number of stacks of spokes, f is a modulation frequency and $f_s$ is a sampling frequency.

6. A method for producing motion-corrected MR images of at least a portion of a patient, the method including:
operating an MRI scanner comprising a plurality of coils according to a 1D navigator imaging sequence to detect a plurality of MR imaging datasets, each MR imaging dataset comprising a plurality of MR signals detected by one coil of the plurality of coils;
receiving the plurality of MR imaging datasets associated with the plurality of coils;
identifying a motion cycle using an automated motion detection method, the motion cycle comprising a plurality of phases, and
partitioning the plurality of MR imaging datasets into a plurality of image groups, each image group comprising a portion of the plurality of MR imaging datasets associated with one of the phases of the motion cycle, wherein:
detecting the plurality of MRI imaging datasets according to the 1D navigator imaging sequence comprises obtaining a plurality of scans, each scan comprising a 1D navigator spoke coincident with a fixed $k_x$ axis in k-space obtained prior to a corresponding stack of spokes distributed along a $k_z$ axis and oriented along an azimuth angle in k-space, and further comprises incrementally changing the azimuth angle prior to obtaining an additional scan,
incrementally changing the azimuth angle comprises changing the azimuth angle according to an azimuth sampling scheme selected from the group consisting of a Golden Angle azimuth sampling scheme and a controlled frequency modulation azimuth sampling scheme, identifying the motion cycle using an automated motion detection method further comprises:
for each MR imaging dataset, obtaining an inverse Fourier transform of each 1D navigator associated with each stack of spokes,
for each MR imaging dataset, arranging each inverse Fourier transform into a 2D matrix $P_i = P_i[x,n]$ wherein i is a coil index indicative of the coil associated with the MR imaging dataset, x is a position index indicative of a position of the inverse Fourier transform along a spatial X axis, the spatial X axis comprising the inverse Fourier transform of the k axis, and n is a discrete time index indicative of a time of data acquisition,
tuning each 2D matrix $P_i$ to identify an optimal coil i* and an optimal phase angle m*, based on a temporospectral quality metric, and
obtaining a motion curve $r_{i,m}[n]$ by detecting the location of each peak along each column of an optimum 2D matrix $P_i$, the optimum 2D matrix $P_i$ comprising the 2D matrix $P_i$ corresponding to the optimal coil i* and phase-rotated by the optimal phase angle m*, wherein the motion curve $r_{i,m}[n]$ describes the motion cycle.

7. The method of claim 6, wherein tuning each 2D matrix $P_i$ to identify an optimum coil i* and an optimum phase angle m* further comprises:
phase-rotating each 2D matrix $P_i$ by a plurality of phase angles ranging from 0° to 360°, wherein phase-rotating comprises performing a complex scalar multiplication expressed by $e^{-(j\alpha_m)}P_i$, wherein $\alpha_m = m \times 3.6°$ and m=1, 2, ..., 100;

detecting a plurality of motion curves $r_{i,m}[n]$ from all phase-rotated 2D matrices $P_i$ corresponding to all combinations of i and m;

Fourier-transforming the plurality of motion curves $r_{i,m}[n]$ to produce a plurality of motion curve spectra $R_{i,m}(f)$ corresponding to all combinations of i and m;

calculating a temporospectral quality metric for all combinations of i and m, the temporospectral quality metric given by:

$$Q_{i,m} = \frac{\int_{0.1\,Hz}^{0.5\,Hz} |R_{i,m}(f)| df}{\int_{0.8\,Hz}^{\infty} |R_{i,m}(f)| df} \times \left(\frac{1}{\max_n r_{i,m}[n] - \min_n r_{i,m}[n]}\right);$$

and selecting the optimum coil i* and the optimum phase angle m* according to:

$$(i^*, m^*) = \text{argmax}_{(i,m)} Q_{i,m}.$$

8. The method of claim 7, wherein detecting the plurality of MRI imaging datasets according to the 1D navigator imaging sequence further comprises obtaining a plurality of dual 1D navigator scans, each dual 1D navigator scan comprising the first 1D navigator spoke and a second 1D navigator spoke intersecting $k_x = k_y = k_z = 0$ in k-space, the first and second 1D navigator spokes obtained prior to the corresponding stack of spokes.

9. The method of claim 8, wherein identifying the motion cycle using an automated motion detection method further comprises:

for each MR imaging dataset, obtaining an inverse Fourier transform of each 1D navigator and 1D second navigator associated with each stack of spokes;

for each MR imaging dataset, arranging each inverse Fourier transform into a 3D matrix $P_i = P_i[x, x', n]$ wherein x' is a position index indicative of a position of the inverse Fourier transform along a spatial X' axis, the spatial X' axis comprising the inverse Fourier transform of the $k_{x'}$ axis, the spatial X' axis aligned with a second direction of relatively high motion;

tuning each 3D matrix $P_i$ to identify an optimal coil i* and an optimal phase angle m*, based on a temporospectral quality metric; and obtaining a motion curve $r_{i,m}[n]$ by detecting the location of each peak within each x-x' plane of an optimum 3D matrix $P_i$, the optimum 3D matrix $P_i$ comprising the 3D matrix $P_i$ corresponding to the optimal coil i* and phase-rotated by the optimal phase angle m*, wherein the motion curve $r_{i,m}[n]$ describes the motion cycle.

10. The method of claim 6, wherein the spatial X axis is defined along a direction of maximum motion.

11. The method of claim 10, wherein the spatial X axis is defined along a superior-inferior axis.

12. A method for producing motion-corrected MR images of at least a portion of a patient, the method including:

operating an MRI scanner comprising a plurality of coils according to a 1D navigator imaging sequence to detect a plurality of MR imaging datasets, each MR imaging dataset comprising a plurality of MR signals detected by one coil of the plurality of coils;

receiving the plurality of MR imaging datasets associated with the plurality of coils;

identifying a motion cycle using an automated motion detection method, the motion cycle comprising a plurality of phases; and partitioning the plurality of MR imaging datasets into a plurality of image groups, each image group comprising a portion of the plurality of MR imaging datasets associated with one of the phases of the motion cycle, wherein:

detecting the plurality of MRI imaging datasets according to the 1D navigator imaging sequence comprises obtaining a plurality of scans, each scan comprising a 1D navigator spoke coincident with a fixed $k_x$ axis in k-space obtained prior to a corresponding stack of spokes distributed along a $k_z$ axis and oriented along an azimuth angle in k-space, and further comprises incrementally changing the azimuth angle prior to obtaining an additional scan, incrementally changing the azimuth angle comprises changing the azimuth angle according to an azimuth sampling scheme selected from the group consisting of a Golden Angle azimuth sampling scheme and a controlled frequency modulation azimuth sampling scheme, and changing the azimuth angle according to the controlled frequency modulation azimuth sampling scheme further comprises calculating the azimuth angle as described by one of:

$$\varphi = (j*180°/N)*\cos(j*180°) = (j*180°/N)*(-1)^j;\text{ and}$$

$$\varphi_j = (j*180°/N)*\cos(j*2\pi*f/f_s);$$

wherein j=0, 1 ... N−1, N is the total number of stacks of spokes, f is a modulation frequency and $f_s$ is a sampling frequency.

* * * * *